(12) United States Patent
Plass

(10) Patent No.: US 6,893,820 B1
(45) Date of Patent: May 17, 2005

(54) DETECTION OF METHYLATED CPG RICH SEQUENCES DIAGNOSTIC FOR MALIGNANT CELLS

(75) Inventor: Christoph Plass, Columbus, OH (US)

(73) Assignee: The Ohio State University Research Foundation, Columbus, OH (US)

(*) Notice: Subject to any disclaimer, the term of this patent is extended or adjusted under 35 U.S.C. 154(b) by 204 days.

(21) Appl. No.: 09/775,398

(22) Filed: Jan. 31, 2001

(51) Int. Cl.$^7$ .................................................. C12Q 1/68
(52) U.S. Cl. ........................................ 435/6; 435/91.2
(58) Field of Search .................................. 435/6, 91.2

(56) References Cited

U.S. PATENT DOCUMENTS 6,214,556 B1    4/2001   Olek et al.

FOREIGN PATENT DOCUMENTS

WO    WO 99/28498    6/1999

OTHER PUBLICATIONS

Konishi (Journal of Oral Pathology and Medicine (1999) 28: 102–106).*
Plass et al. Oncogene. May 20, 1999. 18: 3159–3165.*
"Aberrant CpG–island methylation has non–random and tumour–type–specific patterns" by Costello, et al., *Nature Genetics,* vol. 25, Feb. 2000, pp. 132–138.
"Aberrant Hypermethylation of the Major Breakpoint Cluster Region in 17p1 1.2 in Medulloblastomas but not Supratentorial PNETs" by Fruhwald, et al., *Genes, Chromosomes & Cancer,* 30:38–47 (2001).
"Aberrant methylation of genes in low–grade astrocytomas" by Costello, et al., *Brain Tumor Pathol.,* (2000) 17:49–56.
Abstract—"DNA Methylation in Acute Myeloid Leukemia with Evidence of Involvement of Chromosome 11" by Rush, et al., American College of Veterinary Pathologists, Annual Meeting, 2000.
Abstract—"Promotor Hypermethylation in Medulloblastomas: Aspects of Tumor Biology and Potential Clinical Utility" by Fruhwald, et al., Pediatric Oncology, San Francisco, California, Jun., 2000.
Abstract—"DNA Hypermethylation in Acute Myeloid Leukemia (AML): Nonrandom Patterns with Preferential Involvement of Chromosome 11" by Rush, et al., The 42$^{nd}$ ASH Annual Meeting, San Francisco, California, Dec. 2000.
Abstract—"Testicular Germ Cell Tumors as a Model System to Study DNA Methylation" by Smiraglia, et al., Gordon Research Conference, Cancer Genetics and Epigenetic, Ventura Beach, California, Feb. 2000.

Abstract—"Global DNA Methylation Changes in Primary Lung Cancer" by Dai, et al., Gordon Research Conference, Cancer Genetics and Epigenetic, Ventura Beach, California, Feb. 2000.
Abstract—"Identification of Hypermethylated CpG Islands in Non–Small Cell Lung Cancer and Related Aberrant Gene Transciption" by Dai, et al., Stone Lab Meeting, Sep. 2000.
Abstract—"The contribution of DNA methylation to oncogenesis—results of a genome scanning approach in multiple human tumors" by Plass, Oncogenomics, Tucson, Arizona, Jan. 2001.
"An Arrayed Human Not I–EcoRV Boundary Library as a Tool for RLGS Spot Analysis" by Plass, et al., *DNA Research,* 4, 253–355 (1997).
"Methylation–specific PCR: A novel PCR assay for methylation status of CpG islands" by Herman, et al., *Proc. Natl. Acad. Sci. USA,* vol. 93, Sep. 1996, pp. 9821–9826.
"A New Tool for the Rapid Cloning of Amplified and Hypermethylated Human DNA Sequences from Restriction Landmark Genome Scanning Gels" by Smiraglia, et al., *Genomics,* 58, 254–262 (1999).
"Restriction landmark genome scanning for aberrant methylation in primary refractory and relapsed acute mycloid leukemia; involvement of the WIT–1 gene" by Plass, et al., *Oncogene,* (1999) 18, 3159–3165.
Medulloblastoma: A Developmental Abnormality of the Cerebellum. A comprehensive analysis of genetic and epigenetic alternations. Michael C. Frühwald. The Ph.D Thesis Ohio State University 1999 pp. i–180 Columbus Ohio USA.
Graff et al., "Mapping Patterns of CpG Island Methylation in Normal and Neoplastic Cells Implicates Both Upstream and Downstream Regions in de Novo Methylation", *The Journal of Biological Chemistry* (1997) vol. 272, No. 35, pp. 22322–22329.

* cited by examiner

Primary Examiner—Carla J. Myers
(74) Attorney, Agent, or Firm—Calfee, Halter & Griswold

(57) ABSTRACT

The present invention provides methods for determining the methylation status of CpG-containing dinucleotides on a genome-wide scale using infrequent cleaving, methylation sensitive restriction endonucleases and two-dimensional gel electrophoretic display of the resulting DNA fragments. Such methods can be used to diagnose cancer, classify tumors and provide prognoses for cancer patients. The present invention also provides isolated polynucleotides and oligonucleotides comprising CpG dinucleotides that are differentially methylated in malignant cells as compared to normal, non-malignant cells. Such polynucleotides and oligonucleotides are useful for diagnosis of cancer. The present invention also provides methods for identifying new DNA clones within a library that contain specific CpG dinucleotides that are differentially methylated in cancer cells as compared to normal cells.

5 Claims, 10 Drawing Sheets

DETECTION OF METHYLATED CPG RICH SEQUENCES DIAGNOSTIC FOR MALIGNANT CELLS

This invention was conducted, at least in part, with government support under National Institutes of Health Grants No: P30 CA16058 and CA80912 awarded by the National Cancer Institute. The U.S. government has certain rights in the invention

BACKGROUND OF THE INVENTION

Diagnosis of cancer, classification of tumors, and cancer-patient prognosis all depend on detection of properties inherent to cancer, or malignant cells, that are absent in normal, nonmalignant cells. Since cancer is largely a genetic disease, resulting from and associated with changes in the DNA of cells, one important method of diagnosis is through detection of related changes within the DNA of cancer cells. Such changes can be of two types. The first type of change is a genetic change that occurs when the sequence of nucleotide bases within the DNA is changed. Base changes, deletions and insertions in the DNA are examples of such genetic changes. The second type of change in the DNA is an epigenetic change. Epigenetic changes do not result in nucleotide sequence changes, but rather, result in modification of nucleotide bases. The most common type of epigenetic change is DNA methylation.

In mammalian cells, DNA methylation consists exclusively of addition of a methyl group to the 5-carbon position of cytosine nucleotide bases. In the process, cytosine is changed to 5-methylcytosine. Cellular enzymes carry out the methylation events. Only cytosines located 5' to guanosines in CpG dinucleotides are methylated by the enzymes in mammalian cells. Such CpG dinucleotides are not distributed randomly throughout the genome. Instead, there are regions of mammalian genomes which contain many CpG dinucleotides, while other areas of the genome contain few CpG dinucleotides. Such CpG-rich areas of the genome are called "CpG islands." Most often, CpG islands are located in the transcriptional promoter regions of genes.

Not all CpG islands are methylated However, the methylation status of CpG islands (i.e., whether the CpG dinucleotides within a particular CpG island are methylated or not) is relatively constant in cells. Nevertheless, the pattern of CpG island methylation can change and, when it does, often a new, relatively stable methylation pattern is established. Such changes in methylation of CpG islands can be either increases or decreases in methylation.

Methylation of CpG islands in the promoter region of a few specific genes has been observed in some types of human cancer. However, at present it is still uncertain whether the methylation status of multiple CpG islands in the genomic DNA of subjects suspected of having cancer can be used as a diagnostic tool for determining whether or not tissue obtained from such subjects contain malignant cells.

SUMMARY OF THE INVENTION

The present invention relates to methods for identifying CpG islands which are diagnostic of one or more cancers in a subject The method employs restriction landmark genomic scanning (RLGS) techniques and comprises separately digesting genomic DNA which has been obtained from malignant cells derived from a particular tumor tissue and genomic DNA which has been obtained from control cells derived from healthy tissue with an infrequently cutting restriction enzyme that is not capable of cleaving methylated recognition sites to provide a first set of DNA restriction fragments from the tumor tissue, referred to hereinafter as "malignant cell restriction fragments", and a first set of DNA restriction fragments from the healthy tissue, referred to hereinafter as "control cell restriction fragments"; attaching a detectable label to the ends of the malignant and control cell restriction fragments; digesting the labeled malignant and control cell restriction fragments with a second restriction enzyme; separating each set of restriction fragments on a gel; digesting the restriction fragments in each of the gels with a third more frequently cutting restriction enzyme; electrophoresing each set of restriction fragments in a direction perpendicular to the first direction to provide a first pattern of detectable malignant cell restriction fragments and a second pattern of detectable control cell restriction fragments; and comparing the second pattern to the first pattern to identify control cell restriction fragments, hereinafter referred to as "diagnostic fragments", which are absent, or exhibit an decreased intensity of label in the first pattern. Such fragments comprise CpG islands that are methylated in the malignant cells. Such patterns are useful for characterizing tissue which is suspected of containing malignant cells. Preferably, each of the diagnostic fragments is then isolated and sequenced, at least in part. In one preferred embodiment, the first restriction enzyme is NotI. In another preferred embodiment, the first restriction enzyme is AscI. Advantageously, the present method permits the detection of numerous methylation sites within the entire genome. In accordance with the present method, applicants have determined that particular CpG islands are preferentially methylated in DNA obtained from tumor tissues of subjects diagnosed as having breast cancer, glioma, acute myeloid leukemia, primitive neuroectodermal tumors of childhood, colon cancer, head and neck cancer, testicular cancer, and lung cancer.

The present invention also provides isolated polynucleotides, referred to hereinafter as "CpG diagnostic polynucleotides", and isolated oligonucleotides referred to hereinafter as "CpG diagnostic oligonucleotides", which are useful for characterizing tissue samples obtained from a subject suspected of having gliomas, acute myeloid leukemia, primitive neuroectodermal tumors of childhood, or cancer of the breast, colon, head and neck, testicle or lung. The CpG diagnostic polynucleotides and oligonucleotides both comprise a sequence which contains CpG islands that have been shown to be preferentially methylated in DNA that has been obtained from malignant cells of subjects diagnosed as having breast cancer, glioma, acute myeloid leukemia, primitive neuroectodermal tumor of childhood, colon cancer, head and neck cancer, testicular cancer or lung cancer. The CpG diagnostic polynucleotides are from 35 to 3000, preferably, 35 to 100 nucleotides in length, and comprise from 15 to 34, preferably 18 to 25 of the consecutive nucleotides contained with the sequences depicted in the accompanying DNA sequence listing, or sequences which are complementary thereto. The CpG diagnostic polynucleotides comprise two or, preferably, more CpG dinucleotides or dinucleotides which are complementary thereto. The CpG diagnostic oligonucleotides are from 15 to 34 nucleotides in length and comprise from 15 to 34 consecutive nucleotides contained within the sequences depicted in the sequence listing, or sequences which are complementary thereto. The CpG oligonucleotides comprises two or more CpG dinucleotides, or dinucleotides which are complementary thereto.

The present invention also relates to methods which employ the CpG diagnostic polynucleotides and oligonucleotides of the present invention to characterize tissue from patients suspected of having cancer. Such methods are based on the methylation status of CpG islands that have been shown to be preferentially methylated in DNA that has been obtained from tumor tissues of subjects diagnosed as having breast cancer, glioma, acute myeloid leukemia, primitive neuroectodermal tumor of childhood, colon cancer, head and neck cancer, testicular cancer and lung cancer. In one method, DNA which is isolated from suspected tumor tissue from a subject is digested into smaller fragments and reacted with a CpG diagnostic polynucleotides under stringent hybridization conditions. The reaction products are then assayed to determine the size or the sequence of the DNA fragment with which the CpG diagnostic polynucleotide has hybridized. The size or the sequence of the DNA fragment to which the CpG diagnostic polynucleotide has hybridized, hereinafter referred to as the "target DNA fragment", indicates whether the target DNA fragment comprises methylated or nonmethylated CpG islands. The presence of methylated CpG islands in the target DNA fragment indicates that the DNA has been obtained from a tumor or neoplasm for which the diagnostic CpG polynucleotide serves as a diagnostic marker.

In another method the DNA from the suspected tumor tissue is treated with a chemical compound which converts nonmethylated cytosines to a different nucleotide base. An example of such a compound is sodium bisulfite which converts non-methylated cytosines to uracil. The DNA is then reacted with at CpG diagnostic oligonucleotides under conditions which permit the CpG diagnostic oligonucleotide to hybridize with a complementary sequence in the DNA, referred to hereinafter as the "target sequence". The DNA is also reacted with a modified CpG diagnostic oligonucleotide. The modified CpG diagnostic oligonucleotide comprises a sequence that is complementary to a modified target sequence, i.e., a sequence in which the non-methylated cytosines in the target sequence are converted to a different nucleotide base, e.g. uracil, when treated with a chemical compound. The reaction products are then assayed to determine whether the DNA contains sequences which have hybridized with the CpG diagnostic oligonucleotide or with the modified CpG diagnostic oligonucleotide. Hybridization of the sample DNA with the CpG diagnostic oligonucleotide, as opposed to the modified CpG diagnostic oligonucleotide, indicates that the cytosines in the target sequence are methylated and that the DNA sample has been obtained from a tumor or neoplasm for which the CpG oligonucleotide has been shown to serve as a diagnostic marker.

The present invention also relates to a method of identifying genes whose expression is increased or decreased in cancer cells.

DETAILED DESCRIPTION OF THE INVENTION

Figure 1A:
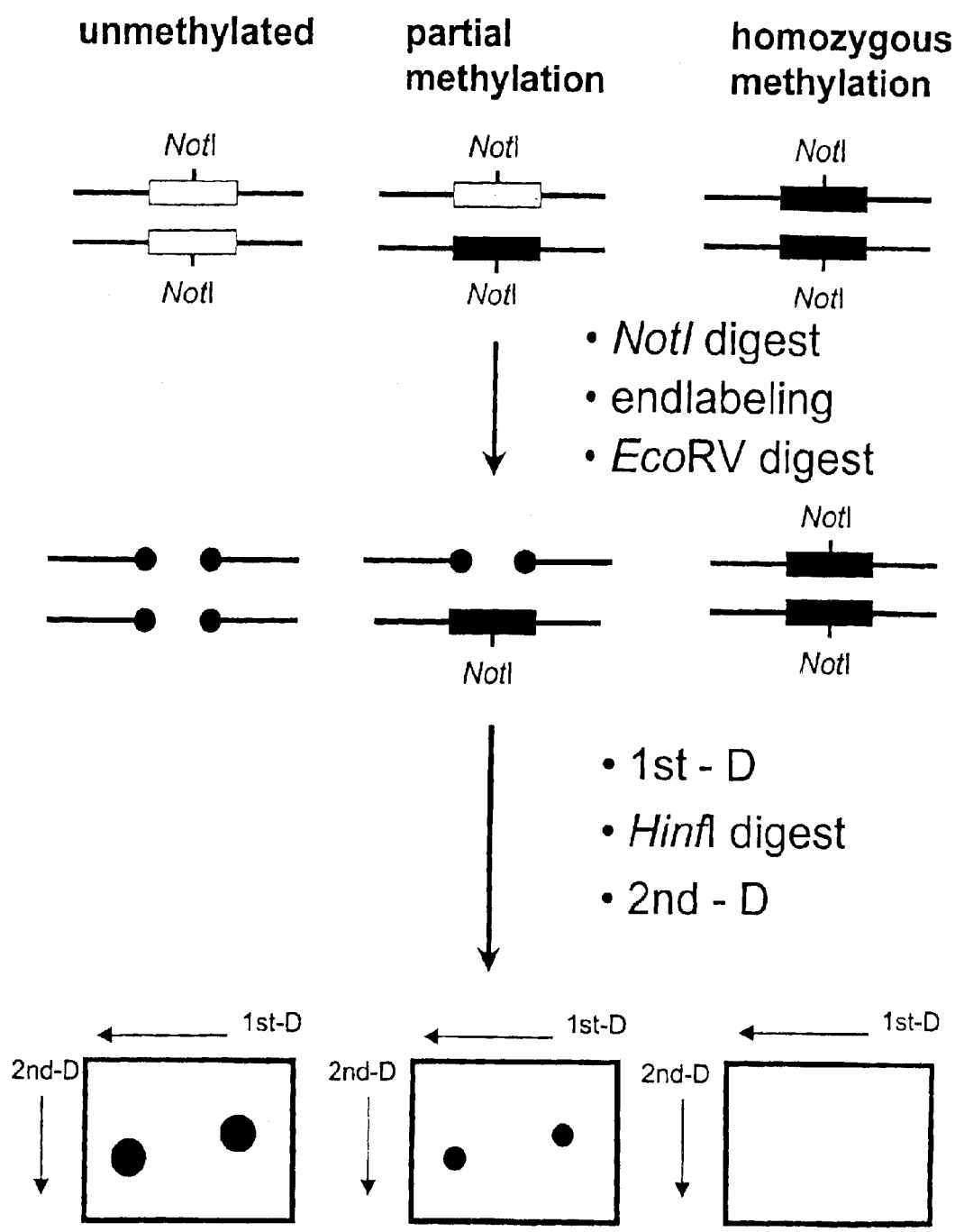
FIG. 1. Methylation detection in restriction landmark genomic scanning (RLGS) profiles. A, Diagram of the RLGS procedure showing the quantitative nature of methylation detection on Not fragments displayed on RLGS profiles. Methylation detection in RLGS profiles depends on the methylation sensitivity of the endonuclease activity of NotI. Differences in digestion are assessed by radiolabelling the DNA at cleaved NotI sites. Following further endonuclease digestion, two-dimensional electrophoretic separation and autoradiography, the intensity of a DNA fragment on the resultant RLGS profile quantitatively reflects the copy number and methylation status of the NotI fragment. A priori, this allows NotI fragments containing single-copy CpG islands to be distinguished from the abundant NotI fragments present in repeat elements and rDNA sequences. B, A portion of an RLGS profile from normal peripheral blood lymphocyte DNA displaying nearly 2,000 single-copy NotI fragments and 15–20 high copy-number fragments. First dimension separation of labeled NotI/EcoRV fragments extends from right to left horizontally. Following in-gel digestion with HinfI, the fragments are separated vertically downward into a polyacrylamide gel and autoradiographed. To allow uniform comparisons of RLGS profiles from different samples and different laboratories, each fragment is given a three-variable designation (Y coordinate, X coordinate, fragment number). The central region of the RLGS profile used for all comparisons described in this invention has 28 sections (1–5 vertically and B–G horizontally, the 4G and 5G sections were excluded due to high density and lower resolution of fragments). C, Enlarged view of profile section 2D, showing the numbers assigned to each NotI fragment D, Analysis of the GC content and CpG ratio {(number of CpGs)/(number of guanines)(number of cytosines)}(number of nucleotides analyzed) of 210 non-redundant NotI/EcoRV clones containing the Not/HinfI fragments seen in B and in other portions of the RLGS profile. Of 210 clones, 184 clones were randomly chosen and 26 corresponded to fragments which were frequently lost from tumor profiles. CpG islands have a GC content of greater than 50% and a CpG value of 0.6 or greater, relative to bulk DNA (average CG content of 40% and CpG ratio of 0.2). Nucleotide sequences were determined with greater than 99% accuracy overall. An average of 377 nt/clone were analyzed (not indicative of actual CpG island size). The average NotI/EcoRV clone size was approximately 2 kb.

In one aspect, the present invention relates to methods for identifying clones within a DNA library that can be used for cancer diagnosis and tumor classification, based on the methylation status of CpG dinucleotides contained within or closely adjacent to the specific clones. Such method employs methylation-sensitive restriction endonucleases (MSREs) and restriction landmark genomic scanning (RLGS) gels to identify new, differentially-methylated CpG islands within malignant cells obtained from patients diagnosed as having cancer. In accordance with the present invention, Applicants have identified 93 clones which can be used to determine whether a tumor biopsy from a patient contains benign or malignant cells.

To carry out such method, tissue (referred to hereinafter as "tumor tissue") which contains a tumor or neoplasm is obtained from a patient known to have a cancer. In some cases, the tumor tissue is obtained from a particular type of solid tumor which has bee surgically removed from the patient. In some cases, the tumor tissue is obtained from the hematopoietic system, such as for example, bone marrow or blood, of the patient The tumor tissue will have been determined to be from either a benign or malignant tumor or neoplasm.

Separately, tissue (referred to hereinafter as "healthy tissue") which does not contain a tumor or neoplasm is obtained from a subject. The healthy tissue, may be obtained by surgically removing normal tissue from the patient or by surgically removing normal tissue from a healthy control subject who does not have cancer. The healthy tissue may also come from the hematopoietic system, such as for example, bone marrow or blood, of a healthy control subject. The healthy tissue will have been determined to be nor-tumorigenic or non-neoplastic.

DNA is then isolated from both the tumor tissue and healthy tissue. If the tumor tissue is a solid tissue sample, such procedure may first comprise separating the individual cells contained within the tissue from each other. For example, if the tissue samples were frozen after surgical removal from a patient, cells may be separated from one another by grinding the frozen tissue with a mortar and pestle. DNA is then isolated from the individual cells using procedures well known to those skilled in the art. Commonly, such DNA isolation procedures comprise lysis of the individual cells using detergents, for example. After cell lysis, proteins are commonly removed from the DNA using various proteases. The DNA is then commonly extracted with phenol, precipitated in alcohol and dissolved in an aqueous solution.

In the procedures which follow, the DNA obtained from the tumor tissue is treated separately from the DNA obtained from healthy tissue (i.e., the two DNAs are not mixed). The DNAs are separately analyzed using a method called restriction landmark genomic scanning (RLGS). The purpose is to analyze both DNAs separately. The two analyses are then compared in order to identify CpG islands that distinguish cancer cells from normal cells.

Both DNA samples are treated with restriction enzymes and the free ends that result from the restriction enzyme cleavage are labeled. However, since the isolated DNA is in linear pieces, there are free ends that exist before the DNA is cleaved with the restriction enzymes. To prevent these ends from being labeled, the ends, preferably, are blocked before restriction enzyme treatment. Such blocking can be done by addition of dideoxynucleotides and sulfur-substituted nucleotides to the free ends before treatment with restriction enzymes. Subsequently, when the DNA is cleaved by restriction enzymes and labeled, only the ends resulting from the restriction enzyme cleavage will be labeled.

After the reaction to block free ends, the DNA samples are cleaved with a first restriction enzyme that can be characterized as an infrequently cleaving, methylation-sensitive restriction enzyme. Examples of suitable first restriction enzymes are NotI, AscI, BssHII and EagI. As used herein the term "infrequently cleaving" refers to a restriction enzyme that is expected to cleave genomic DNA at intervals greater than 10 kilobases. For example, NotI is an infrequently cleaving restriction enzyme. NotI recognizes a nucleotide sequence of 8 base pairs (bp) in the genome (i.e., 5'GCGGCCGC3') and cleaves the DNA at this site. There are an estimated 4000–5000 of such NotI recognition sequences within the human genome. It is estimated that such recognition sequences are spaced at approximately 1 megabase (Mb) intervals within the genome. In contrast, a frequently cleaving restriction enzyme is expected to cleave the human genome at from 5–10 kb intervals. Such an enzyme will have approximately 100-times more cleavage sites within the human genome than infrequently-cleaving enzymes. Such frequently cleaving enzymes usually recognize a nucleotide sequence of less than 8 bp in the genome and cleave the DNA at that site. However, not all restriction enzymes that have nucleotide recognition sequences of less than 8 bp are frequently cleaving enzymes. BssHII and EagI both have 6 bp recognition sequences but the recognition sequences for these two enzymes are spaced at intervals within the genome that are greater than 10 kb. "Methylation sensitive" as used herein refers to any enzyme that is unable to cleave DNA at its normal restriction site if one or more nucleotides within the recognition sequence is methylated. For example, the restriction enzyme NotI will cleave the 5'GCGGCCGC3' recognition sequence if the sequence does not contain a 5 methylcytosine. However, the NotI enzyme will not cleave this sequence if any of the cytosines have been methylated to become 5-methylcytosine.

Following digestion of the DNA with the first restriction enzyme, the ends of the DNA fragments are labeled. This can be done, for example, by attachment of nucleotides carrying a detectable label, such as a radiolabel, to the ends of the DNA sample. Typically, attachment is accomplished by filling in the recessed DNA ends left by cleavage with the first restriction enzyme such that the ends become blunt (i.e., non-recessed). Such end-filling reaction may employ deoxy-nucleoside triphosphates having a radiolabeled phosphate at the α phosphate position. Such labeled phosphate is preferably $^{32}$P.

The labeled fragments from each sample are then cleaved with a second restriction enzyme. Such second restriction enzyme preferably cleaves human DNA at average intervals of between 5–10 kb. Such enzymes normally have a 6 bp recognition sequence. Preferably, the second restriction enzyme is not methylation sensitive. Examples of suitable second restriction enzymes are PstI, PvuI, EcoRV or BamHI. Cleavage of the DNA fragments with the second restriction enzyme provides a second set of fragments, labeled at the ends-left by cleavage with the first enzyme. Many of such second fragments are smaller than the fragments resulting from cleavage with the first restriction enzyme.

The DNA fragments are then separated from one another. Preferably this separation is based on size. Preferably this separation is performed by first-dimension electrophoresis through an agarose tube-shaped gel of approximately 60 cm in length.

After electrophoresis through the tube-shaped gel, the DNA is digested within the gel with a third restriction enzyme. Such third restriction enzymes preferably have recognition sequences of 4 or 6 bp. Such third restriction enzymes also have the property of being able to cleave DNA which is embedded within agarose. One such enzyme is HinfI.

After cleavage by the third restriction enzyme, the DNA is again separated based on size, preferably by electrophoresis through a polyacrylamide gel. Subsequently, the separated DNA fragments are detected based on the labeled ends of the DNA fragments. In those cases where the fragments are radiolabeld, detection is by autoradiography of the two-dimensional gel. Such autoradiography provides a pattern of DNA fragments or "spots." Such pattern is called an RLGS profile.

Each fragment on the RLGS profile obtained from using the DNA from healthy tissues is uniquely identified by its location on the autoradiograph (Y coordinate, X coordinate, fragment number). For each fragment location on the RLGS profile obtained from healthy tissue DNA, the identical location is observed on the RLGS profile obtained from tumor tissue DNA.

In a fragment by fragment comparison of RLGS profiles obtained from tumor tissue DNA with healthy tissue DNA, three different patterns are possible. First, for a given fragment on the healthy tissue RLGS profile, there may be a corresponding fragment at the same location, and of the same intensity, on the tumor tissue RLGS profile. This indicates that the first restriction enzyme cleaved both DNAs at the same sequences (FIG. 1A). This indicates that there were no differences in methylation of the NotI nucleotide recognition sequence of that fragment between the tumor tissue DNA and the healthy tissue DNA.

Second, for a given fragment on the healthy tissue RLGS profile, there may be no fragment at the same location on the tumor tissue RLGS profile. Such a pattern indicates that the first restriction enzyme did not cleave the tumor tissue DNA at the recognition sequence required to produce that specific fragment, but did cleave at such sequence within the healthy tissue DNA (FIG. 1A). This indicates that there was methylation within the NotI recognition sequence in the tumor tissue DNA but not in the healthy tissue DNA.

Third, for a given fragment on the healthy tissue RLGS profile, there may be a corresponding fragment at the same location on the tumor tissue RLGS profile, but the intensity of the fragment may be of decreased intensity. Such a pattern indicates that the first restriction enzyme cleaved one of two copies (i.e., the genome is diploid) of the tumor tissue DNA at the recognition sequence required to produce that specific fragment (FIG. 1A). In healthy tissue DNA, the first restriction enzyme cleaved both copies of the recognition sequence. This indicates that there was methylation within one of two NotI recognition sequences in the tumor tissue DNA.

Through comparisons of RLGS profiles obtained from healthy tissue DNA with profiles obtained from a large number of different tumor tissue DNAs, loss of specific fragments in multiple tumors can be associated with a specific type of cancer. Loss of such fragments from RLGS profiles, therefore, can be diagnostic for cancer in a subject. For example, loss of a specific fragment (i.e., methylation of the first restriction enzyme site at the end of said fragment) in a high percentage of tumor tissue DNAs from women known to have breast cancer can be diagnostic for breast cancer in subjects suspected of having the disease. To perform such a diagnostic analysis, DNA isolated from a patient suspected of having breast cancer would be analyzed by RLGS, as described above, to determine whether there was loss of one or more fragments in RLGS profiles that are known to be lost at high frequency in women known to have breast cancer. Similarly, loss of other specific fragments can be diagnostic for other cancers, such as for example, colon cancer, head and neck cancer, lung cancer, testicular cancer, neuroectodermal cancer, gliomas, acute myeloid leukemias, and others.

Loss of a specific fragment in RLGS profiles from multiple tumors can also be diagnostic of several types of cancer, rather than a single type of cancer. For example, loss of a specific fragment can occur in a high percentage of tumor tissue DNAs obtained from individuals with either breast, colon or lung cancer. Loss of such a spot from RLGS profiles using DNA obtained from a patient suspected of having cancer would be diagnostic for either breast, colon or lung cancer in that patient.

Isolated Polynucleotides and Oligonucleotides Diagnostic for Cancer

Individual DNA clones that contain the DNA present in each spot or fragment that makes up an RLGS profile can be obtained. This is done by constructing a DNA library of healthy tissue DNA that has been cleaved with the same first and second enzymes used to perform the RLGS gel analysis. Such DNA library will contain individual clones, each clone comprising DNA that is present in a single spot of the RLGS profile. The totality of clones within the library is representative of the combined DNA spots in the RLGS profile.

Individual clones within the library can be identified that contain the DNA of each spot on the RLGS profile. This can be done by taking DNA from one or a few individual clones of the DNA library and mixing it with healthy tissue DNA, before RLGS analysis is begun. When this mixture of DNAs is used to produce an RLGS profile, the intensity of the spots that contain the same DNA as the individual clones added to the mixture will be increased. By performing multiple analyses of this type, each spot on an RLGS profile can be matched up with a DNA clone within the library. The result of such an analysis is an ordered human genomic library of restriction fragments containing the same subset of genomic fragments as those displayed on RLGS profiles. In such ordered genomic libraries, an individual library clone corresponding to any spot or fragment in an RLGS profile can be rapidly located.

To design diagnostic CpG polynucleotides and oligonucleotides, tie sequence of the DNA within each clone (referred to hereinafter as a "diagnostic clone") that corresponds to a spot that is absent or exhibits decreased intensity on the RLGS profile of the DNA from malignant tumor tissue is sequenced using standard techniques. Once sequence information is obtained, regions comprising multiple CpG dinucleotides are located. Such regions serve as the target sequence for the CpG polynucleotides and oligonucleotides.

The CpG polynucleotides are from 35 to 3000, preferably from 35 to 1500 nucleotides in length and comprise two or, preferably, more CpG dinucleotides or dinucleotides which are complementary thereto. The CpG diagnostic oligonucleotides are from 15 to 34 nucleotides, preferably from 18 to 25 nucleotides, in length and comprise at least two CpG dinucleotides or dinucleotides which are complementary thereto. The CpG diagnostic polynucleotides and oligonucleotides each comprise a sequence which is substantially complementary to target sequences containing CpG islands that are known to be preferentially methylated in the DNA from one or more types of cancer cells. "Substantially complementary" means that there is enough complementarity between the CpG diagnostic polynucleotides or oligonucleotides and the target sequence so that hybridization occurs between the CpG diagnostic polynucleotides and oligonucleotides under stringent conditions, preferably under highly stringent conditions. Such assays include hybridization assays, such as for example Southern analysis, where the sample DNA is reacted with the CpG diagnostic polynucleotide under stringent hybridization conditions.

The term "stringent conditions, as used herein, is the "stringency" which occurs within a range from about Tm-5 (5 below the melting temperature of the probe) to about 20 C below Tm. "Highly Stringent hybridization conditions" refers to an overnight incubation at 42 degree C. in a solution comprising 50% formamide, 5×SSC (750 mM NaCl, 75 mM sodium citrate), 50 mM sodium phosphate (pH 7.6), 5×Denhardt's solution, 10% dextran sulfate, and 20 g/ml denatured, sheared salmon sperm DNA, followed by washing the filters in 0.2×SSC at about 65 degree C. As recognized in the art, stringency conditions can be attained by varying a number of factors such as the length and nature, i.e., DNA or RNA, of the probe; the length and nature of the target sequence, the concentration of the salts and other components, such as formamide, dextran sulfate, and polyethylene glycol, of the hybridization solution. All of these factors may be varied to generate conditions of stringency which are equivalent to the conditions listed above.

Changes in the stringency of hybridization and signal detection are primarily accomplished through the manipulation of formamide concentration (lower percentages of formamide result in lower stringency); salt conditions, or temperature. For example, moderately high stringency conditions include an overnight incubation at 37 degree C. in a solution comprising 6×SSPE (20×SSPE=3M NaCl; 0.2 M NaH$_2$PO$_4$; 0.02M EDTA, pH 7.4), 0.5% SDS, 30% formamide, 100 ug/ml salmon sperm blocking DNA; followed by washes at 50 degree C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Such assays also include polymerase chain reactions (PCR) where the sample DNA and the diagnostic CpG oligonucleotides are reacted, preferably under conditions which result in the synthesis of a single PCR product. Computer programs, such as for example, the "Primer3" program that can be accessed via the internet at <URL: genome.wi.mit.edu/cgi-bin/primer/primer3_www.cgi> can be used to determine the size and sequence of the CpG diagnostic oligonucleotides. Optimum conditions are determined empirically.

The CpG diagnostic polynucleotides and oligonucleotides are made using standard techniques. For example, these polynucleotides and oligonucleotides may be made using commercially available synthesizers.

Diagnostic Methods

In another aspect, the present invention relates to methods which use the CpG diagnostic polynucleotides and oligonucleotides to characterize tissue samples from a subject suspected of having cancer, referred to hereinafter as test sample DNA. To do this, DNA is isolated from the cells of the tissue sample of the patient. Preferably, DNA that serves as a control is also obtained from healthy tissue of the test subject or a control subject as described previously. The diagnostic methods comprise reacting the test sample DNA with the diagnostic CpG polynucleotide or oligonucleotide and assaying the products that are formed as the result of the reaction. In some cases, the sample DNA is digested into smaller fragments prior to reaction with the CpG diagnostic polynucleotides or oligonucleotides. In some cases, a portion of the test sample DNA is first reacted with a chemical compound, such as for example sodium bisulfite, which converts methylated cytosines to a different nucleotide base.

Southern Blot Analysis

One such method for diagnosing cancer in a patient involves cleavage of the test sample DNA with a methylation sensitive enzyme, then Southern blot analysis of said cleaved DNA using a CpG diagnostic polyncleotide or oligonucleotide as a probe. For example, the DNA from the patient and the control, healthy tissue DNA are separately cleaved with a methylation-sensitive restriction endonuclease, such nuclease being the same first restriction enzyme used to identify the diagnostic spot in the RLGS profile that corresponds to the CpG diagnostic polynucleotide or oligonucleotide. After cleavage, the test sample and control DNAs are electrophoretically separated by size in different lanes of the same agarose gel and blotted to a membrane that can be used in hybridization, such as for example, nitrocellulose or nylon. The membrane is then used in a hybridization reaction with a labeled CpG diagnostic polynucleotide or oligonucleotide. The labeled CpG diagnostic polynucleotide or oligoneucleotide will hybridize to complementary DNA sequences on the membrane. After hybridization, the location on the membrane where the probe hybridized to the control and patient DNAs is visualized. Such locations will identify DNA fragments or bands within the control and patient DNAs containing the same sequence as the CpG diagnostic polynucleotide or oligonucleotide. Hybridization of the probe to a fragment within the patient DNA that is of higher molecular weight than that of the fragment within the control DNA to which the probe hybridized, indicates that a restriction endonuclease cleavage site flanking the target sequence of the CpG diagnostic polynucleotide or oligonucleotide was not cleaved due to methylation Such result indicates that the tissue is from a cancer for which the CpG diagnostic polynucleotide or oligonucleotide serves as a diagnostic tool.

A second method for diagnosing cancer in a patient involves cleavage of patient DNA with a methylation-sensitive restriction endonuclease, such nuclease being the same first restriction enzyme used to identify the diagnostic spot in the RLGS profile that corresponds to the fragment Such nuclease will cleave the patient DNA at the diagnostic recognition sequence only if the DNA is unmethylated. Using nucleotide information derived from sequencing of the library clone corresponding to the diagnostic spot on the RLGS gel, primers for PCR are selected that span the diagnostic recognition sequence. Using the primers, PCR is performed on the DNA. PCR amplification of the sequences will be successful only if the diagnostic nucleotide sequence in the patient DNA had been methylated and was not cleaved by the enzyme. Successful PCR amplification, therefore, is indicative of cancer in the patient.

Methods Employing a Chemically-Modified DNA Test Sample

Another group of methods for diagnosing cancer in a patient using CpG diagnostic polynucleotides and oligonucleotides are based on treatment of patient DNA with sodium bisulfite which converts all cytosines, but not methylated cytosines, to uracil. The bisulfite converted patient DNA can then be analyzed in a number of different ways. One method of analysis is direct sequencing of the DNA to determine whether the sequence contains cytosine or uracil. Such DNA sequencing requires primers adjacent to the sequenced region to be made. Such primers would be based on DNA sequence information obtained from the diagnostic RLGS spots.

Another method of analyzing bisulfite converted patient DNA is a method called "methylation sensitive PCR" (MSR). In MSR, primers are designed to comprise a sequence which is substantially complementary to the the CpG islands which are known to be preferentially methylated in DNA of cells found in one or more type of tumor tissues. Two sets of PCR primers are made to encompass this region. One set of primers is designed to be complementary to the sequence that was changed by bisulfite (i.e., cytosines that were originally unmethylated and changed to uracil). As discussed above, these are the modified CpG diagnostic oligonucleotides. A second set of primers is designed to be complementary to the same sequence that was not changed by bisulfite (i.e., cytosines that were methylated and not changed to uracil). As discussed above these are the unmodified CpG diagnostic oligonucleotides, i.e the oligonucleotides which containe at least two CpG dinucleotides or dinucleotides which are complementary thereto. Two sets of PCR reactions are then run, one reaction with each set of primers, using DNA from the subject as the template. In the case where cytosines within the target sequence of the subject DNA are not methylated, the target sequence will be modified by the chemical reaction and the primers complementary to the modified sequence, i.e., the modified CpG diagnostic oligonucleotides, will produce a PCR reaction product while the primers complementary to the methylated sequence, i.e., the unmodified CpG diagnostic oligonucleotides, will not produce a PCR product. In the case where cytosines within the target sequence of the subject DNA are methylated, the target sequence will not be altered by the reaction with the sodium bisulfite, and the primers complementary to the unaltered sequence, i.e., the unmodified CpG diagnostic oligonucleotides, will produce a PCR reaction product while the modified CpG diagnostic oligonucleotides, which are complementary to the modified target sequence (i.e., unmethylated sequence) will not produce a PCR product.

A modification of MSR is bisulfite treatment of patient DNA and PCR amplification of said DNA using primers designed to amplify either methylated or unmethylated sequences. The PCR product is then digested with a restriction enzyme that will cleave or not depending on whether said product contains uracil (rather, thymidine, the complement of uracil; found in PCR product if original patient DNA contained unmethylated cytosine) or cytosine (found in PCR product if original patient DNA contained methylated cytosine).

Another technique referred to as MS-SnuPE, uses bisulfite/PCR followed by primer extension, where incorporation of C (vs. T) denotes methylation.

Methods of Identifying Genes

In another aspect of the invention, the CpG diagnostic polynucleotides and oligonucleotides can be used as probes to to identify genes whose expression is increased or decreased in cancerous tissues. To do this, CpG diagnostic polynuceotides are reacted with individual clones of the DNA library. The clones which hybridize with the CpG diagnostic polynucleotide can then be analyzed to determine if they contain an open reading fires that could encode proteins. To determine if the CpG diagnostic polynucleotide hybridizes with the promoter region of a known gene, the open reading frame sequence is analyzed by searching existing DNA databases. For example, GenBank databases can be searched using the BLAST algorithm. If no known genes that correspond to a library clone is found, the sequence can be searched for open reading frames that could encode a protein. Such searching can be performed using commercially available sequence analysis programs commonly known to those skilled in the art. GCG is an example of one such program.

Sequences from clones of the DNA library that contain either known genes or open reading frames can be used as probes to determine whether genes encoded by the sequences are expressed in tumor tissues as compared to control, healthy tissues. To do this, RNA, preferably messenger RNA (mRNA) is isolated from healthy tissue and from tumor tissue from which it is desired to test expression. Such RNA is examined for the presence of expressed transcripts encoded by the sequences obtained from the library. Examination for the presence of expressed transcripts can be performed using a number of methods. One method is Northern blotting where the isolated RNA is separated by size using gel electrophoresis and then blotted to a hybridization membrane. A fragment, polynucleotide or oligonucleotide from the sequence obtained from a library clone is labeled and then used to probe the hybridization membrane containing the size-separated RNA. Detection of hybridization of the probe to the membrane indicates presence of a transcript encoded by the sequence and indicates expression of the gene encoded by that sequence.

Another method to examine isolated RNA for the presence of expressed transcripts is to use RT-PCR analysis. In such analysis, primers are designed and made that span a region of the gene whose expression is to be tested. The isolated RNA is reverse transcribed into DNA using reverse transcriptase. Such DNA is then amplified with the designed primers using PCR. PCR products are visualized after electrophoresis. The presence of PCR products on the gel indicates that the gene encompassed by the designed primers was expressing RNA transcripts. Such analysis can identify and determine genes whose expression is changed in cancer cells as compared to normal, non-cancerous cells.

The following examples are for purposes of illustration only and are not intended to limit the scope of the invention as defined in the claims which are appended hereto.

EXAMPLES

Example 1

Identification of Diagnostic Markers Using NotI and RLGS

A. Isolation and Enzymatic Processing of Genomic DNA

Tissue from solid tumors was obtained as surgical tissue samples. Where possible, surrounding non-tumor tissue was taken and used as a control. Where it was not possible to obtain patient-matched normal tissue, normal tissue from multiple patients was used. Tissue samples from patients with acute myelogenous leukemis (AML) consisted of either bone marrow aspirates or peripheral blood. Normal samples were obtained from the same patients who were in remission after chemotherapy.

The surgically removed tissues were quickly frozen in liquid nitrogen and stored a −80° C. prior to isolation of DNA. When DNA was ready to be isolated, 2 ml of lysis buffer (10 mM Tris, pH 8.0; 150 mM EDTA, 1% sarkosyl) was added to 100–300 mg of tissue in a 50 ml Falcon tube and frozen in liquid nitrogen. The frozen mixture was then removed from the tube, wrapped in aluminum foil, and quickly broken into pieces with a hammer. The broken pieces of cells were transferred to a chilled mortar and ground to a powder with a chilled pestle. For peripheral blood samples, cells were separated on a sterile Histopaque-1077 (SIGMA) gradient and stored id at −80° C. before DNA isolation Cells were transferred to a 50 ml tube and 15–25 ml of lysis buffer containing 0.1 mg proteinase K per ml of lysis buffer was added and mixed using a glass rod. The mixture was incubated at 55° C. for 20 min with gentle mixing every 5 min. The mixture was then placed on ice for 10 min. Subsequently, an equal volume of PCI (phenol:chloroform:isoamylalcohol in a ratio of 50:49:1) was added and the tubes containing the mixture were gently rotated for 30–60 min. The tubes were then centrifuged for 30 min at 2500 rpm and the separated, aqueous phase was transferred to a new 50 ml tube using a wide-bore pipette. The PCI extraction was repeated one time. The collected aqueous phase containing the DNA was transferred to dialysis tubing and dialyzed against 4 L of 10 mM Tris, pH 8 for 2 hr. The dialysis tubing was then transferred into fresh 10 mM Tris and dialyzed overnight at room temperature. One additional dialysis was performed in fresh 10 mM Tris for an additional 2 hr. The DNA was then transferred from the dialysis tubing to 50 ml tubes and RNase A was added to a final concentration of 1 μg/ml. The mixture was incubated at 37° C. for 2 hr. Subsequently, 2.5 volumes of 100% ethanol were added to the DNA and the mixture was gently rotated. The insoluble DNA was transferred to a microfuge tube, centrifuged briefly, and the remaining alcohol removed. The pellet was briefly dried in air. The DNA in the pellet was resuspended to a final concentration of 1 μg/μl. Such isolated DNA had an average size of 200–300 kb.

The isolated genomic DNA was blocked at ends where the DNA had been sheared. Blocking was done by addition of dideoxynucleotides and sulfur-substituted nucleotides. In a 1.5 ml tube, 7 μl of genomic DNA solution was added along with 2.5 μl of blocking buffer (1 μl 10×buffer 1, 0.1 μl 1 M DTT, 0.4 μl each of 10 μM dGTPαS, 10 μM ddATP, 10 μM ddTTP, and 0.2 μl 10 μM dCTPαS; buffer 1 consists of 500 mM Tris, pH 7.4, 100 mM $MgCl_2$, 1 M NaCl, 10 mM DTT) and 0.5 μl DNA polymerase I. The mixture was mixed thoroughly and incubated at 37° C. for 20 min. The mixture was then incubated at 65° C. for 30 min to inactivate the polymerase. The reaction was then cooled on ice for 2 min. The DNA was digested with NotI by adding to the sample, 8 μl of 2.5×buffer 2 (20×buffer 2 is 3 M NaCl, 0.2% Triton X-100, 0.2% BSA) and 2 μl (10 U/μl) of NotI. The sample was incubated at 37° C. for 2 hr. The DNA was then radioactively labeled. This was done by adding to the sample 0.3 μl 1 M DTT, 1 μl [α-$^{32}$P]-GTP, 1 μl [α-$^{32}$P]-dCTP and 0.1 1 μl[α-$^{32}$P]-GTP Sequenase ver 2.0 (13 U/μl). The mixture was incubated at 37° C. for 30 min. The DNA was then digested with EcoRV by adding to the sample 7.6 μl second enzyme digestion buffer (1 μl 1 mM ddGTP, 1 ul 1 mM ddCTP, 4.4 μl dd$H_2O$, 1.2 μl 100 mM $MgCl_2$) and 2 μl EcoRV (10 U/μl). The mixture was incubated at 37° C. for 1 hr. Then, 7 μl of 6× first-dimension loading dye (0.25% Bromophenol Blue, 0.25% Xylene Cyanol, 15% Ficoll type 400) was added.

B. First Dimension Gel Set-up and Electrophoresis

To make the 60 cm long agarose tube-shaped gel, a gel holder was made. To do this, a sharp razor was used to cut one end of PFA-grade teflon tubing (PFA 11 thin wall, natural; American Plastic, Columbus, Ohio) at an angle to make a bevel. The beveled end of the tubing was fed into glass tubes (4 mm inner diameter, 5 mm outer diameter, 60 cm long). Using a hemostat, the beveled end was pulled up through the tapered end of the glass rod until it protruded 2 to 4 cm. The tubing was cut horizontally at the same end, leaving a 2 mm protrusion (this is the top of the gel holder). The opposite end was cut horizontally, leaving a 5 to 6 cm protrusion from the glass tube. The gel holder was inverted and the top protruding end was pressed firmly against a hot metal surface (metal spatula heated by a Bunsen burner) to fold the edges of the teflon outward onto the rim of the glass support A rubber stopper with cored center was pulled over the top end of the gel holder until it was just past the taper of the glass rod. A two-way stopcock was attached to a 10 ml syringe and then to the gel holder via 2 to 3 cm of flexible tubing. The stopcock valve was adjusted to the open position.

Then, to a clean 200 ml glass bottle was added, 60 ml 2×Boyer's buffer (20× is 1 M Tris, 360 mM NaCl, 400 mM sodium acetate, 40 mM EDTA) and 0.48 g Seakem GTG agarose (0.8%). The mixture was heated in a microwave oven until the agarose was dissolved. The mixture was then equilibrated to 55° C. in a water bath. With the stopcock valve in the open position, the protruding teflon tube was lowered into the molten agarose solution. The gel solution was suctioned into the gel holder until the gel solution reached 1–2 cm from the top of the gel holder. The stopcock valve was then closed. Keeping the gel upright, the gel was suspended from a ring stand. The gel was allowed to solidify for 20 min.

The stopcock valve was then opened and the syringe and connecting tubes were removed from each gel. After adding 2×Boyer's buffer to the bottom of the first dimension gel apparatus (C.B.S. Scientific), the gels were lowered into the first dimension gel apparatus, seating the rubber stopper firmly into the appropriate holes in the top portion of the apparatus. The top chamber was filled with 2×Boyer's buffer.

Between 1.0–1.5 μg of DNA was loaded onto each gel. The sample was electrophoresed at 110 V for 2 hr, and then 230 V for 24 hr.

C. In-gel Digest

After the DNA was electrophoresed in the first dimension in the agarose tube gel, the DNA was further digested with an additional restriction endonuclease so it could be electrophoresed in the second dimension. In order to perform this additional endonuclease digestion, the buffer and gel holders were removed from the first dimension apparatus.

The gel was extruded into a pan containing 1×buffer K (10×buffer K is 200 mM Tris, pH 7.4, 100 mM MgCl2, 1 M NaCl) by forcing the gel out through the bottom of the gel holder. This was accomplished using a 1 ml syringe fitted with a pipet tip and filled with buffer K. The tip was firmly inserted into the top of the gel holder and the plunger depressed until the gel began to come out through the bottom of the get holder. The 1 ml syringe was replaced with a 5 ml syringe, and the plunger was depressed until the entire gel was expelled. With a razor, a bevel was cut in the low molecular weight end of the gel and a horizontal cut was made at the high molecular weight end so that the gel was approximately 43 cm in length. The gel length was now the same as the width of the second dimension gel.

The gel was placed into a separate 50 ml tube containing 40 ml of 1×buffer K. The tube was incubated for 10 min at room temperature. The buffer was poured off and the gel incubated in 1×buffer K for an additional 10 min. The buffer K and gel was poured into a pan containing fresh buffer K. Using a 10 ml syringe attached to restriction digest tubing (PFA grade teflon, 9, thin wall, natural; 2.7 mm inner diameter and approximately 3.3 mm outer diameter, American Plastic, Columbus, Ohio), via a 1 to 2 cm segment of flexible tubing, the gel was suctioned into the digest tubing, low molecular weight (beveled) end first. The gel was suctioned into the digest tubing by placing the end of the tubing in line with the beveled end of the gel and pulling the syringe plunger. The tubing was positioned vertically, with the syringe at the bottom and remaining buffer from the tubing was suctioned into the syringe.

In a clean tube, a 1.6 ml mix of 1×HinfI restriction enzyme buffer (50 mM NaCl, 10 mM Tris pH 7.9, 1 mM DTT), 0.1% BSA, and 750 U of HinfI restriction enzyme was made. The open end of the digest tubing was placed into the tube containing restriction digestion solution. Holding the syringe end up, suction was applied until a small amount of digestion solution appeared in the syringe. The digest tubing was removed and both ends were oriented upward in a U-shape. The syringe was removed and the two ends of the tubing were attached to form a closed circle. This was placed in a moist chamber and incubated at 37° C. for 2 hr.

D. Second Dimension Electrophoresis

The digested DNA was now run in the second dimension using a 5% non-denaturing acrylamide gel with a 0.8% agarose spacer. To do this, the second dimension gel apparatus (C.B.S. Scientific) was first assembled. All glass plates were cleaned thoroughly and the non-beveled face of each plate was coated with Gelslick or Sigmacote (only once every 10 uses). The back half of the apparatus was laid horizontally on a table top with the upper buffer chamber hanging over the table edge. The two small clear plastic blocks were inserted at the bottom corners of each apparatus. A glass plate was placed in the apparatus, beveled edge facing upward and near the upper buffer chamber, followed by two spacers, one along each side. Glass plates and spacers were added in this manner until the fifth plate had been added. After the third plate, flexible Tygon tubing was slid down the side channel of the apparatus, with a bevel cut in the leading end of the tubing. The other end was cut, leaving approximately 10 cm protruding from the apparatus. The Plexiglas "filler" sheet was placed over the fifth glass plate. The front half of the apparatus was positioned by aligning the screw holes of the front and back half. These were secured with the teflon screws. The oblong oval "windows" at the lower, front face were sealed with Plastic tape (Scotch brand). The apparatus was stood upright in the lower buffer chamber.

Using a three-way stopcock, the gel apparatus tubing was attached in series with a 2 L reservoir and a 60 ml syringe was attached to the remaining stopcock outlet The tubing was attached to the 2 L reservoir through a bottom drain (a 2 L graduated cylinder was used). The reservoir was secured above the gel apparatus to allow for gravity flow. The stopcock valve was adjusted to allow liquid to flow between the 2 L reservoir and the 60 ml syringe. Once the TEMED was added, the acrylamide solution (1×TBE, pH 8.3, 96.9 g acrylamide, 3.3 g bis-acrylamide, 1.3 g ammonium persulfate and 700 µl TEMED in a total volume of 2 L) was poured into the 2 L reservoir. The syringe plunger was pulled down to the 50 ml mark. The plunger was depressed to push the air out of the upper tubing. Once all air was removed, the valve was adjusted so that all three ports were open. Acrylamide flowed into the apparatus, filling all four gels simultaneously from the bottom upward. The flow was stopped when the level reached 3 mm from the top edge of the glass plates. The solution was allowed to settle for 2 to 3 minutes. After the valve leading to the gel apparatus had been closed, the syringe and reservoir were detached.

The ends of the in-gel digest digest tubing were separated and the first dimension gel was extruded into a pan containing 1×TBE, pH 8.3. The gel was transferred to a 50 ml tube containing 40 ml 1×TBE, pH 8.3. This was incubated for 10 min at room temperature, replaced with fresh TBE, and incubated for an additional 10 min. The first dimension gel was placed in a horizontal position across the beveled edge of each glass plate. Once all gels were in place, the space between the agarose gel and the top of each polyacrylamide gel was filled with molten 0.8% agarose (equilibrated to 55° C.). This connecting agarose was allowed to solidify for 10 to 15 min and then 250 µl second dimension loading dye (1×TE, pH 8.3, 0.25% Bromophenol Blue, 0.25% Xylene Cyanol) was added along the length of each gel. Then 1×TBE, pH 8.3 was added to the upper and lower buffer chambers and electrophoresis was carried out at 100 V for 2 hr and then at 150 V for approximately 24 hr.

Buffers were then removed and the apparatus was disassembled. Each gel was lifted from the plates by overlaying with Whatmann paper cut to size for autoradiographic or phosphorimager cassettes. The perimeter of the paper was traced with the edge of a plastic ruler, removing any excess gel. The Whatmann paper and gel were lifted and placed, gel side up, on a second piece of Whatmann paper. This was overlaid with saran wrap and a third piece of Whatmann paper was added to the top and saran wrap was folded over the top of the Whatmann paper. This was placed in a gel drier, in the same orientation, for 1 hr at 80° C. while applying a vacuum. The lower and upper Whatman paper was then removed, saran wrap folded under the remaining paper and exposed to X-ray film (BioMax MS).

Figure 1B:
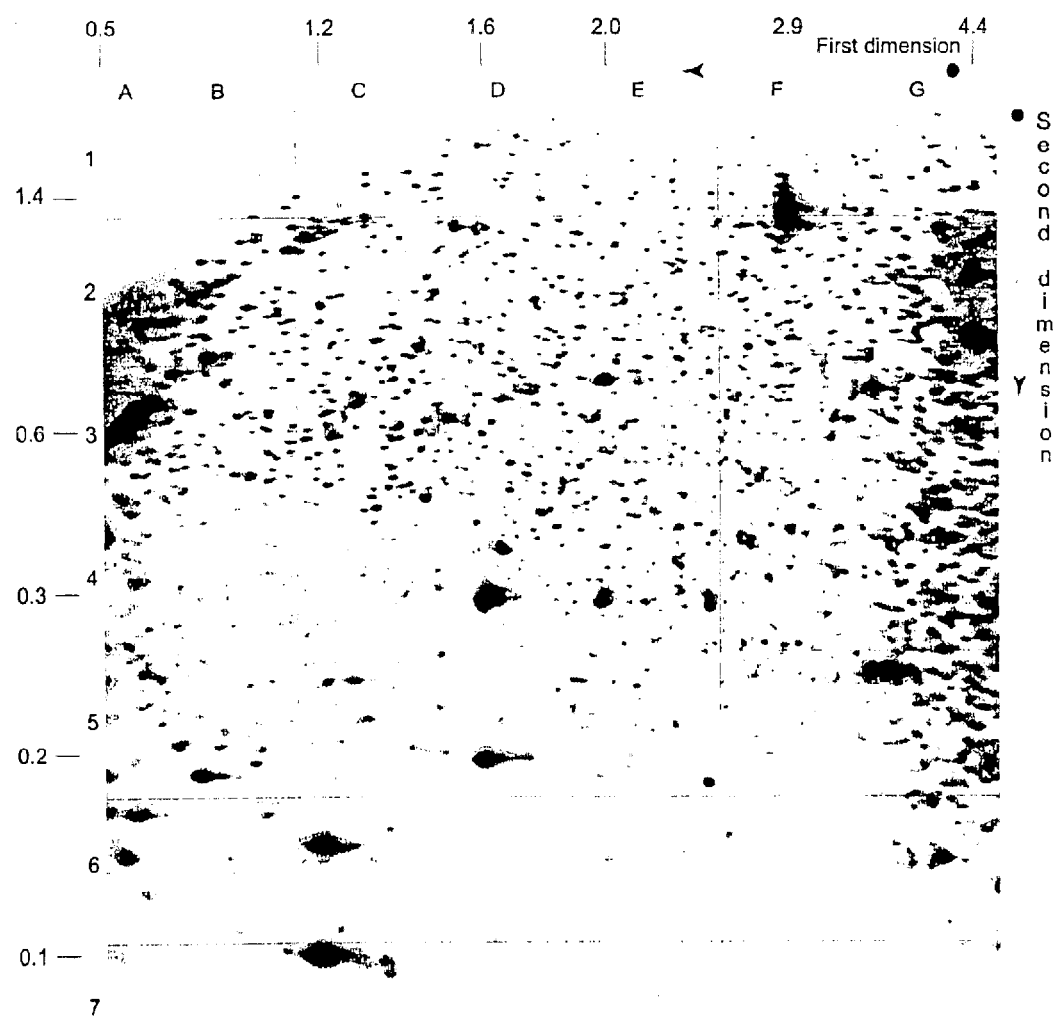
Figure 1C:
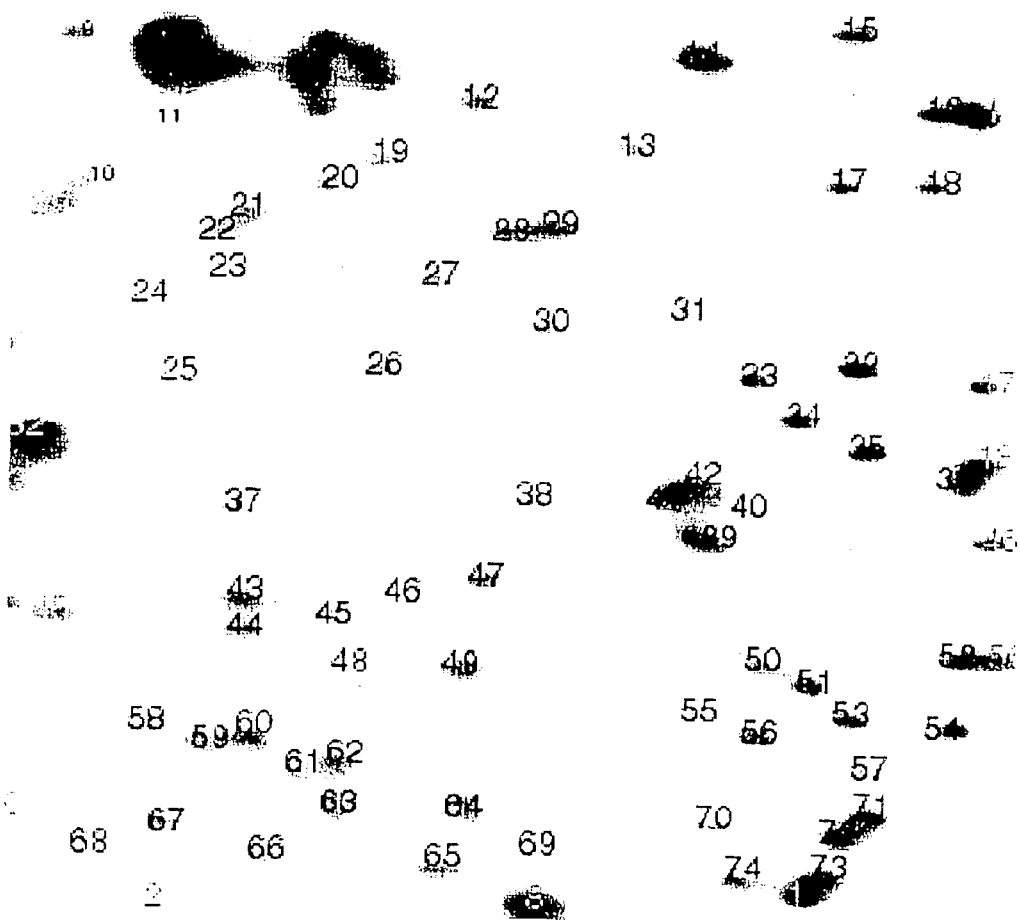

E. RLGS Spots Resulting from Methylation-sensitive Restriction Enzymes Identify CpG Islands Using this methodology, an RLGS profile of DNA from human cells produces a pattern displaying approximately 2,000 spots. FIG. 1B, for example, shows such an RLGS profile from normal peripheral blood lymphocyte DNA. First-dimension separation of labeled NotI/EcoRV fragments extends from right to left horizontally. Following in-gel digestion with HinfI, the fragments were separated vertically downward into a polyacrylamide gel and autoradiographed. To allow uniform comparisons of RLGS profiles, spots were defined based on their location in the gel by assigning each spot a three-variable designation (Y coordinate, X coordinate, fragment number). This can be more easily seen in the enlarged portion of section 2D of the RLGS profile (FIG. 1C) showing the numbers assigned to each spot.

From a set of 1,567 NotI spots comprising the central portion of the RLGS profile of normal DNA, 392 spots were eliminated from all analyses on the basis of having more than diploid intensity, less than diploid intensity, or a degree of positional overlap with neighboring fragments. In addition, a small fraction of loci in individual tumor profiles was not able to be analyzed due to poor local gel quality. In normal DNA profiles, the less-than-diploid copy-number intensities can result from polymorphism, partial methylation or spots derived from sex chromosomes. Thus, the analyzed spots were of diploid copy number in most samples. Tumor tissue and healthy tissue DNA profiles were compared by visual inspection of overlaid autoradiographs. In those cases in which matched normal tissue was not available, tumor profiles were compared with profiles matched for tissue type of four to five unrelated individuals. Each CpG island was defined as unmethylated or methylated (a visually apparent decrease in intensity on the RLGS profile, which, through corroboration with Southern-blot data for 26 CpG island loci and more that 100 loss events, corresponded to a 30% or greater level of methylation).

Figure 1D:
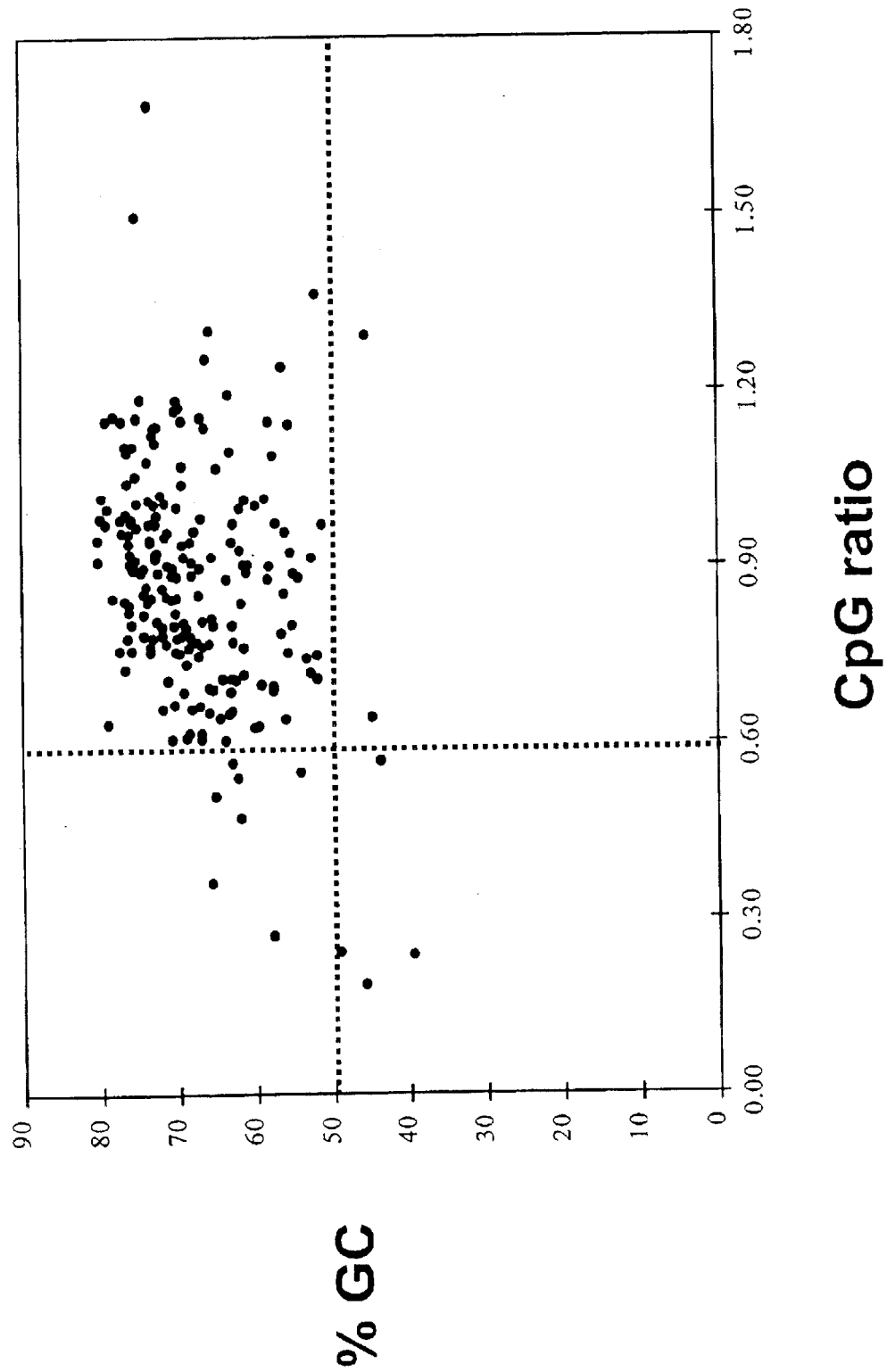

To determine if the NotI restriction sites which produced the RLGS spots, had characteristics of authentic CpG islands, DNA from 210 of the NotI/EcoRV RLGS spots was partially sequenced This was possible because each spot on the human NotI/EcoRV RLGS profile had previously been assigned to a clone from a NotI/EcoRV genomic plasmid library (see description earlier in the specification). Of the 210 spots, 184 were randomly chosen Another 26 spots were chosen because they were frequently lost from RLGS profiles from human tumors, suggesting that cytosine nucleotides within the NotI sequence of that spot were methylated in the tumor. From the sequences derived from these clones, the GC content (%GC) was plotted against the CpG ratio for each clone (FIG. 1D; CpG ratio=[(number of CpGs)/(number of guanines)(number of cytosines)(number of nucleotides analyzed)]). CpG islands have a GC content of greater than 50% and a CpG value of at least 0.6. FIG. 1D shows that, of 210 clones sequenced, 197 (94%) had sequence characteristics consistent with CpG-island DNA.

F. Tumor Tissue Samples Analyzed

DNA used to perform the RLGS analyses was obtained from 98 primary human tumors and, where possible, matched normal samples. These samples were from 8 broad tumor types, breast, colon, gliomas, head and neck, acute myeloid leukemias, primitive neuroectodermal tumors (PNETs) and testicular.

Fourteen breast cancers included 2 adenocarcinomas, 2 lobular carcinomas and 10 ductal carcinomas. The samples were from obtained the Cooperative Human Tissue Network (CHIN). All tumors were from females, 38–89 years of age (average of 54 years). Breast tissue adjacent to the tumor was available for 6 of 14 cases, and 8 tumor profiles were compared with 4 breast samples from the matched sets.

Colon tumors were obtained from Roswell Park Cancer Institute and classified according the American Joint Committee on Cancer staging manual. The 8 primary tumors included 1 stage I tumor, 2 stage II tumors, 2 stage III tumors and 3 stage IV tumors. Patient ages ranged from 49 to 77 years (average of 63 years). Normal adjacent colon mucosa samples were obtained for all tumors.

Fourteen gliomas, including 12 World Health Organization (WHO) grade II astrocytomas and 2 WHO grade III anaplastic astrocytomas, from Saitama Medical School, the University of Tokyo, Teikyo University School of Medicine, Komagome Metropolitan Hospital and the University of Washington, Seattle. Patients included 10 females and 4 males with an age range of 7–57 years (average of 34 years). Brain tissue adjacent to the tumor was also obtained for 1 WHO grade II and 1 WHO grade III tumor. Twelve cases were compared with 3 unmatched normal brain samples and with the 2 brain samples from the matched sets.

Fourteen head and neck squamous cell carcinomas were obtained through the CHTN. Tumors were from 11 males and 3 females. Patients were 42–77 years of age (average of 57 years). Tissue adjacent to the tumor was available for 12 of 14 cases, and 2 tumors were compared with 4 samples from the matched sets.

Nineteen acute myelogenous leukemia samples (3 bone marrow aspirates and 14 peripheral blood) from the Cancer and Leukemia Group B Tissue Bank. Samples were classified according to the French-American-British system. Samples were obtained from patients at the time of initial diagnosis with AML and again at complete remission (24–154 days, average 45 days) after induction chemotherapy. Samples were from 14 males and 3 females. Patients were 22–61 years of age (average 40 years). All cases were compared with matched samples (either peripheral blood lymphocytes or bone marrow, but always matched with the origin of the cancer sample) obtained at remission.

Twenty-two PNETs, including 17 medulloblastomas and 5 supratentorial PNETs, through the CHTN, Pediatric Division. Tumors were from 15 males and 7 females. Patients were 2–26 years of age, with peak ages between 3 and 6 years. All tumors were WHO grade IV. Matched peripheral blood lymphocytes were available for 6 of 22 cases, and 18 samples were compared with unmatched normal cerebellum DNA.

Nine testicular tumors included 6 seminomas and three nonseminomas. Samples were obtained from the Norwegian. Radium Hospital and from the Helsinki University Central Hospital. Patients were 21–77 years (average of 41 years). Adjacent testicular tissue was available for 7 of 9 cases, and 2 samples were compared with 4 samples of testicular DNA used in the matched sets.

G. Loss of Spots from RLGS Profiles is Due to Methylation

Figure 2A:
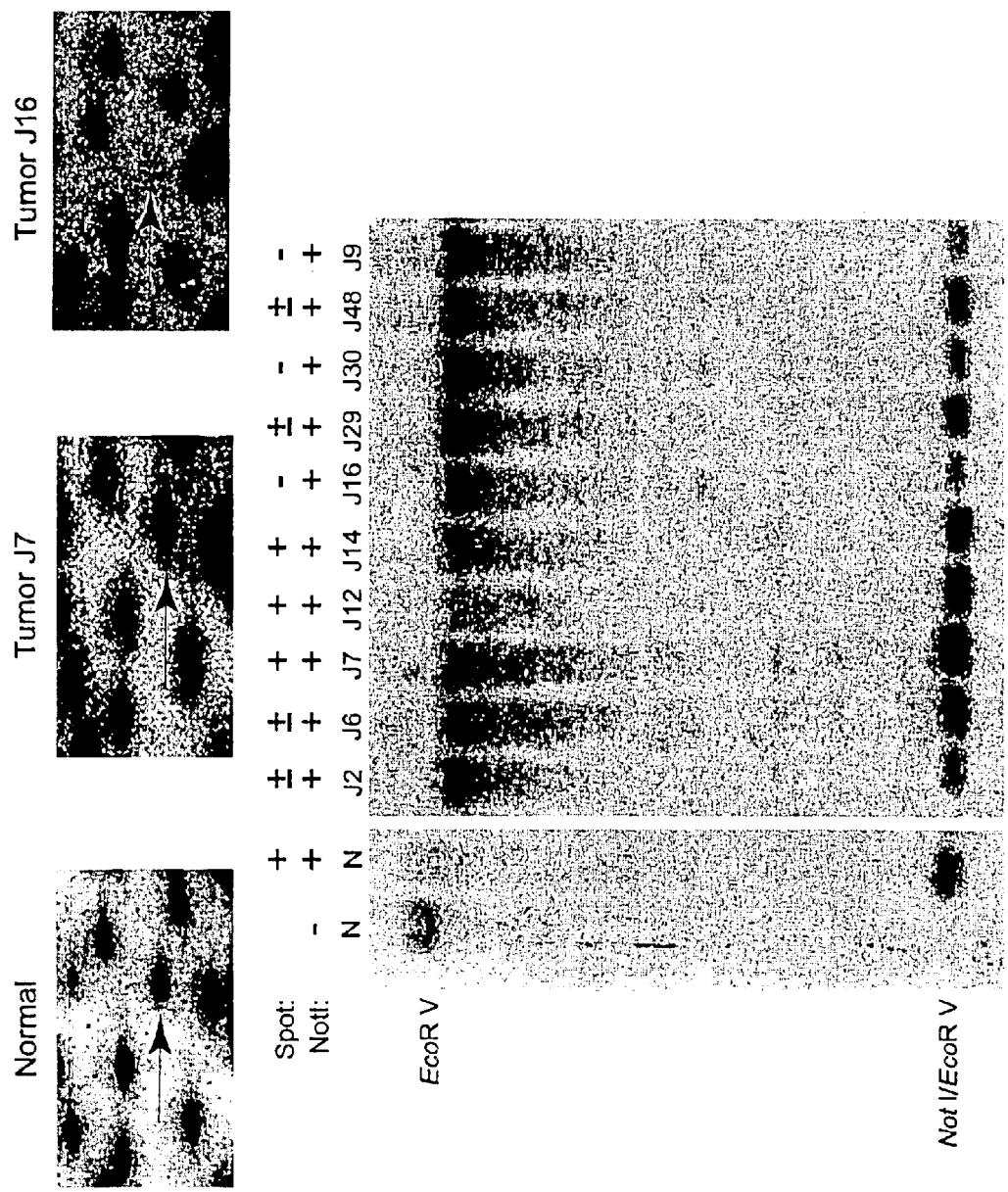
FIG. 2. Fragment loss from RLGS profiles is due to methylation. Top, portions of the RLGS profiles obtained from normal tissue and from two tumors having NotI fragments with either decreased intensity or no change in intensity. Bottom, Southern-blot analysis of EcoRV (NotI: −) and EvoRV/NotI (NotI: +) restriction digested DNAs from a larger number of samples, including the samples at top. In samples without methylation in the NotI site, the probe detects a smaller fragment on double digestion with NotI and EcoRV. The quantitation from multiple Southern blots using a phosphorimager allowed the determination of a lower limit of reliable detection in RLGS profiles of 30% decreased intensity of the diploid NotI/EcoRV fragments. Presence (+) or absence (−) of the corresponding NotI fragment is indicated. N, normal tissue DNA; T, tumor tissue DNA A, CpG-island locus 3C1 methylation in low-grade gliomas. B, CpG island locus 2C40 methylation in leukemias. C, CpG-island locus 3E24 methylation in PNETs of childhood. *, EcoRV fragment of approximately 13 kb with homology to the probe. BLAST searches using the NotI-EcoRV clone sequence identified a homologous BAC clone sequence lacking an internal NotI site, which accounts for the 13-kb fragment on the Southern blot.

In comparing RLGS profiles of DNAs from different tumors with control, healthy tissue DNAs, loss of a fragment or spot from an RLGS profile (FIG. 1A) was frequently detected. Loss of such a spot could be due to either methylation of DNA sequences at the NotI site giving rise to that spot, or to deletion of DNA surrounding that NotI site from the genome of the tumor. The relative contribution of each mechanism was assessed by using clones from the NotI/EcoRV genomic library, specific for lost spots, as probes in Southern blotting studies. In FIG. 2A, a section of an RLGS profile, from normal, healthy tissue was compared with tumor tissue from two gliomas, J7 and J16. This RLGS section contains spot 3C1. In tumor J16, spot 3C1 is absent from the RLGS profile. If there was a deletion of DNA surrounding the NotI site, however, the expected result in the Southern blot would be either no hybridization of the probe to the J16 genomic DNA or hybridization to a band of a size different from those detected in the lane containing normal, healthy tissue DNA digested with NotI plus EcoRV, and tumor tissue DNA digested with EcoRV alone. This result is not seen. These results show, therefore, that DNA corresponding to a missing 3C1 spot in J16 glioma DNA is present in the genome, as shown by the Southern hybridization result.

Likewise, DNA corresponding to specific RLGS spots missing in certain leukemias (FIG. 2B) and neuroectodermal tumors of childhood (FIG. 2C) are found to be present when these DNA are analyzed by Southern blotting. Overall, in 26 tumors where specific spots in RLGS profiles were missing DNA corresponding to the spot, was found to be present in the genome by Southern blotting These results show that loss of spots on RLGS profiles is due to methylation of the corresponding NotI site and not deletion from the genome of DNA representing that spot. Therefore, methylation is the predominant mechanism underlying loss of spots from RLGS profiles.

H. Heterogeneity in CpG-island Methylation Across Tumors.

To compare the overall pattern of methylated CpG islands among different tumors of the same tumor type, 1,184 spots in each of 98 tumors (and their non-tumorigenic controls) were analyzed by RLGS. The analysis was performed by determining the number of RLGS spots lost, or of decreased intensity, as compared to the controls. Each lost spot or spot of decreased intensity is equivalent to one methylated CpG island. For each tumor type, the number of methylated CpG islands in each individual tumor, as compared to controls, was plotted wig 3). These data showed that breast, head and neck, and testicular tumors had relatively low levels of methylation, with many such tumors showing no methylation Colon tumors, gliomas, acute myeloid leukemias and primitive neuroectodermal tumors (PNETs) had a much higher frequency of methylation. Nonparametric comparison (Kruskal-Wallis procedure) of the methylation frequencies of the various tumor types showed significant differences between them ($\chi_6^2 = 56.9$, $P<0.0001$).

Figure 3:
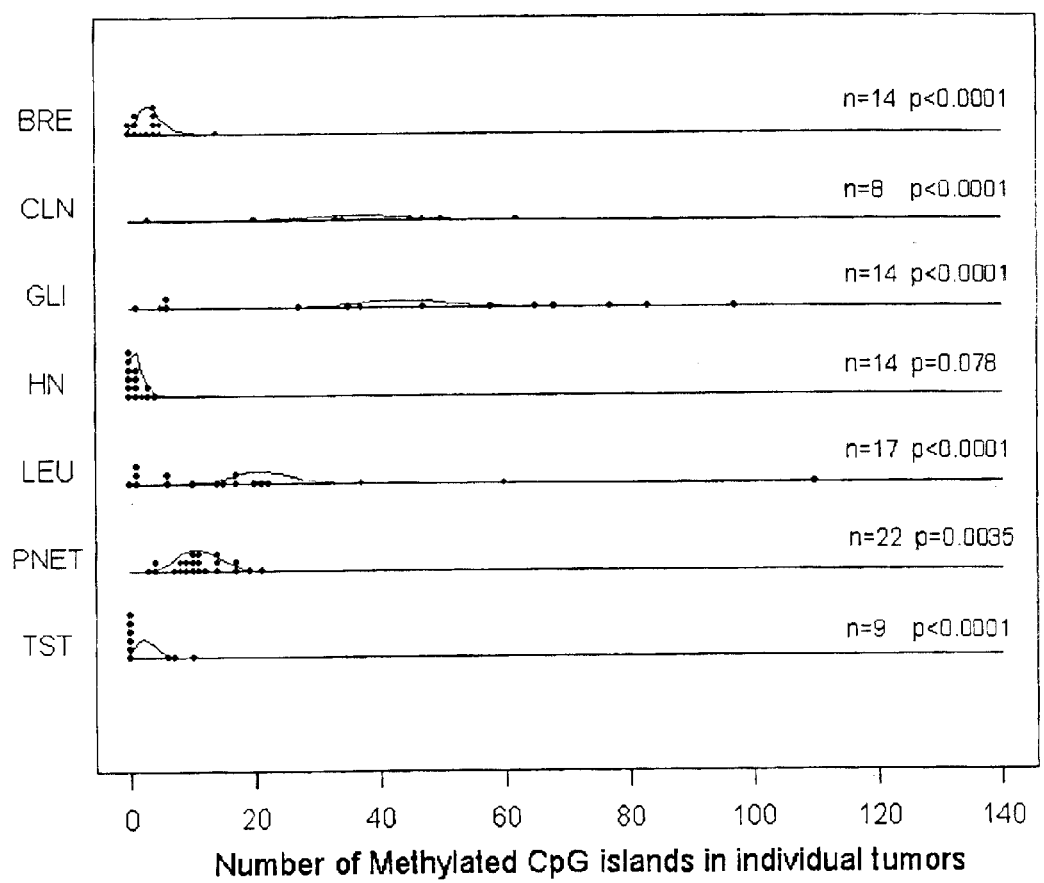
FIG. 3. Heterogeneity in CpG-island methylation across tumors. RAGS profiles w generated from 98 primary human tumors and compared with profiles of either matched normal DNA (58 of 98 cases) or to multiple profiles of tissue typematched normal DNA from unrelated individuals. Loss or decreased intensity of single-copy fragments in the tumors, relative to several neighboring unaltered NotI fragments, were detected by visual inspection of overlaid autoradiographs and confirmed in many cases by independent profiles of the same DNA samples. For each tumor type, the dot plots display the total number of methylated CpG islands (of 1,184 CpG islands analyzed) observed in each tumor. Under the assumption that the tumors are drawn from a homogeneous distribution, with all tumors having the same frequency of methylation, the loss distributions should be approximately Poisson. The colored curve represents the expected distribution. BRE, breast tumors; CLN, colon tumors; GLI, gliomas; HN, bead and neck tumors; LEU, acute mycloid leukemias; PNET, primitive neuroectodermal tumors of childhood; TST, testicular tumors.

Within a tumor type, the range of methylated CpG islands in individual tumors was variable. The data (FIG. 3) are not consistent with chance variation between tumors because, in the absence of heterogeneity, the variance of the methylation frequency would not be expected to be greater than the mean[1]. A formal test of this overdispersion was performed for each tumor type and the results are shown in FIG. 3 as a superimposition of the expected Poisson distribution on the dot plots. These data showed that aberrant methylation of CpG islands can be quantitatively different in individual tumors within a tumor type and more pronounced overall in particular tumor types.

[1]Heterogeneity of methylation frequencies across samples was assessed within each tumor type by a standard test for evidence that the variance in methylation frequency exceeds the mean. This test is motivated by the Poisson approximation, which applies even if the frequencies of methylation vary across CpG islands. Moreover, a simple result from the binomial distribution shows that the test is conservative, because under homogeneity the population variance cannot exceed the mean.

I. Subsets of CpG Islands were Preferentially Methylated in Tumors

Through analysis of the RLGS spots lost in different tumors, it was determined that certain spots on the RLGS gels were lost in multiple tumors. This means that specific CpG dinucleotides were methylated in more than one tumor. This is shown in FIG. 4 where the number of tumors within a specific tumor type that had a particular CpG island methylated are shown.

Figure 4A:
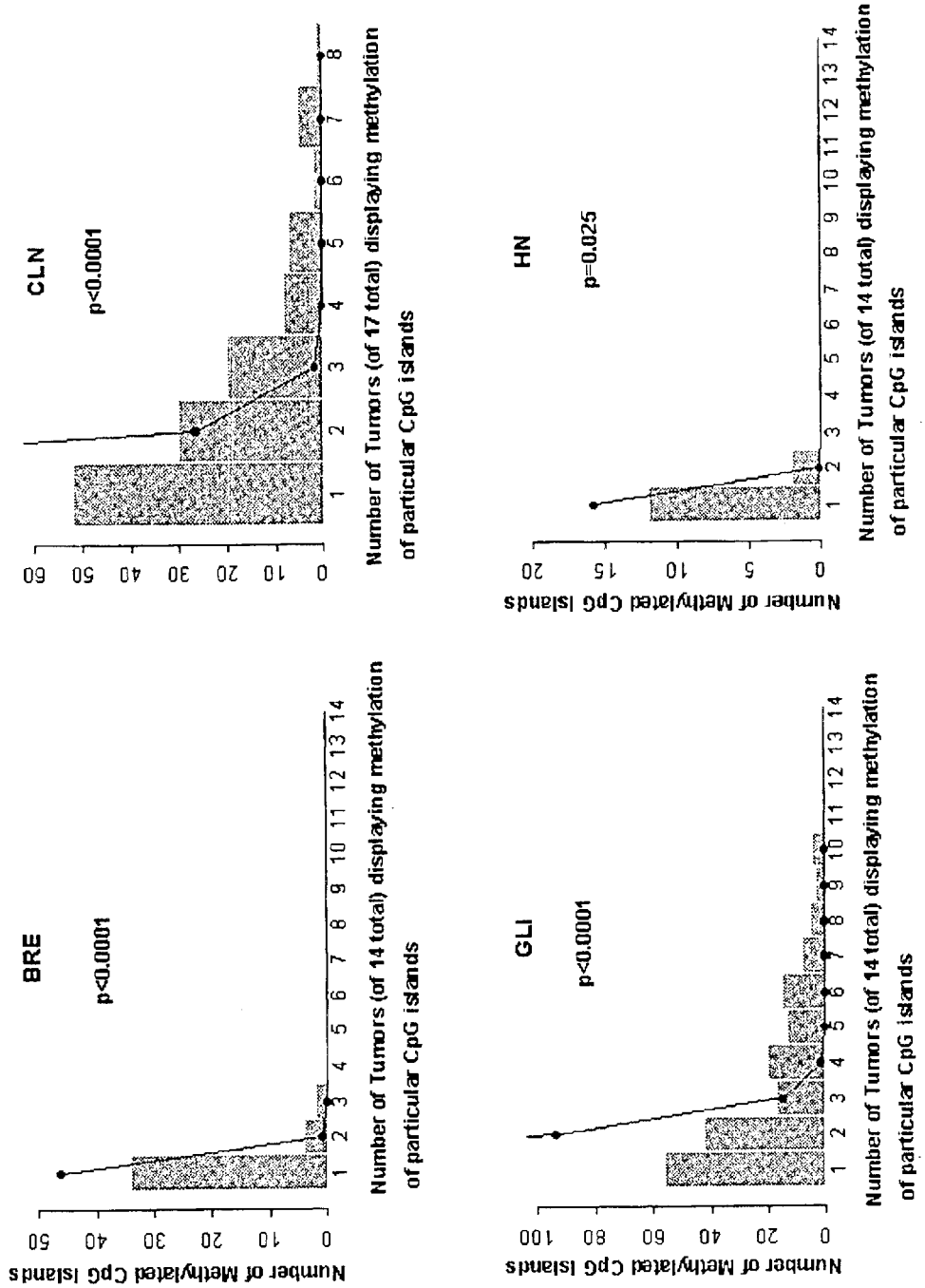
FIG. 4. Subsets of CpG islands are preferentially methylated. For each tumor type, the histograms display the number of tumors in which the particular CpG islands were methylated. Most of the 1,184 CpG islands were not methylated in any of the tumors (histogram bar at 0 is not shown), but several CpG islands were methylated in multiple tumors. The black line shows the expected distribution under the null hypothesis that the CpG islands have equal frequencies of methylation. Most of the tumor types show significant preferential methylation.
Figure 4B:
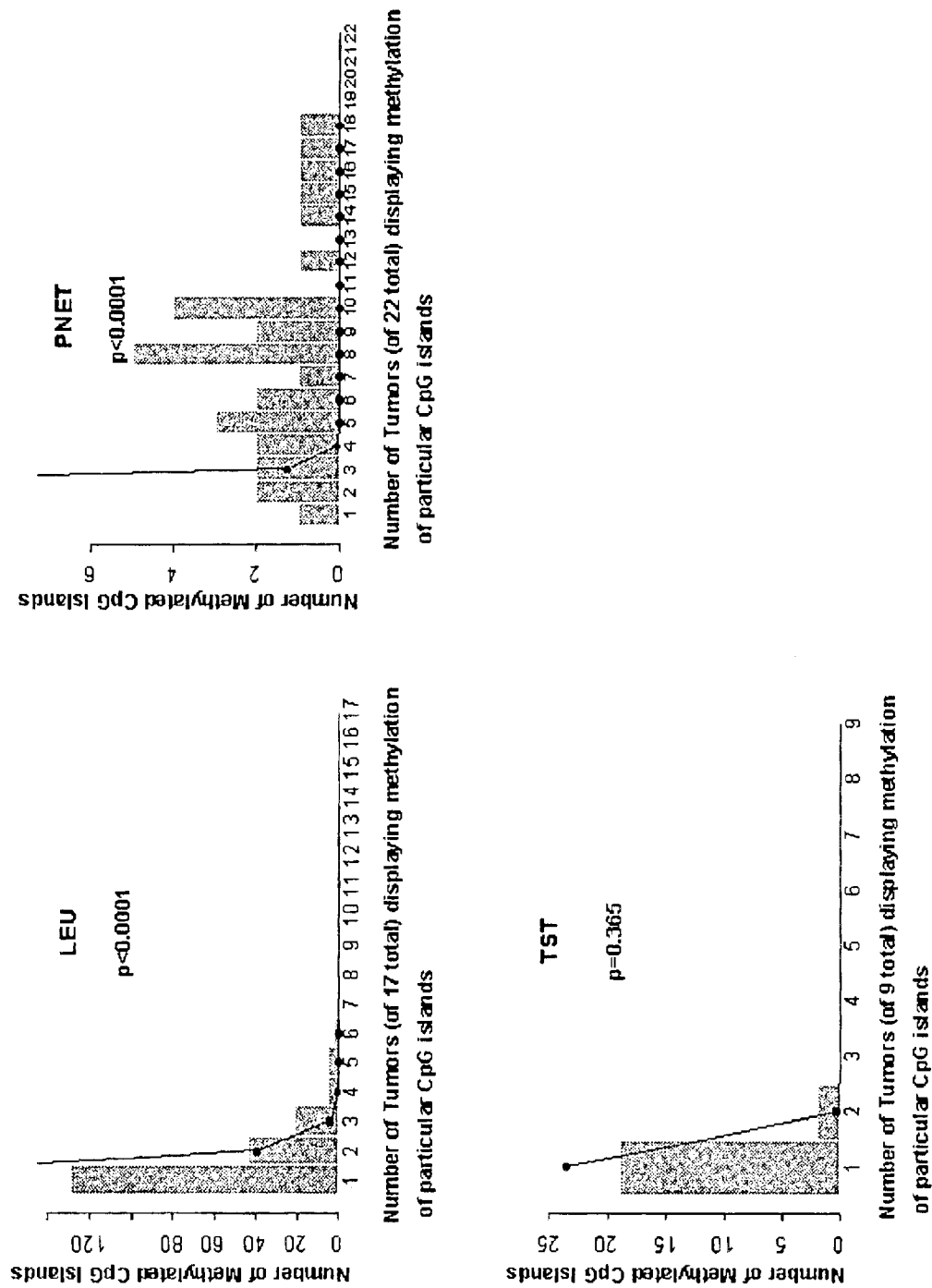

To test the hypothesis that methylation of these common CpG islands was not random, a standard goodness-of-fit test was used.[2] This can be seen in the plots of FIG. 4 where the black

[2]Under the null hypothesis of equal methylation frequencies for each CpG island, a goodness-of-fit test ($\chi^2$) was applied to the observed versus expected frequencies of islands exhibiting line of each plot shows the expected distributions if methylation of specific CpG islands in multiple tumors was random. It can be seen from FIG. 4 that for breast tumors, colon tumors, gliomas, acute myeloid leukemias and childhood PNETs, the actual distributions were significantly different (P<0.0001) from the theoretical distributions indicative of randomness. Similarly, the results for head and neck tumors were significant (P<0.025). The results for testicular tumors (P=0.365) were not significant. However, tumors of this type have a low overall methylation frequency and larger sample sizes are needed. Overall, the data indicate that the patterns of CpG island methylation in tumors is not random.

J. Frequencies of Aberrant CpG-island Methylation of Shared and Tumor-type-specific Targets Because the data have shown that they are methylated in a nonrandom fashion, CpG islands that are methylated at a high frequency in one or more tumor types can be used for diagnosis of tumors. From analysis of 98 tumors using NotI/EcoRV RLGS analysis, a number of spots that are absent or of decreased intensity, as compared to control healthy tissue DNA, have been found. Table I lists these spots. Each fragment (CpG island) is identified in three ways in the table. First, the location of each CpG island is designated as the distance (in cm) migrated during electrophoresis, from the gel origin, in both the first dimension and the second dimension. Second, each CpG island is given a three-variable designation (Y coordinate, X coordinate, fragment number). The X coordinate indicates horizontal direction on the two-dimensional RLGS profile and is a letter from B–G. The Y coordinate indicates vertical direction and is a number from 1–5. Together, an X and Y designation divide the RLGS profile into 28 sections. Within each section, the spots/fragments are given a number. Such a profile is available via the internet at <URL: pandora.med.ohio-state.edu/masterRLGS/>. Third, the partial DNA sequence of individual spots has been determined by sequencing of library clones corresponding to each spot These sequences are shown in the attached Sequence Listing and have been assigned SEQ ID NOS. from 1 to 82.

The diagnostic NotI/EcoRV spots are of two types (FIG. 1). The first type of spot is absent or of decreased intensity in a single tumor type. For example, the NotI site that is part of the CpG island designated 2.B.53, is methylated only in head and neck tumors. Similarly, the NotI site of CpG island 2.F.2 is methylated only in breast tumors. methylation in multiple tumors within each tumor type.

The second type of spot is absent or of decreased intensity in more than one type of tumor. For example, the NotI/EcoRV spot designated 2.C.24 is missing in gliomas and AMLs. Similarly, the NotI/EcoRV spot designated 3.B.55 is methylated in breast, colon and PNETs.

TABLE I

Diagnostic CpG islands in tumors.

| CpG Island[1] | 1st-D (cm)[2] | 2nd-D (cm)[2] | Type[3] | Methylated In[4]: |
|---|---|---|---|---|
| 2.B.53 | 36.85 | 9.25 | t | HN |
| 2.C.24 | 30.3 | 5.32 | s | Abt/Leu |
| 2.C.29 | 27.8 | 5.45 | s | Leu/Hn |
| 2.C.35 | 29.45 | 6.9 | s | Abt/Bre/Cln/Leu/Pbt |
| 2.C.54 | 32.38 | 9.42 | s | Leu/Hn |
| 2.C.57 | 30.9 | 8.5 | ND | Tst |
| 2.C.58 | 31.2 | 9.2 | s | Abt/Leu |
| 2.C.59 | 30.4 | 9.35 | ND | Hn |
| 2.D.10 | 27.55 | 5.3 | s | Leu/Pbt |
| 2.D.14 | 24.25 | 4.47 | t | Leu |
| 2.D.20 | 26.3 | 5.3 | t | Cln |
| 2.D.25 | 27.15 | 6.4 | ND | Bre |
| 2.D.27 | 25.65 | 5.82 | ND | Hn |
| 2.D.34 | 23.62 | 6.6 | s | Leu/Pbt |
| 2.D.40 | 23.95 | 7.25 | ND | Pbt |
| 2.D.48 | 26.1 | 8.1 | ND | Leu |
| 2.D.55 | 24.2 | 8.3 | s | Cln/Leu |
| 2.D.74 | 23.95 | 9.35 | s | Abt/Bre/Cln/Leu |
| 2.E.20 | 20.6 | 5.95 | ND | Pbt |
| 2.E.24 | 19.35 | 5.7 | s | Abt/Leu |
| 2.E.25 | 18.27 | 5.65 | t | Bre |
| 2.E.30 | 20.35 | 6.4 | s | Abt/Bre/Leu |
| 2.E.37 | 21.42 | 7.1 | ND | Bre |
| 2.E.4 | 21.1 | 4.48 | s | Leu/Pbt |

TABLE I-continued

Diagnostic CpG islands in tumors.

| CpG Island[1] | 1st-D (cm)[2] | 2nd-D (cm)[2] | Type[3] | Methylated In[4]: |
|---|---|---|---|---|
| 2.E.40 | NA | NA | ND | Tst |
| 2.E.61 | 19.4 | 8.08 | s | Abt/Pbt |
| 2.E.64 | 20.5 | 8.35 | s | Abt/Cln |
| 2.F.2 | 17.27 | 4.72 | t | Bre |
| 2.F.41 | NA | NA | t | Tst |
| 2.F.50 | 15.23 | 7 | s | Abt/Leu |
| 2.F.59 | 17.49 | 8 | ND | Bre |
| 2.F.70 | 15.88 | 13.3 | s | Pbt/Tst |
| 2.G.10 | 10.29 | 4.49 | s | Leu/Tst |
| 2.G.108 | 7.68 | 7.44 | ND | Bre |
| 3.B.30 | 35.4 | 12.55 | ND | Tst |
| 3.B.36 | 34.2 | 11.8 | s | Abt/Cln/Leu/Pbt |
| 3.B.55 | NA | NA | s | Bre/Cln/Pbt |
| 3.C.01 | 31.6 | 9.7 | s | Abt/Cln/Leu |
| 3.C.16 | 27.9 | 11.8 | t | Pbt |
| 3.C.17 | 29.2 | 10.57 | t | Cln |
| 3.C.30 | 31.61 | 10.37 | t | Bre |
| 3.C.35 | 31.6 | 11.5 | t | Pbt |
| 3.C.64 | 29.1 | 14.05 | ND | Bre |
| 3.D.21 | 24.2 | 10.75 | t | Leu |
| 3.D.24 | 23.2 | 11.03 | s | Abt/Leu |
| 3.D.35 | 26.1 | 11.65 | s | Abt/Cln/Leu/Pbt |
| 3.D.40 | 23.4 | 12.26 | s | Abt/Cln/Leu |
| 3.D.44 | 24.45 | 12.82 | t | Leu |
| 3.D.60 | 27.2 | 12.4 | s | Abt/Cln/Leu |
| 3.E.04 | 20.4 | 14.2 | s | Hn/Pbt |
| 3.E.50 | 20.55 | 10.7 | s | Hn/Tst |
| 3.E.55 | 18.78 | 10.55 | s | Cln/Leu |
| 3.E.57 | 18.09 | 10.9 | s | Cln/Hn |
| 3.E.59 | 18.4 | 9.72 | s | Abt/Tst |
| 3.F.16 | 16.6 | 9.75 | ND | Leu |
| 3.F.2 | 16.73 | 9.35 | s | Leu/Tst |
| 3.F.50 | 16.25 | 11.6 | s | Cln/Leu/Tst |
| 3.F.72 | 16.9 | 13.7 | t | Leu |
| 3.F.82 | 13.8 | 13.12 | s | Abt/Cln/Leu |
| 3.G.46 | 9.88 | 11.5 | ND | Bre |
| 3.G.78 | 10 | 12.93 | ND | Leu/Pbt |
| 4.B.44 | 33.7 | 18.53 | s | Cln/Hn |
| 4.B.56 | 33.2 | 19.45 | s | Bre/Leu |
| 4.C.05 | 30 | 14.9 | ND | Bre |
| 4.C.25 | 28.62 | 17 | ND | Bre |
| 4.C.42 | NA | NA | ND | Tst |
| 4.C.9 | 30.3 | 15.3 | ND | Bre |
| 4.D.07 | 22.9 | 14.5 | s | Leu/Tst |
| 4.D.08 | 23.5 | 15 | s | Abt/Tst |
| 4.D.12 | 25 | 14.85 | s | Abt/Leu/Tst |
| 4.D.13 | 24.95 | 15.3 | s | Abt/Bre |
| 4.D.47 | 27.6 | 18.25 | s | Abt/Leu/Pbt |
| 4.E.53 | 19.39 | 18.43 | t | Leu |
| 4.F.15 | 13.25 | 15.45 | t | Cln |
| 4.F.17 | 14.1 | 15.6 | s | Abt/Bre/Cln |
| 4.F.22 | 17.56 | 16.2 | s | Cln/Hn/Leu |
| 4.F.6 | 14.85 | 14.59 | ND | Bre |
| 4.F.69 | 12.58 | 18.86 | t | Abt |
| 5.D.9 | 25.17 | 23.4 | t | Hn |
| 5.E.2 | 20.58 | 19.5 | t | Bre |
| 5.E.25 | 18.7 | 21.3 | t | Cln |
| 5.E.4 | 18.45 | 19.75 | s | Abt/Bre/Leu |

[1]Y coordinate, X coordinate, fragment number
[2]NA, spots too close to analyze.
[3]T, tumor-type specific target of methylation; s, shared target of methylation; ND, not determined.
[4]Types of tumor in which CpG island is methylated: Abt, gliomas; Bre, breast; Cln, colon; Hn, head and neck; Leu, acute myeloid leukemia; Pbt, pediatric brain tumors; Tst, testicular germ cell tumors.

Example 2

Identification of Diagnostic Markers for Lung Cancer Using AscI and RLGS

Tissue from lung tumors was obtained as surgical tissue samples. Where possible, surrounding non-tumor tissue from the same patient was obtained and used as a control. DNA was isolated from the tissue as described in Example 1. In preparation for RLGS analysis, the ends of the DNA were blocked as described in Example 1. The DNA was then digested with AscI followed by digestion with EcoRV. The AscI restriction enzyme recognizes the sequence 5'GGCGCGCC3' and does not cleave said sequence if cytosines within the sequence are methylated. First dimension gel electrophoresis, in-gel digestion with HinfI, second dimension gel electrophoresis and autoradiography were performed as described in Example 1.

RLGS profiles from lung tumor DNA were compared with RLGS profiles obtained from healthy, non-tumor tissue DNA. Spots which were lost or present at reduced intensity in tumor tissue RLGS profiles as compared to profiles obtained from healthy tissue were noted. Eight spots were lost or altered in the RLGS profiles from multiple lung tumor samples. A compilation of such spots is shown in Table II (lung tumors).

DNA sequence information was obtained from the lung cancer-specific spots. This was done by sequencing individual clones of an AscI/EcoRV library that was made from DNA from healthy tissue. Individual clones of this library that corresponded to spots on the AscI/EcoRV RLGS profile were identified by overloading an RLGS gel with DNA from various groups of library clones, as was described earlier in the specification of this application for the NotI/EcoRV library. After individual clones were matched with spots in the AscI/EcoRV profile, the DNA from the spots that were missing in profiles from the lung tumor DNAs were sequenced. Such sequence information is shown in the attached DNA Sequence Listing.

TABLE II

Diagnostic CpG islands grouped by tumor type.

| Library | Tumor type | Tumor type specific (+), shared (−), or not determined (ND)[1] | CpG island designation |
|---|---|---|---|
| NotI/EcoRV | Breast | + | 2.E.25, 2.F.2, 3.C.30, 5.E.2 |
| | | − | 3.B.55, 4.B.56, 4.D.13, 4.F.17, 2.D.74, 2.C.35, 2.E.30, 5.E.4 |
| | | ND | 2.D.25, 2.E.37, 2.F.59, 2.G.108, 3.C.64, 3.G.46, 4.C.05, 4.C.25, 4.C.9, 4.F.6 |
| NotI/EcoRV | Colon | + | 2.D.20, 3.C.17, 4.F.15, 5.E.25 |
| | | − | 3.E.57, 4.B.44, 4.F.22, 2.D.55, 3.E.55, 3.F.50, 3.B.55, 4.F.17, 2.D.74, 2.C.35, 2.E.64, 3.C.01, 3.D.40, 3.D.60, 3.F.82, 3.B.36, 3.D.35 |
| | | ND | — |
| NotI/EcoRV | Glioma | + | 4.F.69 |
| | | − | 4.D.13, 4.F.17, 2.D.74, 2.C.35, 2.E.30, 5.E.4, 2.E.64, 3.C.01, 3.D.40, 3.D.60, 3.F.82, 3.B.36, 3.D.35, 2.C.24, 2.C.58, 2.E.24, 2.F.50, 3.D.24, 4.D.47, 4.D.12, 2.E.61, 3.E.59, 4.D.08 |
| | | ND | — |

TABLE II-continued

Diagnostic CpG islands grouped by tumor type.

| Library | Tumor type | Tumor type specific (+), shared (−), or not determined (ND)[1] | CpG island designation |
|---|---|---|---|
| NotI/EcoRV | Head & neck | + | 2.B.53, 5.D.9 |
| | | − | 2.C.29, 2.C.54, 3.E.04, 3.E.50, 3.E.57, 4.B.44, 4.F.22 |
| | | ND | 2.C.59, 2.D.27 |
| NotI/EcoRV | Acute myelogenous Leukemia | + | 2.D.14, 3.D.21, 3.D.44, 3.F.72, 4.E.53, 2.C.29, 2.C.54 |
| | | − | 2.D.10, 2.D.34, 2.E.4, 2.G.10, 3.F.2, 4.D.07, 4.F.22, 2.D.55, 3.E.55, 3.F.50, 2.E.64, 3.C.01, 3.D.40, 3.D.60, 3.F.82, 3.B.36, 3.D.35, 3.C.01, 3.D.40, 3.D.60, 3.F.82, 3.B.36, 3.D.35, 2.C.24, 2.C.58, 2.E.24, 2.F.50, 3.D.24, 4.D.47, 4.D.12 |
| | | ND | 2.D.48, 3.F.16, 3.G.78, 4.B.56 |
| NotI/EcoRV | Pediatric neuroectodermal tumor of childhood | + | 3.C.16, 3.C.35, 3.E.04 |
| | | − | 2.D.10, 2.D.34, 2.E.4, 3.B.55, 2.C.35, 3.B.36, 3.D.35, 4.D.47, 2.E.61 |
| | | ND | 2.D.40, 2.E.20, 3.G.78 |
| NotI/EcoRV | Testicular | + | 2.F.41 |
| | | − | 2.G.10, 3.F.2, 4.D.07, 3.E.50, 3.F.50, 4.D.12, 3.E.59, 4.D.08 |
| | | ND | 2.C.57, 2.E.40, 3.B.30, 4.C.42 |
| AscI/EcoRV | Lung | + | |
| | | − | |
| | | ND | A.2.F.45, A.2.F.50, A.2.F.67, A.3.F.38, A.4.D.30, A.4.D.36, A.4.E.32, A.5.E.28[2] |

[1]ND, not determined. Indicates that the designated CpG island was methylated in the indicated tumor type but its methylation in other tumor types was not determined.
[2]The "A" preceding the X, Y, number designation for the CpG islands indicates that these islands are from the AscI/EcoRV RLGS profile.

Example 3

Design of Primers for Cancer Diagnosis

Primers are designed for diagnosis of cancer using methylation-specific PCR (MSR). The primers are designed to amplify regions of the human genome whose sequences are contained within the library clones disclosed in this application. Two sets of primers are needed for each library clone whose DNA sequence is to be used for diagnosis of cancer. Each primer set is designed to amplify the same region of the genome, said region beginning at the end of a library clone containing the methylation-sensitive restriction enzyme recognition site (i.e., the NotI site for the library described in Example 1; the AscI site for the library described in Example 2) and ending at a region contained within the clone up to 200 nucleotides from the methylation-sensitive restriction enzyme recognition site.

The first set of primers is designed to amplify template genome DNA whose cytosine residues are not methylated and, after bisulfite treatment, the cytosines of said genome DNA are converted to uracil. The second set of primers is designed to amplify template genome DNA which is methylated on cytosines that comprise CpG dinucleotides. Such methylated cytosines are unaffected by bisulfite treatment. Therefore, by using two sets of primers, one set that will amplify only unmethylated DNA and another set that will amplify only methylated DNA, methylation state of the template DNA can be determined. Such methylation state can be diagnostic for cancer.

The primers used for MSR are designed to be from 15 to 34 nucleotides in length and contain within their sequence either CpG dinucleotides or dinucleotides complementary to CpG dinucleotides that have been ted with bisulfite. It is preferred that the 3' ends of primers used to amplify unmethylated DNA are CpA dinucleotides. It is preferred that the 3' ends of primers used to amplify methylated DNA are CpG dinucleotides.

For each library clone to be used diagnostically, the first set of primers are designed to amplify genome DNA that is not methylated. After treatment of such genome DNA with bisulfite, all such unmethylated cytosines are converted to uracil. PCR primers that will use such DNA as a template and amplify it, win have adenine residues which are complimentary to these uracils.

For the first set of primers, the 5' end of one of the primers begins at the end of the library clone containing the methylation-sensitive restriction enzyme recognition site. The sequence of this primer is identical in sequence to the strand of the template which has its 5' end as part of the methylation-sensitive restriction enzyme site, except that guanine residues are replaced with adenine residues. The adenines allow the primer to hybridize with the template strand in which cytosines have been converted to uracils by bisulfite. This primer extends to a length of between 15 and 32 total nucleotides. Preferably, the 3' end of said primer ends with a CpA dinucleotide, the adenine of said dinucleotide hybridizing to a uracil which, before bisulfite treatment, bad been a cytosine that comprised a CpG dinucleotide.

The diagram below shows implementation of these rules to select a primer that can be used to amplify clone 2.B.53 of the NotI/EcoRV library (Table I and attached sequence listing). In the diagram, I shows the end of the 2.B.53 clone containing the methylation-sensitive NotI site (NotI recognition sequence is shown in bold letters). CpG dinucleotides are shaded. To amplify a region of this clone rightward of the NotI site, the first primer is identical to the top stand of the duplex shown in I. However, since bisulfite treatment of the DNA in I converts cytosines to uracils, guanines within the PCR primer must be replaced with adenines. II shows the sequence of the bottom stud of I after bisulfite treatment converts cytosines to uracils. A primer complementary to the bisulfite-treated bottom strand has the sequence shown in III.

```
I
5'GCGGCCGCGGTTAGCTTCTCCTGTCCGAACGCAGGG-----
3'CGCCGGCGCCAATCGAAGAGGACAGGCTTGCGTCCC-----

II
3'UGUUGGUGUUAATUGAAGAGGAUAGGUTTGUGTUUU-----

III
5'ACAACCACAATTAACTTCTCCTATCCAAACA 3'
```

III shows the entire sequence of one of the two primers used to amplify unmethylated genome DNA corresponding to library clone 2.B.53. This primer encompasses S CpG dinuceotides, as shown by the shading in I above. Encompassment of 2 or more such CpG dinucleotides is preferred so that this primer will not hybridize to a bisulfite-treated template which contains methylated cytoines. The 3' end of the primer shown in III ends in a CpA dinucleotide. This is also preferred in order to provide maxima discrimination of the primer between methylated and unmethylated template DNA in MSR. The primer shown in III has a length of 31 nucleotides.

The second primer is designed to work with the first primer in PCR amplification such that a fragment of less than about 200 base pairs is amplified. Therefore, this primer is made to a sequence rightward of the sequence shown in I. The sequence of this primer is complementary in sequence to the stand of the template which has its 5' end as part of the methylation-sensitive restriction enzyme site, except that guanine residues arc replaced with adenine residues. This primer is preferably between 15 and 32 nucleotides in length This primer is also designed to preferably encompass 2 or more CpG dinucleotides. Preferably, the 3' end of said primer ends with a CpA dinucleotide.

The diagram below shows implementation of these rules to select a primer that can be used to amplify unmethylated genome DNA corresponding to clone 2.B.53 of the NotI/EcoRV library. IV shows a region of the 2.B.53 clone about 70 nucleotides rightward of the sequence in I of the earlier diagram. The CpG dinucleotides within the sequence are shaded. To amplify a region leftward of this region, this second primer must be complementary to the top strand of the duplex shown in IV. However, bisulfite treatment of the DNA in IV converts cytosines to uracils. A primer complementary to this bisulfite-treated top strand has the sequence shown in VI.

```
IV
5'-----GGAGTCGCCGTCGCCGGAGGCTGCGCCGCGCACCGA-----3'
3'-----CCTCAGCGCCAGCGCCCTCCGACGCGGCGCGTGGCT-----5'

V
5'-----GGAGTUGUGGTUGUGGGAGGUTGUGUUGUGUAUUGA-----3'

VI
           3' ACACCAACACCCTCCAACACAACACATAACT 5'
```

VI shows the entire sequence of the second primer used to amplify unmethylated genome DNA corresponding to library clone 2.B.53. This primer encompasses 8 CpG dinucleotides, as shown by the shading in IV. Encompassment of 2 or more such CpG dinucleotides is preferred. The 3' end of the primer shown in VI ends in a CpA dinucleotide. This is also preferred. The primer shown in VI has a length of 31 nucleotides. Together, the first and second primers amplify a PCR fragment of 128 base pairs in length.

The above primers amplify genome DNA that does not contain 5-methylcytosine. The above primers will not amplify genome DNA containing 5-methylcytosines because 5-methylcytosines are not converted to uracils by bisulfite treatment. The two primers already described (III and VI), therefore, will not be complementary to bisulfite-treated genome DNA which is methylated.

Therefore, a second set of primers is designed to amplify genome DNA that is methylated. Methylation in human cells occurs at cytosines that are part of CpG residues, Such methylated cytosines arc not converted to uracil by bisulfite treatment. Cytosines that are not part of CpG residues are not methylated and, therefore, are converted to uracil by bisulfite. The primers of the second set are designed to amplify the same region of a library clone as did the first set of primers. But, because the genome DNA contains both cytosines that are methylated and cytosines that are not methylated, the sequences of primers used to amplify such DNA are different than the sequences of the first primer set. Like the first set of primers, however, the primers of the second set are preferably between 15 and 32 nucleotides in length. Preferably the 3' ends of such primers contain CpG dinucleotides.

The diagram below shows implementation of these rules to select the first of two primers that can be used to amplify methylated genomic DNA corresponding to clone 2.B.53 of the NotI/EcoRV library. In the diagram below, VII shows the end of the 2.B.53 clone containing the NotI site (NotI recognition sequence is bolded). CpG dinucleotides are shaded. Cytosines within said CpG dinucleotides are methylated and are underlined in VII to indicate methylation to 5-methylcytosine. Treatment of the DNA in VII with bisulfite produces a bottom strand with the sequence shown in VIII. In VIII, only unmethylated cytosines are converted to uracil by bisulfite.

```
VII
5'GCGGCCGCGGTTAGCTTCTCCTGTCCGAACGCAGGG-----
3'CGCCGGCGCCAATCGAAGAGGACAGGCTTGCGTCCC-----

VIII
3'UGCUGGCGCUAATUGAAGAGGAUAGGCTTGCGTUUU-----

IX
5'ACGACCGCGATTAACTTCTCCTATCCGAACG 3'
```

A primer complementary to the bisulfite-treated bottom strand shown in VIII is shown in IX. Said primer will prime PCR amplification of sequences rightward of those shown in VII. The primer shown in IX encompasses 5 CpG dinucleotides. Encompassment of 2 or more such CpG dinucleotides is preferred. The 3' end of the primer shown in IX ends in CpG. This is also preferred. The primer shown in IX has a length of 31 nucleotides.

A second primer is designed to work with the primer shown in IX to amplify methylated genome template DNA. Design of such a primer is shown below. In the diagram, X shows the same region of clone 2.B.53 (approximately 70 nucleotides rightward of the sequences shown in VII) that is shown in IV. Treatment of the DNA in X with bisulfite produces a top strand with the sequence shown in XI. In XI, only unmethylated cytosines are converted to uracil by bisulfite.

```
X
5'-----GGAGTCGCGGTCGCGGGAGGCTGCGCCGCGCACCGA-----3'
3'-----CCTCAGCGCCAGCGCCCTCCGACGCGGCGCGTGGCT-----5'

XI
5'-----GGAGTCGCGGTCGCGGGAGGTGCGUCGCGUAUCGA------3'

XII
           3' GCGCCAGCGCCCTCCAACGCAGCGCATAGCT 5'
```

A primer complementary to the bisulfite-treated top strand (XI) has the sequence shown in XII. Said primer will prime PCR amplification of sequences leftward of those shown in X. The primer shown in XII encompasses 8 CpG dinucleotides. Encompassment of 2 or more such CpG dinucleotides is preferred. The 3' end of the primer shown in XII ends in a CpG dinucleotide. This is also preferred. The primer shown in XII has a length of 31 nucleotides. Together, the first (IX) and second primers (XII) of the second set amplify a PCR fragment of 128 base pairs in length.

Example 4

Use of Oligonucleotides to Diagnose Cancer

The library clones, and DNA sequences within, can be used to detect DNA methylation in a genome at the specific sequences identified by the sequences within the clone. Such detection can be diagnostic for cancer. Various methods can be used for such diagnosis.

A. Diagnosis of Cancer Using Methylation-sensitive Restriction Enzymes Followed by Southern Blot Cleavage or lack of cleavage by a methylation-sensitive restriction enzyme at a specific restriction enzyme recognition site can be detected by a probe for the specific recognition site, using Southern blotting. Genomic DNAs were isolated (as described in Example 1) from tumor tissue from a patient with acute myelogenous leukemia (AML). Cells from the same patient after chemotherapy and remission of the disease served as a source of control, healthy tissue DNA. The AML and control DNAs were designated as 26T and 26N, respectively. The DNAs were digested with NotI and EcoRV for 4 hours and then electrophoresed through a 0.8% agarose gel. DNA within the gel was depurinated by soaking the gel in 0.2 N HCl for 10 min. The gel was equilibrated in transfer solution (0.5 N NaOH, 1 M NaCl) for 10 min and then blotted to Zeta Bind-GT nylon membranes (Bio-Rad). Blots were crosslinked with UV light, baked in a vacuum oven and then prehybridized for 1 hour at 65° C. in a solution of 7% SDS, 500 mM sodium phosphate buffer (pH 7.2) and 1 mM EDTA. The blot was hybridized overnight at 65° C. in prehybridization solution with 10 ng of $\alpha$-$^{32}$P-labeled probe at a specific activity of $10^8$–$10^9$ dpm/$\mu$g. The DNA probe used was the 2.C.40 clone from the NotI/EcoRV 2.C.40 library. The purified NotI/EcoRV fragment (50 ng) was labeled with [$\alpha^{32}$P]dCTP by random priming using the Prime-It II random-prime labeling kit (Stratagene). The blot was washed with two quick rinses at 65° C. in wash solution 1 (100 mM sodium phosphate buffer, pH 7.2, 0.1% SDS), followed by one 30 min. wash at 65° C. in wash solution 1. The blot was next washed for 30 min. at 65° C. in wash solution 2 (40 mM sodium phosphate buffer, pH 7.2, 0.1% SDS). Bands were visualized by autoradiography using Kodak X-OMAT AR film.

Figure 2B:
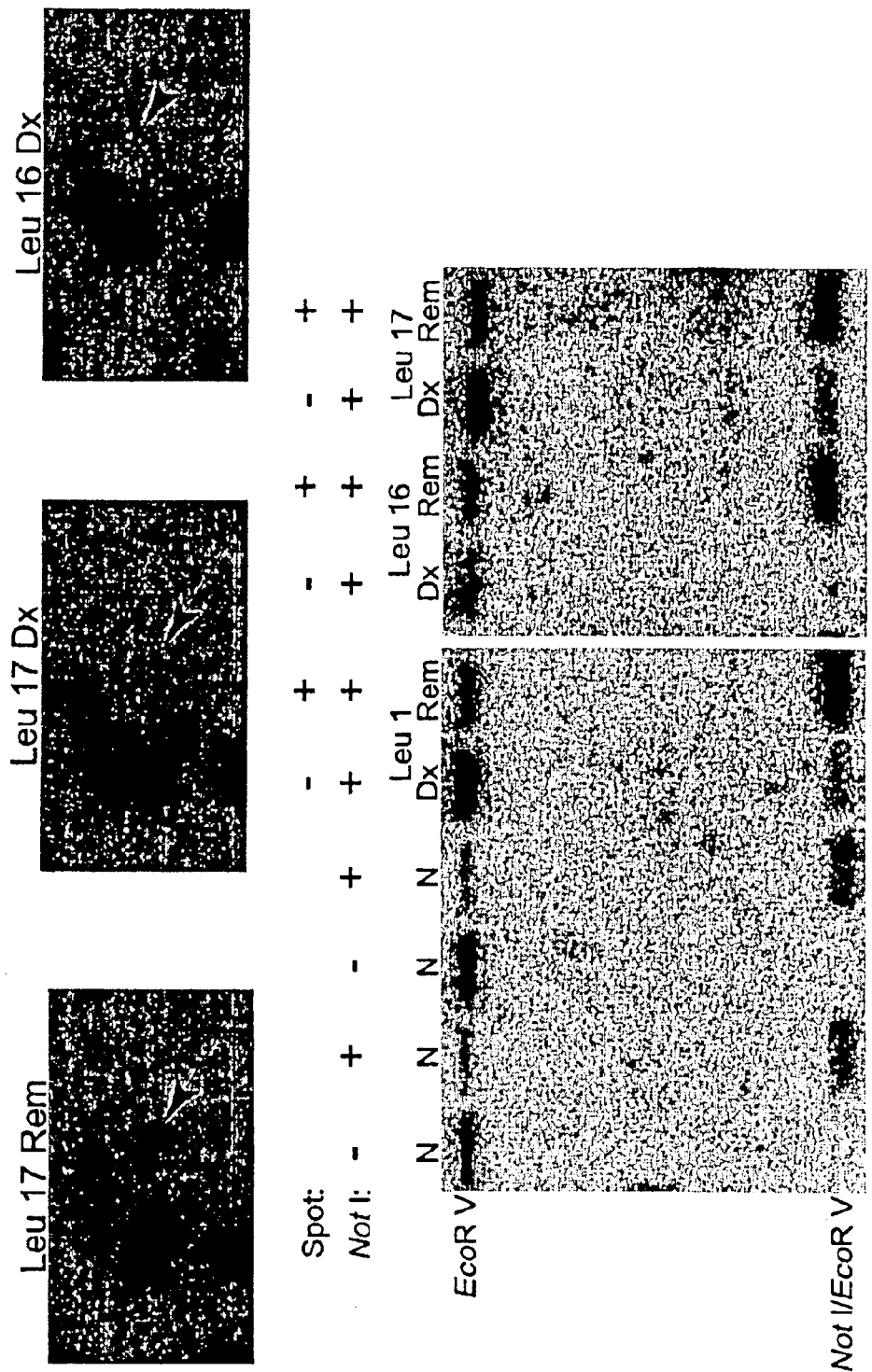
Figure 2C:
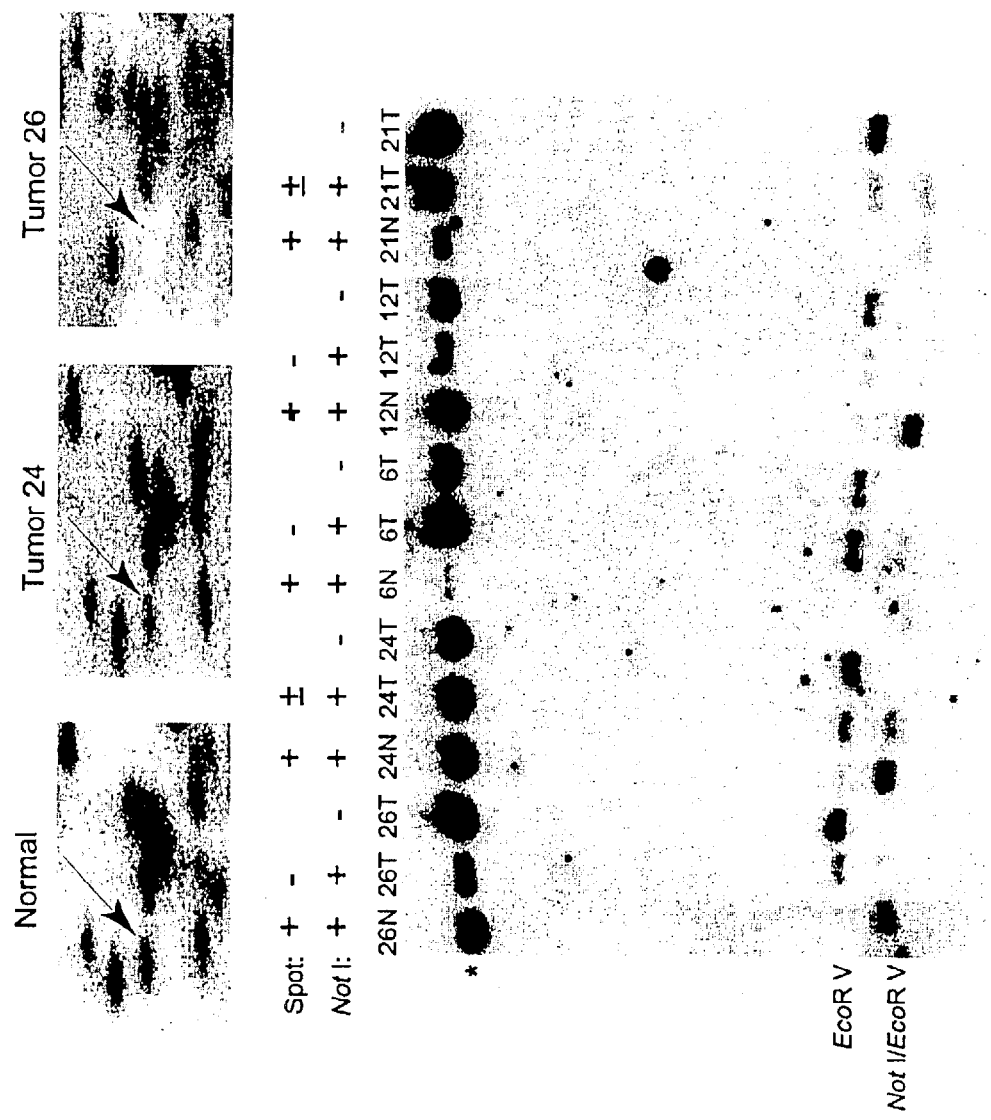

FIG. 2B shows the data The first 2 lanes of the autoradiograph are relevant. The first lane, labeled 26N is the normal, healthy tissue DNA cleaved with both NotI and EcoRV. The 26N lane shows a band near the bottom of the autoradiograph labeled "NotI/EcoRV." This is fragment resulting when the NotI site present in the 2.C.40 clone is unmethylated. The adjacent lane, labeled "26T." is the tumor tissue DNA cleaved with both NotI and EcoRV. It is seen that this band, labeled "EcoRV," does not migrate as fast as did the 26N band. The reason is that the NotI site present in the 2.C.40 clone is methylated and the, NotI enzyme was unable to cleave at this site.

B. Diagnosis of Cancer Using Methylation-specific PCR (MSR)

MSR is a technique whereby DNA is amplified by PCR dependent upon the methylation state of the DNA. In this example, the specific areas of the genome whose methylation status is to be determined are the regions at the ends of the CpG islands that are demarcated by the methylation-sensitive restriction enzyme recognition sequence. In the case of the Not/EcoRV RLGS profiles, this is the NotI site. In the case of the AscI/EcoRV RLGS profiles, this is the AscI site, at the end of each clone.

For the purposes of this example, the methylation status of genomic sequences corresponding to the NotI site of clone 2.B.53 of the NotI/EcoRV library is examined. Genomic DNA is first isolated from normal tissue and from tumor tissue, as described in Example 1. This DNA is then treated with bisulfite. This is done by taking 1 $\mu$g of genomic DNA in a volume of 50 $\mu$l and denaturing said DNA in a final concentration of 0.2 M NaOH. Thirty microliters of 10 mM hydroquinone and 520 $\mu$l of 3 M sodium bisulfite, at pH 5.0, are added, mixed and incubated under mineral oil at 50° C. for 16 hours. The modified DNA is then purified using the Wizard DNA purification resin (Promega) and eluted into 50 $\mu$l of water. Modification is completed by NaOH (final concentration, 0.3 M) treatment for 5 min. at room temperature, followed by ethanol precipitation DNA is resuspended in water.

Each genomic DNA is then used in two PCR reactions. One PCR reaction will amplify DNA that is not methylated and has, therefore, been modified by bisulfite. The second PCR reaction will amplify DNA that is methylated. Separate primers are used for each reaction. To determine the methylation status of the NotI site in the genomic DNA which corresponds to the 2.B.53 clone, the two sets of primers described in Example 3 are used Each PCR reaction contains 1xPCR buffer (16.6 mM ammonium sulfate, 67 mM Tris, pH 8.8, 6.7 mM MgCl$_2$, 10 mM 2-mercaptoethanol), dNTPs (each at 1.25 mM), primers (300 ng each per reaction), and 50 ng bisulfite-modified DNA in a final volume of 50 $\mu$l. Separate control reactions are run which contain DNA that has not been modified by bisulfite. Reactions are hot-started at 95° C. for 5 min. before the addition of 1.25 units of Taq polymerase. Amplification is carried out for 35 cycles (30 sec at 95° C., 30 sec at the annealing temperature, and 30 sec at 72° C.), followed by a final 4 min. extension at 72° C. Each PCR reaction is directly loaded onto nondenaturing 6–8% polyacrylamide gels and electrophoresed Gels are stained with ethidium bromide and visualized under UV illumination.

If input genomic DNA is not methylated at cytosines within CpG dinuceotides at the NotI site corresponding to the end of the 2.B.53 CpG island clone, the PCR reaction using the primers specific for nonmethylated DNA (primers III and VI in Example 3) will produce an amplification product of 128 base pairs in length. Using the same input genomic DNA, the PCR reaction using the primers specific for methylated DNA (primers IX and XII in Example 3) will not produce an amplification product.

If input genomic DNA is methylated at cytosiles within CpG dinucleotides at the NotI site corresponding to the end of the 2.B.53 CpG island clone, the PCR reaction using the nonmethylation-specific primers will not produce an amplification product. Using the same input genomic DNA, the PCR reaction using the methylation-specific primers will produce an amplification product of 128 base pairs in length.

Example 5

Detection of Gene Expression

The library clones (Tables I and II) and DNA sequences (attached sequence listing) are useful for determining whether genes encoded within said clones are being transcribed in tumor tissue or cultured cells. To determine transcription, RNA was isolated from five different human glioma cell lines 187MG, U178, T98G, U251 and LN235) using Trizol (Gibco BRL). Such RNA isolation reagent is known to those skilled in the art RNAs were quantified using a spectrophotometer and then treated with amplification grade Dnase I (Gibco). The RNA (2 $\mu$g) was reverse transcribed by incubation with oligo-dT and random primers in a 20 $\mu$l reaction, heated to 70° C. for 10 min. and placed on ice. A mix containing 1xreaction buffer (Gibco), DTT (10 mM), dNTPs (0.5 mM each), and RNAsin (80 U, Promega) was added to each sample. The samples were divided into two tubes, each containing 19 $\mu$l, and incubated at 37° C. for 2 min. M-MLV reverse transcriptase (RT, 200 U) was added to one of the two tubes and each was incubated at 37° C. for 1 h. DEPC-treated water (30 μl) was added to each sample and heated in boiling water for 5 min.

PCR amplification of the reverse transcribed RNA was then performed. In this study, transcripts encoded by sequences within the 2.C24 library clone (Table I) were looked for. A computer search using the BLAST program had identified an open reading frame within the sequence of this library clone. PCR primers were made to this region. Primer 1 was 5' TGGTGCTGAAGTCGGTGAA 3'. Primer 2 was 5' GGGCCATCTTCACCATCTG 3'.

These primers (10 pmol of each) were used in 10 μl PCR reactions which contained 1.5 μl of the reverse transcription reaction, 1×reaction buffer, Taq polymerase (0.5 U, Boehringer), and dNTPs (250 μM each). For each gene, separate amplification reactions were carried out using RT-positive and RT-negative reactions as template. Amplification was not detected from the RT-negative reactions.' The PCR reactions were carried out by heating the samples to 94° C. for 5 min and then amplifying for 35 cycles, each cycle consisting of 94° C. for 30 sec., a 30 sec. annealing step at 56° C., and 72° C. for 45 sec. The reactions were then incubated at 72° C. for 7 min and cooled to 4. The sample was then electrophoresed through an agarose gel containing ethidium bromide and PCR products were visualized using an Eagle Eye gel documentation system (Stratagene). The correct identity of the PCR products was confirmed by nucleotide sequencing of both sands.

The data showed that no transcripts encoded by this region of the 2.C.24 clone were found in any of the 5 glioma cell lines. Such expressed transcripts are present in RNA obtained from human fetal brain and adult brain.

In addition to examination of cell lines, tumor tissue obtained from patient samples can be similarly tested for the presence of transcripts by one skilled in the art. Other techniques to detect transcripts can also be used. Such techniques include, for example, Northern blot hybridization, RNase protection and primer extension assays.

What is claimed is:

1. A method of identifying CpG islands which are preferentially methylated in malignant cells contained within a tumor or neoplasm, comprising:

a) digesting genomic DNA obtained from the malignant cells with an infrequently-cutting, methylation-sensitive, restriction enzyme to provide a set of malignant cell restriction fragments;

b) digesting genomic DNA obtained from non-malignant, control cells with an infrequently-cutting, methylation-sensitive, restriction enzyme to provide a set of control cell restriction fragments;

c) attaching a detectable label to the ends of the malignant cell restriction fragments and the control restriction fragments;

d) digesting the labeled malignant cell and control cell restriction fragments with a second restriction enzyme;

e) separating the labeled malignant cell restriction fragments and the labeled control cell restriction fragments, wherein the malignant cell restriction fragments and the control cell restriction fragments are separated by electrophoresis on two different gels;

f) digesting the restriction fragments in each of said gels with a third restriction enzyme;

g) electrophoresing the restriction fragments in each of said gels in a direction perpendicular to the first direction to provide a first pattern of detectable malignant cell restriction fragments and a second pattern of detectable control cell restriction fragments; and h) comparing the first pattern to the second pattern to identify diagnostic control cell restriction fragments in said second pattern which are absent or exhibit a decreased intensity in the first pattern, wherein said diagnostic control cell restriction fragments comprise a CpG island that is unmethylated in the DNA of the control cells and methylated in the DNA of the malignant cells, wherein the tumor or neoplasm is selected from the group: colon, glioma, lung, and non-medulloblastoma primitive neuroectodermal tumors (PNET).

2. The method of claim 1 further comprising the step of determining the sequence of at least a portion of a diagnostic control cell restriction fragment, wherein said portion is located at or near an end of the fragment.

3. The method of claim 1 further comprising the step of obtaining a clone from a DNA library which comprises a diagnostic control cell restriction fragment.

4. The method of claim 1 wherein the tumor or neoplasm: from colon is stage I, II, II or IV as classified according to the American Joint Committee on Cancer staging and from PNET is supratentorial PNET.

5. The method of claim 1 wherein the tumor or neoplasm is a primary tumor or neoplasm.

* * * * *

SEQUENCE LISTING

<160> NUMBER OF SEQ ID NOS: 90

<210> SEQ ID NO 1
<211> LENGTH: 677
<212> TYPE: DNA
<213> ORGANISM: Homo sapiens 2.B.53
<220> FEATURE:
<221> NAME/KEY: n
<222> LOCATION: (578)..(578)
<223> OTHER INFORMATION: a or g or c or t

<400> SEQUENCE: 1

```
gcggccgcgg ttagcttctc ctgtccgaac gcagggtttc actgggcgc cgctacggtt      60 cctatggcaa cgcggctcct cgacgcagcc caggagtcgc ggtcgcggga ggctgcgccg     120
cgcaccgagc tcttccctgt ggccgccgca gccgccagcc tcttcctgct catgcttttc     180
ctcatcttca tctcggtctg agtgggctct ggacctctcc accagcctct gccccagaac     240
tgttaactgc gggggggaaa aaaggaattt gtcgtcgcaa cgcgcgttcc gatggagccg     300
cacgccacaa aggaagactc atgctgcacc ccgcgggca gatgcggcga cactggacat     360
cgctgcacag ctgggtctgc ccgtttccag agctgcttag cgccgacgcc cataaatgag     420
gaggactccc tgtgtattaa aaggggggatc cgcagggttt aatttgataa ggattatagc     480
cttcataaag gcatttttaa caaaaagatg taggtggcat ggtaatcgag tattatttac     540
gcatctctcc gcacacgcac tcatacctga aaacgttntg gcaggcacaa aatgattttt     600
ttgtgtataa aagaatgtgt gtaactcgtg gatggtgggg ttcagcagga caagatagtg     660
acattagata aattaca                                                    677
```

<210> SEQ ID NO 2
<211> LENGTH: 380
<212> TYPE: DNA
<213> ORGANISM: Homo sapiens 2.C.24
<220> FEATURE:
<221> NAME/KEY: n
<222> LOCATION: (246)..(246)
<223> OTHER INFORMATION: a or g or c or t
<221> NAME/KEY: n
<222> LOCATION: (297)..(297)
<223> OTHER INFORMATION: a or g or c or t
<221> NAME/KEY: n
<222> LOCATION: (318)..(318)

```
<223> OTHER INFORMATION: a or g or c or t
<221> NAME/KEY: n
<222> LOCATION: (325)..(325)
<223> OTHER INFORMATION: a or g or c or t
<221> NAME/KEY: n
<222> LOCATION: (327)..(327)
<223> OTHER INFORMATION: a or g or c or t
<221> NAME/KEY: n
<222> LOCATION: (345)..(345)
<223> OTHER INFORMATION: a or g or c or t

<400> SEQUENCE: 2
gcggccgcct tgaaggcgct ggacgggatg gtgctgaagt cggtgaagga gccccggcag      60
gtgagctcgc ggcccgccag cccgctgccc acgcagtagt ggaagaggcc gaagtagcca     120
ggcttggggg tgctcacgct gtcgccacc cagtagggct ggatgaagac caccacgttg     180
atgatggcga agcagatggt gaagatggcc cacagcacgc cgatggcccg cgagttccgc     240
atgtantgct cgtggtagag cttggaacct cctgcgaggg cagcatggtg cccggangcg     300
gggccggcgg cggctgtnge tggcngnggc cgtcggcccg gacngacgc ctggctgccg     360
ggcgggaact ggggactcac                                                 380

<210> SEQ ID NO 3
<211> LENGTH: 566
<212> TYPE: DNA
<213> ORGANISM: Homo sapiens 2.C.29

<400> SEQUENCE: 3
gcggccgccg cgctagtgac tacttcctcc tactccttct cctcctgctc cggcctcctg      60
gcgccctgct ccaggctctc cggcgccctg ctccaggctc tccggcgccc tccagccagg     120
caccggccga accgggtagt gccgcaaggt gtaattactg ctttgaaact ttaaaggcat     180
ttggaaagaa actacgggtt atgcttactt ttttgtttt tgattattat tttgtaggag     240
acacaaagtt taaaatagaa agcaaaaag tgtgacacat ttaaagagtt aaggaaata     300
aacgtttcca atttaccttta taacatgatt ttcatacact ggatttgttt aaaacagact     360
gactacatgg ataactttc taggaattgt tcttaactct gatagctggc tcaactgatg     420
taggcattaa ataacgtca tattaccatc tttcctccac gaattgatga tatttgacta     480
tagctttgtc agggtatgt ccaactattg tataatatgt gtcagtttcc tattgctacc     540
gtaacaaatt accccaaatt tactgg                                          566

<210> SEQ ID NO 4
<211> LENGTH: 1297
<212> TYPE: DNA
<213> ORGANISM: Homo sapiens 2.C.35
<220> FEATURE:
<221> NAME/KEY: n
<222> LOCATION: (1046)..(1046)
<223> OTHER INFORMATION: a or g or c or t

<400> SEQUENCE: 4
gttcacttct cgctgcgccg cgggttctgt agaagcgcaa gaatgggct gattattccg      60
gtgcccacat gccgccccca cacgccccca ccccgtccg gcgcaagact tcccttggcc     120
aaaagaggcg tttaattagt tctggggccg cggagagcca gcgtggccga caaagcccgg     180
ctccccaggt aacccgggtt ccctgcgac ccggagggg gcgcgcgggg ccggagcacc     240
ggccttgggc tgcgcgctcc ctccggcgac actgccgtcc cctggcctc cggcccggtc     300
ccccgcaggc caaaggctca tctgccgggc ttgggtggcc cgggccagcg ccgcctgcgg     360
```

```
tccccgagtg cggctggctc taaggccggc gccctctccc cggctttcag tgctcagagc      420
caggccagcg ggaaagaagg cagcatggtc cgcaaaagac aggtggcagt ggcagtcttg      480
catgatactt gtccttcttc cctgttcccc attttgggga acactggaa acacttttct       540 ctttatgcgc attcgcgtct cagcaccgag tgctccaagc cctgcgcgca cgccgggct       600 tggaaggcgg cgaatggctg cctagccgcc gccctacta gtgacactcg gccgccagcc      660
cccgcccagg atgtgcacat ctgctggcag cactggcccg gtggcagtc accgggccac       720 ccactccaca ggtacaaccg cacccaatcc aacctggaac tcggagggct gtgcgcgccg      780
agctgggatc gcgccccaac gagccgggcc tttggctgcg ccaggcccca ggccgagtca      840 tcccccgct cgcgtcgccg cgaggcggga caccgtgtaa tacctttgcc gtgggctggg       900
cgtcggccgc gggccggaga gcgggtgtcc cacctcgcct catcatttga tttccgccag      960
cgtctgagga cggcgcaccc aattcgttcc actcgctgcg ctctgtgaac cagcggcggg     1020
cagggcgggg gaggccgggc tggggnaggg cagggtggtc ccaatccccc gccccgcccc      1080
cgccggcctc gcggagcaca agtgttggga ttcccacggg caggcgtgct ctgcggctgg     1140
aggcccgagc gcccagggcc caggagacgt ggcggacaca gaggggtttg taggcacggt     1200
gacctccgtg ctcctgctct gaaagggcct gaaaggagcg gtttatggtg cattaccagt     1260
caagggctca ggtaccagcg cctgtgtcgg gaacccg                              1297

<210> SEQ ID NO 5
<211> LENGTH: 651
<212> TYPE: DNA
<213> ORGANISM: Homo sapiens 2.C.54

<400> SEQUENCE: 5
gcggccgccg cggggacgc tcagatctcg cgagaagagg gcgagcgcgc tgccccctg         60 gtgggcgggg cgaagcccgg gagagggtgg gcgccaccgg aggggaggag gggaacaggg      120
aactgaagga agtgggaggg gccggcgggg cggggaagcg gaaaggggc gtggctgagg       180 gcgggaggat taagctgcct ttttgaaagt ggagcgccag gtcccgggtt ctgggtggag      240
gtggttgctg attggtggag ctcggagcgg cggttgggag ggtcctggtc acatggtggg     300
gagtgggagg ggggaagttc ggagagcggg agcgggatgg tagtgggctg gccccactg      360 ggctgggaca gcaggaggat agtcttgagg aggagcgtgg ggtgctagat gtgtaactac      420
gtcccgaact ggttcctgtg tttttctagg gcatgtggac tagggatggg tacttgagta      480
gaagcctgca acttgaagag tttgtgcagg agttagctgc agtgtcggaa attagtgtcc      540
tgtatgctca acaaggtatt cggactgggt gtgcacacca cagctctcag gactggaagg     600
tggaaattta atctacgaag ttcccttaaa ctgcataagc ttcgggacct c               651

<210> SEQ ID NO 6
<211> LENGTH: 710
<212> TYPE: DNA
<213> ORGANISM: Homo sapiens 2.C.57
<220> FEATURE:
<221> NAME/KEY: n
<222> LOCATION: (652)..(652)
<223> OTHER INFORMATION: a or g or c or t
<221> NAME/KEY: n
<222> LOCATION: (690)..(690)
<223> OTHER INFORMATION: a or g or c or t
<221> NAME/KEY: n
<222> LOCATION: (695)..(695)
<223> OTHER INFORMATION: a or g or c or t
<221> NAME/KEY: n
<222> LOCATION: (710)..(710)
```

<223> OTHER INFORMATION: a or g or c or t

<400> SEQUENCE: 6

```
gcggccgcac ggagttgaag acactaaccc agctaagcca catacagacc ctcacggccg        60
cctggtctac acaggccgcc acagctacac aggctcaggc ctcagcctgg tcacaatggt       120
cacacccaca ctctcgggtc ccacagtttt gcgggagcgg tgacacacac ccgctcccaa       180
ctgaccacgc ccacacacgc tggcttcagc cgcacacgca cacagtagcc acgccccctt       240
atgctccagc cttgccagca cccgccctcg ccacgctggt cacgcccaca cacacacaca       300
cacacacaca cacgcacgcg caggcctggg gcacgccccct cccccacacg caggcgtgcg       360
gcacgccttc ccatacacac acacgcgcg cgggcctggg ggcacgccct ccacacacat        420
gcagggtag ggcacgcccc cacacacaca cacgccggcc tggggcacgc tcgcgcgcac        480
atgcacacac atacacacgc acaggcctgg ggcaggcccc accccacac acgcaggcct        540
ggggcacgcc ccccacaca tgcaggcctg gagcatgcgc acactcgcag gccttgggca        600
cacgcgcaca cactcatgca cagacacgca cgcacacatc gagccccgcc cncggaagca       660
catgagaggc acttgctttc actgactgan ggcanggctt tgggcccgcn                  710
```

<210> SEQ ID NO 7
<211> LENGTH: 1204
<212> TYPE: DNA
<213> ORGANISM: Homo sapiens 2.C.58

<400> SEQUENCE: 7

```
gcggccgctc ctctttattc tactctcacc cgaggcccgc gcccgtcccg gggagcggct        60
ctgccaggaa aacggcccga ccagtgcccg gcgcctgggc tgcgtccgag cccaccttct       120
tccctcgtcg tcgtctccca gactaaatcc cggaaaggga aagcgggatg tttgcgccca       180
ccgcgctgta gctggtcctg acacttgcaa aatggtcagt ggctcctgct cggccaggct       240
gagtgtgtgc gtgtgtgtga gcaagggagc gagggtgtgc ggtgtgcagg gggtgcgctg       300
tgtgtgcgcg cgtctccggg aaggtctcgc ggcggctgga gccgggactg acagcccggg       360
cggagcgcag gcagctccac acgctaaacc tctcgcctct cccctcaccc ccacccttc        420
cactcccctc tccttccccc accctccccg gccccttcca agctctctga ttggccaatg       480
ggacaaaagt ttctgtggag acggctgggc gctgacgtca cgggcagaat tgtcccattt       540
agggatcccs ggggcagtgc gcatgctgca ggctgcaggt tagaggcaga aggaggtagc       600
agcgggcccg gcggcagcca ggtggcagaa aggagcacgc agcatccagg tgggggggacg       660
actccagcag ggtttccatg gagattcctc tgggtctagc ctaaaaacag cagatcagct       720
gacaccatta gctcaggacc taattactgc ttattggagc aacaaatgag ggaaagggcc       780
agctgcaaag gaagagtttt tatccccccca ccccattccc ccatctcctt tctcccctc        840
tctccatccc tcttgagtcc cgggtgaatt ctcattaact tgcaagattc ctgcaacaac       900
agctccccctt ctccagaggc caccccgact gcttttattc ttttatttcc ttcttttgta      960
ttaaaaagaa atgctaaaat aaatcagttg ttgagtcctt gaattttgt tcaatacgta       1020
ttagaccata gagctcagag aagacactgt ccaatgaagt cacaagtgaa tctaatacaa      1080
gggactcagg ggaaaatat cactttcaat ttattgaggt gaatctttag atatttcaca      1140
ttaaaaaaat cttaatatct aaatacata aatatttgaa acacgcaatt ggacagaaga      1200
tatc                                                                  1204
```

<210> SEQ ID NO 8
<211> LENGTH: 687
<212> TYPE: DNA
<213> ORGANISM: Homo sapiens 2.C.59
<220> FEATURE:
<221> NAME/KEY: n
<222> LOCATION: (650)..(650)
<223> OTHER INFORMATION: a or g or c or t

<400> SEQUENCE: 8

| | | | | | |
|---|---|---|---|---|---|
| gcggccgcac | aagcgcacac | gcacacgtcc | agggcggagg | aacactacta | gtaacacccg | 60 |
| cctccttcta | gcctccctat | cccaaagtta | tggtgccgat | tttgtccgcg | gcagggctc | 120 |
| caggggcaca | ctcataaatt | cggtgcggag | gaacacaact | agcagcacca | cacccccgcc | 180 |
| actgccagaa | ccaaagtgac | ggtgccgaca | cccctccgca | agcgcaaggc | cgacttccat | 240 |
| aagtaattag | ccagagcacc | gtcccgttcc | tgtcagcacc | gagccccagc | caggacaccg | 300 |
| gtattcccag | caccatacaa | gaactacttt | ttcgatgaag | caacccaaaa | gctgcgagcg | 360 |
| gttcccggtg | aggccgccca | ctcacctggc | cggcgcagac | aagctccgtg | cgtcaagaca | 420 |
| taacagcgta | agtgtacgac | gttgcgcagc | gacgcggggg | ccttcgggaa | atgtagtcta | 480 |
| caactggaaa | ccggccggat | cgtgtctgcg | caggcccagc | agctaagatc | gggtccggcg | 540 |
| ctccagaaca | gaacgatccc | tgaggctccc | ttgctcgaac | tgtgggactt | accctactat | 600 |
| ggtccgagcc | tacctatttt | cattatactc | aagtaacgcc | ccagaaattn | cagagaatct | 660 |
| acacaaagag | gttgagtctt | gccgtgg | | | | 687 |

<210> SEQ ID NO 9
<211> LENGTH: 1520
<212> TYPE: DNA
<213> ORGANISM: Homo sapiens 2.D.10

<400> SEQUENCE: 9

| | | | | | |
|---|---|---|---|---|---|
| gcggccgcga | ggacagctcg | gacgggggag | agaaggagg | tttccagtaa | aaataataac | 60 |
| gccagagaga | aaccgtaac | tcgcgtgaca | cagacagaaa | tttccagtaa | taatcatcag | 120 |
| gtgatagaga | aggaaggctt | ccaaaatgaa | gaacaagtga | aataaaggtt | ttagtcatga | 180 |
| attacagcac | gtgcgatgga | tgagtggtga | tttctcatca | taaatggtaa | ctcgggagat | 240 |
| agagaaacgt | gtccagccct | aaactacaac | agggtttggt | ttgaaagaga | ggtgctgtca | 300 |
| taaagcggaa | ctcaggggat | ggggaagacg | gcctccgtcc | caaatgacaa | ctcaatgaca | 360 |
| gagaacaaaa | gatccaaact | aaagtgatgg | agaaaaaggg | tttccaacca | ccacacaaat | 420 |
| gaagagaaag | actgatcaca | taatgaagta | ttcagtcatt | aatacatgat | aaacccggtg | 480 |
| atagagaaag | aggcttagtc | acaaattact | cagataatgg | agaaaaaagc | cttattcatg | 540 |
| tatcactcag | gtagatacat | caaggcaggt | ttcctgccat | aaaggataac | acagctaaaa | 600 |
| gagaaataaa | ggttttagta | ataagtgaca | attcatataa | cagagaaaga | aggcttctgg | 660 |
| ccataaggat | aactcatgta | ataagaaaa | gttttagtca | taaataatag | agaaagaaag | 720 |
| gtttccgata | gaaaatggta | gagatagaaa | ggttctaggt | aacaaacggt | aactgaagtg | 780 |
| atagagcaag | gtcacaaata | taactcagg | taatagagaa | agatttctag | tcataaataa | 840 |
| tacatctgct | acagaaataa | gggttttgat | tcataaagtt | atgtcataag | tgataagtgg | 900 |
| tagaaaagga | aaggttttag | ttataaatta | tgattcaagg | gatagaaaaa | caaaggtttc | 960 |
| aagttataaa | tatcatttca | atggtcaaga | aaggttttca | gtcatgaatg | aaaactgggt | 1020 |
| gaagttttcc | agtcacaggt | tataactcag | gcaatggaca | gagaaggaaa | gattttgtc | 1080 |

-continued

| | |
|---|---|
| atcaatcaac tcaggtggag aaggaaaggt ttttcaataa gaaataactc agttgagtga | 1140 |
| aagaaggctt gaggtcatga atgataatta ggtgatagag aaagaaatgt tccagtcata | 1200 |
| agggttaaat cagatgctag agaaagaaag gtttttagtc ataaataaaa ctcagctgct | 1260 |
| agaaagaata gggctaccag tcataattga taactcaggt gagagaaaga ttgctggtca | 1320 |
| taaattgtaa cccaggtgac agaaaagaag gtgtcactca cacatgataa ttcgggttat | 1380 |
| gaggaaggtt tccagccaca gtggtaactc aggtgctagg gaaagaaggt ttgggcaata | 1440 |
| atgacaactc aggtaataca gaaaaacgat tacagtcata aatgacagag aaggaaaggc | 1500 |
| ttttattcat aaaggatatc | 1520 |

<210> SEQ ID NO 10
<211> LENGTH: 575
<212> TYPE: DNA
<213> ORGANISM: Homo sapiens 2.D.14

<400> SEQUENCE: 10

| | |
|---|---|
| gcggccgcgg ctgtggctcc tcttggccgc gcagctgaca ggtaaggcgg cggcgcgcgg | 60 |
| gctacccaag ggtctgcgct cccggggcct gagcggggag gtgataagtg gctgtcctgg | 120 |
| ccctggtcct ggcagggtgc agcgtcgagc ccgcggtggc ggggcgcccg ggaggcagct | 180 |
| tggcaggcac ggtccctaag ggtggaaata aataccccc atatcgcatt accccgggg | 240 |
| accggagagc ccctggactg aggccacctc ccctcaaaag cctggacgca ggagaagggg | 300 |
| aggcagtgaa aaggggagcg agtgagggaa ggaaagagag ggtcgctgga ggtcaccagg | 360 |
| ggaaggaaac aggtccctgc ccagggtccc cgcaggatgt gctcggagga aggttggcca | 420 |
| ggccatgggt cctgtggaca cattttatt acttccgggg aagtgtttgt agtacaatca | 480 |
| gacaaacatc gggcgttctc agttctcgga gggctagggc agggtgatcc ctctggctcc | 540 |
| cgttctccct gatgtcgctg gtgttgggtg tcatg | 575 |

<210> SEQ ID NO 11
<211> LENGTH: 741
<212> TYPE: DNA
<213> ORGANISM: Homo sapiens 2.D.20
<220> FEATURE:
<221> NAME/KEY: n
<222> LOCATION: (691)..(691)
<223> OTHER INFORMATION: a or g or c or t
<221> NAME/KEY: n
<222> LOCATION: (732)..(732)
<223> OTHER INFORMATION: a or g or c or t

<400> SEQUENCE: 11

| | |
|---|---|
| gcggccgcgt cgtcgctgag tacaccagct gcctcatcta tctggagccc ggcctccatc | 60 |
| tcgccaggct cagcgcccgc gtccgtgtcg gtgccggagc cattggccgc gcctagcaac | 120 |
| acctcgtgta tgcagcgctc cgtagctgca ggcgccgcca ccgcagcagc ctcttatccc | 180 |
| atgtcctacg gccagggcgg cagctacggc caaggctacc ctacgccctc ctcttcctac | 240 |
| tttggcggcg tggactgcag ctcataccta gcgcccatgc actcacatca ccacccgcac | 300 |
| cagctgagcc ccatggcacc ctcctccatg gcgggccacc atcatcacca cccacatgcg | 360 |
| caccacccgt tgagccagtc ctcaggccac caccaccacc atcaccacca ccaccaccaa | 420 |
| ggctacggtg gctctgggct tgccttcaac tctgccgact gcttggatta caaggagcct | 480 |
| ggcgccgctg ctgcttcctc cgcctggaaa ctcaacttca actcccccga ctgtctggac | 540 |
| tataaggacc aagcctcatg gcggttccag gtcttgtgag cccaggaatg aaagaggaga | 600 |

| | |
|---|---|
| agaaacgcaa ctacctgcgc cctccgtggt cccgatcctg ttgctgctgc tgcaccgccc | 660 |
| gcctttgcct cgtcttctcc aaaaactgat tntcaccccc caaaagatgt ccattgcctg | 720 |
| cactgccgcc cncatttttg t | 741 |

<210> SEQ ID NO 12
<211> LENGTH: 458
<212> TYPE: DNA
<213> ORGANISM: Homo sapiens 2.D.25
<220> FEATURE:
<221> NAME/KEY: n
<222> LOCATION: (333)..(333)
<223> OTHER INFORMATION: a or g or c or t
<221> NAME/KEY: n
<222> LOCATION: (372)..(372)
<223> OTHER INFORMATION: a or g or c or t
<221> NAME/KEY: n
<222> LOCATION: (426)..(426)
<223> OTHER INFORMATION: a or g or c or t

<400> SEQUENCE: 12

| | |
|---|---|
| gcggccgcca gtagcagagc ccagcacatt gcgggtgccc agttcatctt cgtgggktta | 60 |
| aacctgcggg aagagaggga aagggcccctt agtttccatg gagatcgggt gcccaggggc | 120 |
| ggagggctca aggctggaga gcagagggac ccccatcttt tgtgggatca gggtgccccc | 180 |
| agcatcttgg aggcccactg aggcctgggg gggcgcggtt taacttctag catcagggac | 240 |
| ttaggcctgg gggaggcgct gggaagtggc aggtggggca ggagggttct gcacctgaag | 300 |
| gttgtgcacc tggattgggg gtgtagaagc ggngcaggag cgccgcggtg ggggcgtcca | 360 |
| ggcccgggcg gnggagcaag cctgggggag ggagctctgc acgcgttgct gggatgtggg | 420 |
| gggcgngggg aggcggcatg gggggagggg cgttgtgt | 458 |

<210> SEQ ID NO 13
<211> LENGTH: 615
<212> TYPE: DNA
<213> ORGANISM: Homo sapiens 2.D.27

<400> SEQUENCE: 13

| | |
|---|---|
| gcggccgccc ggcgtcccgc tctgggggc cgggaccgaa gcgctcacgg cccggggacg | 60 |
| cggggttggt ccaggctgcg gcctgtggcg cgtgcaggcc tgaaggaggc gagatgccga | 120 |
| tgccgccacc gctggtccgg tggaccaggc cccttggtcc agcctcccct cccgcagccg | 180 |
| cccgtctggg ggtgttcgca gccccgggct cccccggccc gccgccggg gagtgggagg | 240 |
| gcgatggcgc cccgcctccg gctcttacgg agagcgcgct tcccctcaa ctccggcggc | 300 |
| ggtgagccgg ggtgcgatgc gcggccgagg cctcgcccgg accgccggtc cccatcgcgt | 360 |
| ccctgggcga gggaggggcg gttggccgga gatggcggag gggcgtaccc gccccgcctg | 420 |
| cccgccgtcc ccagccctca gcgcctgggg aagcccctgc tgtggcagtg ctcgggcgct | 480 |
| atccggagga agaggagcag ttcctctttc ttggctgcgg cagggctgct gggccggaa | 540 |
| aactaacttg tgtcggcgcc cagccgcccc gcgccggctg ccggctagct caggccgacg | 600 |
| ccgaggggag cggcg | 615 |

<210> SEQ ID NO 14
<211> LENGTH: 669
<212> TYPE: DNA
<213> ORGANISM: Homo sapiens 2.D.34

<400> SEQUENCE: 14

| | |
|---|---|
| gcggccgcgc ggggcagcgc gaggaactgt tgatttgcct gcgccttggg ccctgcgtc | 60 |

-continued

```
tctcccaggc ggcggctccc gctttcctca aaggccgtgt cgggtttgtt gtttggtgtg      120
ggtgccggga aagggcgctt ctccccagtg aggtggggaa cttgggtgat gggaccacgg      180
aggcgccggt tcgtgcccgg tggggacggg tgaggcaggg gagagtgaga ttttattctc      240
ccccaaggaa ggagtgtccc cttctcctta ttttgagggc tattcaagct tattgaaacc      300
agaaagcggt gtttcttgtc aatctctcag cccccttcttc caaccaagaa caattgtcga      360
tgagtttcca tcacaggcgc ttgtgagaga accggtaaac ccagtacagc aaaatccaag      420
cccttggttt ccacatgcat tttgctagca gttttttggca ttgaccctcg ccctcccgtg      480
tttccactcg acatcattta gcgtttgagg ttttttttccc tcctcaaaat tgcaaatgag      540
aaaaaaagag gaaaccagga aaaggggggtg gggggtagca tttaaattgg atgtgagttt      600
ctgctgagaa ttctagcgaa gtcccctgta cactgaagcg ccgagagatt tttccgtttg      660
tgtatcttc                                                              669
```

<210> SEQ ID NO 15
<211> LENGTH: 998
<212> TYPE: DNA
<213> ORGANISM: Homo sapiens 2.D.40
<220> FEATURE:
<221> NAME/KEY: n
<222> LOCATION: (929)..(929)
<223> OTHER INFORMATION: a or g or c or t

<400> SEQUENCE: 15

```
gatatccatt ataatactat ttgacctcaa agtgaatttt attgttccac acaagcaaca       60
gattacacca atttcacaac tcccagaatc caaacctaca aagacccttc ccaccaagca      120
ctttaccaaa aacgggcttc atctccatct tcctttcttt cacagttgaa aaactgccct      180
tcctaattaa gccaaccaac ttcttacctc aataaaatcc ttgttttttca gtagcatgta      240 cagtatttcc agtgatgaac agtgaactgt ctttcgtctc acacagtaac ctccgtgaag      300
aagatccacc ttgttctttta ctgtatattc ctggcatgct aactgcatcc tcagacaatt      360
ttaagtgact gaaaactcag gcaaagaaag gcaagagggc aaatagaagg gcacaggaga      420
caacgctttt caaattttttc tcactgcgac ctacagaaac acactgtaga acacctccta      480
gtacactcac acgtgtgtgt acacctgaag tgtcaagaaa caatacccta agtgcaacac      540
cctctgatat tttctatttc aagtggccgt gatctactaa actgatttcc aactcaccaa      600
taggattcag tttgaaaaac actgcaataa atcaaacctt acagttgcat tccacaagct      660
actaatgaac tcttgaaaat ccagcataca gcagagacgc tgaccaacta caagatccaa      720
accccccagg tgggcagtgt ccttctgttc agcagtggca gttccccacc accaccagcc      780
ctgagagtta attatctccc aaactcccag agtttcccaa gtagcctgag gtgtctgtca      840
tatgcccttt taacctcttt ataaattcag tcccgtccgt ctcttacggt ggcaaagttc      900
atttatcgtc ggctgtggaa agcaatacnt tcttttttgtc cccttcagga acccagaatt      960
aatgaccagg ttggtgcccg gtgtgccttt atgatcta                             998
```

<210> SEQ ID NO 16
<211> LENGTH: 797
<212> TYPE: DNA
<213> ORGANISM: Homo sapiens 2.D.48
<220> FEATURE:
<221> NAME/KEY: n
<222> LOCATION: (679)..(679)
<223> OTHER INFORMATION: a or g or c or t
<221> NAME/KEY: n
<222> LOCATION: (687)..(687)
<223> OTHER INFORMATION: a or g or c or t

<400> SEQUENCE: 16

```
gcccctctga gttacgggga gccctgcaga cacccagccc ctggggatcc tctccccgac      60
ctgcccttcc cctccgacac ttgccagtac tccccggcct ggtattcctt tcgagacccc    120
ctcacctatt ccaggctgtc ctccactgag gcgaagctct atgaagtagc ccaatttcaa    180
tataattcac gttgtgtaaa agaactttga agacggacta catcgtgcaa ggacaccgtc    240
acccgaaaac cattggtgga acgttaaaac aaacaaaaaa caaaacggca aaacctttt     300
gaaggcaatt ttgacattta tgaatttaca gttattattc ggtttgtccc tgaaatgtca    360
cttctgaaaa tttgcatagt tttcattatc actaaaataa tctagtaaat attcccgaat    420
gaatgcattc aagaatattc actaaattat tttagtgata aggaaaaagt ggaaatagct    480
gacagtcatc aatttataaa taaaatgatg gttaaataaa atgatgaaca ttcatataaa    540
ggaatactct atattcagac gagatctgtg tgctcacagg caaacaggtc taagcttact    600
ttaaatgaaa aaggataaat tgcaaaaaga atagtttgtg taatatgatt ccacatttgt    660
aaaaatggag aaagaaatng taagcanatg tctgcaagca atcagatatg attagtgact    720
taatttcatg gatagttata taggaaatat atgtatattt tatatgcaca tagatatgga    780
ggaatatact ttcactg                                                   797
```

<210> SEQ ID NO 17
<211> LENGTH: 1024
<212> TYPE: DNA
<213> ORGANISM: Homo sapiens 2.D.55
<220> FEATURE:
<221> NAME/KEY: n
<222> LOCATION: (499)..(499)
<223> OTHER INFORMATION: a or g or c or t
<221> NAME/KEY: n
<222> LOCATION: (768)..(768)
<223> OTHER INFORMATION: a or g or c or t
<221> NAME/KEY: n
<222> LOCATION: (846)..(846)
<223> OTHER INFORMATION: a or g or c or t
<221> NAME/KEY: n
<222> LOCATION: (847)..(847)
<223> OTHER INFORMATION: a or g or c or t

<400> SEQUENCE: 17

```
gcggccgcgg cgctgcacgg gcgtgacgtc atggcgccgc ggagccgcgt cctccccgcc      60
ccgccccgg ccggggtcac ccacccgctg ccggggctga cagagaccct ggcccgcggt    120
ctgcagcctc ctcagtcgtg cgtgcgttca ttccgctcat agcttctgtc actcagcaag    180
cgctcaacac agacgcatga gataccctgg ctggaaggcc ctgaaggta gtcgtccatt     240
caacacgtgc ttagcgcgct gctgatctgt gccaggcact gggccagggc cccgacacgc    300
gtcagggtag aagcaagcag aagcctggcc ctgttggagc ttacattggt aaataaccaa    360
gataatttca ggtaaatatt aggtcctatt aaaaatatgc gtcttcgcca ggcgcggtgg    420
atcacgcctg taatctcagc actttgagag gtcgagcacg gcggatctc ctgaggtcaa     480
gagttcgaga ccaacctgng taatggtga aaccgcatct ctacaaacat acaaaaaaaa     540
aaattagcag tgagctgtga gcttgcacca ctgcactcca gtctgggcaa caggacgaga    600
tcttctaaca acaacaaaaa aaaagtatgg gccacctagt ccagccaaaa aaacaaagtg    660
ctttttttt gctttttttt tttttttttt ttttgagat ggagtctcgc tgtgtcgccc      720
aggctggagt gcaggggcgc gatctcagct cactggaagc tccacctncc gggtttacgc    780
```

-continued

```
cattctcctg gctcagcctc ccgagtagct gggactacag gcacatgcca ccatgcctgg      840
ctaatnnttt gatttttgg ttgggtgttt agtagagacg ggttcatcgt gtagccagat       900
ggctaactct gactgtgatc tgcacttgcc tccagtgtgg atacagggga ccacttgcag      960
caaagctcta ttcctgtagg agggtgttg tgaatcagac ccatttgga aatcaaattc      1020 tagt                                                                 1024
```

<210> SEQ ID NO 18
<211> LENGTH: 1854
<212> TYPE: DNA
<213> ORGANISM: Homo sapiens 2.D.74
<220> FEATURE:
<221> NAME/KEY: n
<222> LOCATION: (258)..(258)
<223> OTHER INFORMATION: a or g or c or t

<400> SEQUENCE: 18

```
gcggccgctg cagaccctgc tccaggcgcc gtagccttgc aggaagagca gacaaagaca       60
ggagagaggc aaagcgccgc ttgcccagag atgcagtcgg ctcagtcaat agagggaaat      120
cgcctccaaa cccaggctgg gaatgaggga ggaggggcga ggcggctggg gactagaaaa      180
agcagcaggg aattaacgtg acagtcagag cccagccagt gcctcgccgg cgctgctctc      240
tcgcctcgcg gttgcggngt ccggaatgga gagaggaggc ggggggctgag ccgttggctg      300 ccggagacca gctgaggtag gagtattaac tccctctgct gctctcgcct gccttcctcg      360
caccccctta cacagctcta cttgcagcag gctatgcccc cattctttct cctattttc      420 taactactga gatcagagct gaattaagct ggtgaaagga gcaaacgtg caagggattg      480 attgccctcc ttgggggaaa agcggaggct taaaatcaat tcgacaaatg agtgtttact      540
gggtgctgag tactgtgctc cgctattgtg agggagggtt atgaataagg tacccccctc      600
ccgccccagg gtccgttgtc agatctcaga atcagtttcc cctgcagttc tggaagccca      660
aagtttcggg gttgagttgt ggtccctgat cccgatcctc aaccaatcta gctttctaaa      720
tcagaagaag gtggaattca attttccttt ctccttcctg ggatgacttt aacctgcagc      780
cgaaatggag tctataggcc ccttaaaaaa gcgcgcgcac gccagtgtgt gtgtgtgcga      840
gcgcgctcgc gtgcgcgcgt gtgttttaag agtaagtcaa attaatggtt ttagtgatgt      900
tcttatttca tgattttaat tatttaccat atctgcagta gacaccagtt tggggcagag      960
gaacccgcct ctccagactc tacaaatacc accttttttt ctaaagcttt tttccgctac     1020
cccagtcctc tgactcgagg cagaaatctt tcccctctct ttgccctctc agaattttat     1080
ttgccaatca cttgcggaac ttatatattt atagatttat ctcttcactc acatatgagt     1140
attccctgtg cttttttgttt gtttgttctc actgcaacat ccagcagtgt tttgtatcta     1200
atgggtactc aaggaaagct tatccagttg aaggtcattt tctccttctg tatgagctaa     1260
atctcagtgt ctctagaatt aaagagactc cagggatgga acttttgatt tagggtgtgg     1320
tgaagggacc cacacataca gttagactca cagcccctt actggaaagg taataaagta      1380
tttaattcat tttggtctct agacaatcaa ccttctccca ctgaccaccc acctctgttt     1440
cctgaattcc caaagcaaa agaaaaccaa actgctaagc aactgcctag agcaagacat     1500
gtatgttcag ctgccaacac ctagagcaaa cccattccaa gtggagaatg accaaaaaat     1560
cttgattatt tcttgacctg tgtcaagtat gttgaaagcc tgccaaagtt tcctcatttc     1620
tattgaagca ctcttattct ggatgcattt tagaacagtt tgaacagtgt tacattgctc     1680
```

```
agaggtgaag aaaattgctt tgtagtttaa ggatatttaa gatttgtttg tttgtttgtt    1740
tgttttctgt cccaccttct acaaattgca cgatagatac ctcagatcag gaatgctgca    1800
tgaaaaagta tgtccataat gcaggagatt agactaaatg actcttaaga tatc          1854

<210> SEQ ID NO 19
<211> LENGTH: 674
<212> TYPE: DNA
<213> ORGANISM: Homo sapiens 2.E.20

<400> SEQUENCE: 19
gcggccgcct tcccttccca ttcactggct gcctcctttg tgaactaatg actgtaatta     60
ttacctccca gagctctttt gttatctcca accccaagcc ccggagaggg ggaatgggct    120
ctttagtgaa atgaaagtca ttacaaagca aattaccgtc tagggaggga cagccttcag    180
gaaagacaaa tcagatctcc atctgcatct gaagtagggt gtgtttaaat aaaaaatgta    240
aatatcacca ttagatccaa agtactccag agctgtggga tttaatggag tttaaacggt    300
agcacttgaa gccattgctt taccaaaaag aaaaaaaaat cagttaaatt caggtgtttt    360
aatccgtttc ttctttgggg gttttgtgtg atttaaacgc ttgcttttaa gaacctttat    420
gttttcaacc actcatccat agtagaaaag ttctgcaacc ctagactgct ggcttgaagg    480
aaaacctttg caggatttga tatggatttc aacaaagaac cagcctctgc gaggctggag    540
agagctgcgg agctgccatg cctgaagtgc agatggctga accacaagtc tttaggtttc    600
cggagttgtt attgtggtga cctagagtgt cagagccagg agagcaagaa agaggagcca    660
aactgagccc tgag                                                      674

<210> SEQ ID NO 20
<211> LENGTH: 676
<212> TYPE: DNA
<213> ORGANISM: Homo sapiens 2.E.24
<220> FEATURE:
<221> NAME/KEY: n
<222> LOCATION: (493)..(493)
<223> OTHER INFORMATION: a or g or c or t
<221> NAME/KEY: n
<222> LOCATION: (505)..(505)
<223> OTHER INFORMATION: a or g or c or t
<221> NAME/KEY: n
<222> LOCATION: (508)..(508)
<223> OTHER INFORMATION: a or g or c or t
<221> NAME/KEY: n
<222> LOCATION: (533)..(533)
<223> OTHER INFORMATION: a or g or c or t

<400> SEQUENCE: 20
gcggccgcag acgcgccagg cccgccaggg cgccgcacgc cgggcgcgcc acgatgtcca     60
cgaagcccac gatggacagc aggaaggcgg cgtcggtgtc gggcacgccc gcgtccttgg    120
cgtagttcac cagcaggatg gcggggacga agagcccgag cgccatcagg aacttggtga    180
cggcgtacac ggcgaaggcg cggtcggtgc acactgccaa gtccagcagg cgccggcggg    240
gccggaccct gggggatgcc tcgcgcagct gcagccccgc accgtcagcc tccgcctcgc    300
ccggagcgtc cccggcgcgg tcgccggcgc tgtccctgcg cggtcgcggg ccggcccgg     360 gcggcggcct catgacagcc ccgcaggcgc agcagtgcag caggagcccg ccgagcagca    420
ggaagccgcc gcgccagccg aagcgctcca gcagctgctg gccgagcggc gacagcgcgg    480
acaggaacac ggngctgccc gccgncgnca gccgttggc cagaggccgc cgncgctcga    540
agtacagccc cagcatgatg agcgacggct ggaagttgag ggcaggccc aggcctgcgg    600
```

```
gcgaggcggt gctgtgccgg ggtccccgga gagcccctcc ttgggcccca caggagggag    660
gggccaggcc ccggaa                                                    676

<210> SEQ ID NO 21
<211> LENGTH: 455
<212> TYPE: DNA
<213> ORGANISM: Homo sapiens 2.E.25

<400> SEQUENCE: 21
gcggccgcgg ctgggggcgg ggagggggc gcaggacccc aagtgggggt cccggagcca     60
gaggcaagtg tcctggggtg ctggggcgc cgtgccggcc gggccgctgc cctggcctag    120
gctggtccgg gggctagcgc gccggggct gcggccgatg gcggggcga ggggccgcgg     180 gggtggcgag ccgggggggc acgggggtcg ggggtgcccg agggggcgcg gccgggcggg    240
ggtggccagg gatggggtc actggggca aaggggatcc agtggggggg tcccgatgga    300
ggcgtgcagg gccaggggcg cccgaggcgt cgggggtcg ggtgccccag actggtggcg    360
tcagacaggc gtgggtcgtt gggggcctgg gtcgcggctt gactgagggc ccggccgggg    420
ctgtggggcg tcaggagagc gtggggtgtt atggg                               455

<210> SEQ ID NO 22
<211> LENGTH: 156
<212> TYPE: DNA
<213> ORGANISM: Homo sapiens 2.E.30

<400> SEQUENCE: 22
gcggccgcgc ttcgacgacg acgacgactc cttgcaggag gccgccgtag tggccgccgc     60
cagcctctcg gccgcagccg ccagcctctc tgtggctgct gcttcgggcg gcgcggggac    120 tggtggggc ggcgctgggg gtggctgtgt ggccgg                               156

<210> SEQ ID NO 23
<211> LENGTH: 978
<212> TYPE: DNA
<213> ORGANISM: Homo sapiens 2.E.37
<220> FEATURE:
<221> NAME/KEY: n
<222> LOCATION: (712)..(712)
<223> OTHER INFORMATION: a or g or c or t
<221> NAME/KEY: n
<222> LOCATION: (819)..(819)
<223> OTHER INFORMATION: a or g or c or t
<221> NAME/KEY: n
<222> LOCATION: (938)..(938)
<223> OTHER INFORMATION: a or g or c or t
<221> NAME/KEY: n
<222> LOCATION: (956)..(956)
<223> OTHER INFORMATION: a or g or c or t

<400> SEQUENCE: 23
gcggccgcta cagtgcgtca acaggcgctg taatccgagc gcataaacga ggggtccggg     60
ggtgggggcc cggggcggcc gtggcagtgg cccggggctg gcagcccgct ttgaaaatct    120
ggcgaagtcg gggagcctgc gtttgctttg gcagctgcga aggcgcacag gtgcacgggg    180 gcgggggct ggctggcggc gccaccaccg accgtcactg acagagcctc gccatgggcg    240
cccaaattcg ttcacttgcg aattgcgtaa gcggccctcc ggtacccaac ctctgggaat    300
tacgcgggct tgtgcctgtg gccaccttgc taggccccac cgctccagcc tgaactccca    360
ccgctccctg ccttgcgctt gatgttccag caacttcgaa ctgtttttat ctcctgtaaa    420
ccaagccgct tctctccttg acgctggcct tcctgcctgg cttgccctcc cgccttcttt    480
```

-continued

```
tgccttttaa gaccgggcag ctatcccacc ccgccagtat atgcccctct tctgggctcc      540
ttggcttcct gtttatacct acgtgactgt gcttactttt ttgcacatgg tttttcttat      600
ccttctgtaa gtttcttgaa ggtaggagcc atgtcttacc ctgccaagca cattgtctgg      660
cacgtagtag ctgttcagta gaggaagtgg tcccttccc taaagggctt tncgtctcac       720
tggagagaaa ggctagcctg gtaccaggga ctgccgagat caagtgatgg cagtacgtgc      780
gattcgatgg tgccgaaagt gacctagaga ggcagctgng agtgctctgg tgctcgcgga      840
tagagctttg gcgatattgt catttacaat gaggactgta ctctgagacg tggaccttct      900
aacagaccat tataaccttt gctctggagg agtgagcnag caacggactc tgacancatg      960
ttttgacaat gggtattg                                                    978
```

<210> SEQ ID NO 24
<211> LENGTH: 321
<212> TYPE: DNA
<213> ORGANISM: Homo sapiens 2.E.4

<400> SEQUENCE: 24

```
gcggccgcac cggctcgggc tctgccaagg gacccggcct gccccaatgc cgccggcggg      60
cggtgcccgg tcgaccctgc acctgactgc gaggcgcggg aaatgaccgg gtctgtcagc     120
ctcccatcgc ggcttccgtc tacaggtact acctgtgctc tgtccagcct cagccactgg     180
acgatccttc ccgtagccgt aggaaggggc ggcgcttcct tggaggggat attagaggcc     240
cgaattcgcc cgggaagcgg cgggagggcg ggggtgccgg aaggagggga ggggagaagg     300
agtgagggaa gtgggtgtat g                                               321
```

<210> SEQ ID NO 25
<211> LENGTH: 1023
<212> TYPE: DNA
<213> ORGANISM: Homo sapiens 2.E.40
<220> FEATURE:
<221> NAME/KEY: n
<222> LOCATION: (628)..(628)
<223> OTHER INFORMATION: a or g or c or t
<221> NAME/KEY: n
<222> LOCATION: (651)..(651)
<223> OTHER INFORMATION: a or g or c or t
<221> NAME/KEY: n
<222> LOCATION: (830)..(830)
<223> OTHER INFORMATION: a or g or c or t
<221> NAME/KEY: n
<222> LOCATION: (837)..(837)
<223> OTHER INFORMATION: a or g or c or t

<400> SEQUENCE: 25

```
gcggccgcgg gctgggggcg agcgcacacc ccgcgccgct ggagttcact gccgggcgcc      60
ggcatgggcc tggggagggg gtgcacaggg cccggagggt gcgtgggtgt ggggtgcgcc     120
cggaggagag cgaggctgcc agagtgcgtg tgccgactga gccagtgtga gtgtgcaggg     180
gctggcggag agactgggag cgagtgtgtg tgcatctaac cgggaggttg tgagtttgtg     240
tgcgcgcacg cccgcagaga agttgtgagc ctgtgtgtgc acctaacaca gaggttctaa     300
gtgtgtgcac ttgtatgtgt gtgtgcacac gcggacagag tgattgtaag gatatgtgtg     360
cacctcacag agaggtttgt gagattgtaag ggtttgcgca cctaacggag atgttgtgag    420
tgcttttttt cctgacaggc tgtgagtttg tgttgtgtgt attagaggtt tgtatggacc     480
tgactgaggg gttgtggaat gtgtgtgcgt gagcatgagc ctggagaggt tctatgcctg     540
ttcactcctg acagagtttg tgagtgtgta tgattgtgtg actacaccac ccaactggcg     600
```

```
gattgaatgt gttgtataca tctactgnga gggcgtgtgt gtgtgtaaat tgtatacaat      660
gaggctgtgt gcatcagtgc acctaaccac gaacctgtgt gtacagatgt gtgtgccttt      720
ctgtgtatca gacatgaggc catgtgtctg ngtgtgttta gttggttgtg caagtgctgg      780
agtctggggg ggagagaggc agttcggagc cttcccgctt tctccttctn cactctntgc      840
ttgtctcggc caccagcatg ttggaggact acaaggctgc ccttcaggcc ctttagaccc      900
gcttaaggca cttgtgatcc tatatgccag atgccctccc aaagtgccag gctaccacat      960
ggcttggctg attgattggc attgaccacc catttgttct ttgcttcctg ggcgggtcat     1020
aaa                                                                   1023

<210> SEQ ID NO 26
<211> LENGTH: 964
<212> TYPE: DNA
<213> ORGANISM: Homo sapiens 2.E.61

<400> SEQUENCE: 26
agccacatgt gtacccatct tcctcctctg tggaaggcgg aaggaaacag atgccctcca       60
aatatggaca gctgaaatga tgaagtgctg aagccctggc ccagaccctc agagagatgt      120
actcaaccac ctccccaccc ttggacaagc acaaaaccag agaaaacaaa ggccagcaac      180
tgtggctcag cccgcataaa tttcttctgg acactggcct gtctatttga atatctgtaa      240
tgtttggtgg agtcaggggt gagggtctca gcctttggct gctgcatctc cagacaccaa      300 tcatgggggtt cttttctttt ttttaatttt tttttttttt ttggaaccgg attccaaggg     360
gccaatttaa gttaacttcg gcttccaagg ttcaaggcaa ttcttctggc ttaaccttcc      420
aaagtggctg ggaataccag gattgcacma cmatgccsgg ytaattttkgw attttwagka      480 raracarggt ttytccatgt kggtwaggyt ggyctmaaac tytsgacctm aggwgatcca      540
cccgcytsgg cctccmaaag tgctggratt acagsswtga sccaccgkgc csggcccatc      600
atggtcttac taatgggtat tttcccctta acatgtcatt tgagcccctg cctgctcatc      660
agtaaactgg gctaattaat aataccctcc tgtagggctg ttgtaagaat aaaatggact      720
atttgagaaa agggcttaac aacagggtat agtgacagag gactcggtaa ctgcttttttt     780 gtgcttatta agagagaata ctacagcaac ctatgggaag atttggagtc acgaaaacct      840
gttctccgtc cttggagcca cagctggact acatttccca gccttccttg cagctgggca      900
tggtcacatg actgtgctcc agccaatgga atgtgaatgc aagtgatatc aagcttatcg      960
atac                                                                  964

<210> SEQ ID NO 27
<211> LENGTH: 748
<212> TYPE: DNA
<213> ORGANISM: Homo sapiens 2.E.64

<400> SEQUENCE: 27
gcggccgctc cgttgactgc agggccccgg cggtcttcct ccgctgttcc gaggccgttg       60
agggctgatg tgctccatcc tcccacttgt ggtttggcaa gccatccagc cgactacaaa      120
cccacgtttg tgagttacct gctggctgtg acgcttccgt caaatctgag taacagtttc      180
ctcatctcta agatgggtaa catagtatct acctcacagg atcgtgtggg cagtacatgc      240
atagaaagga tttaacacgc agtgtactca gctagtttta ttatttatcc gtaatgatca      300
tttgttcttt tcccctaact gtgcctcaca agcatgaaac agaatccacc aaacatttag      360
gtctgggtag tggttggatg gaaacccatc gcgggttaac gcttccaaca ccagtccctt      420
```

```
gacactctcc cgccgaggag gctgatttgt aaacttgctg agaagagaat acccagcaga    480
tctttcaggt ttcaaatcca cgttctttac aagttgtgtt aattgtttgt atatgctttc    540
gatatagagt ctctaggaag taatactagt acatgtttta aaattcaaat actgccaaac    600
agtgagatgt aagtctccct cctaacttct gtttcccaaa tcccatgtcg tttcttctga    660
tgcaatagac attgtatgtg tgtgtgtcta gatagataca tatgtgtatc tctcggcttt    720
ttttttttct tttaaagagt aaaccaag                                       748

<210> SEQ ID NO 28
<211> LENGTH: 250
<212> TYPE: DNA
<213> ORGANISM: Homo sapiens 2.F.2

<400> SEQUENCE: 28
gcggccgccg gggaagggcc ctggaagagc aggaccaggc agagcgggcg ctggggtctg     60
cgctggagct tgcgctgagg ccggggtctg gccaggagcc gcagttgcag ccgctgctgc    120 cgcaggtgtct gaggatgagg ctggagccgc agcgggaacc ggagccgcag ccggtgctgg   180
cgttggcgct ggaactgagg ctggggccgc cgccgggact ggggttggcg tggccggagg    240
agcacttact                                                          250

<210> SEQ ID NO 29
<211> LENGTH: 657
<212> TYPE: DNA
<213> ORGANISM: Homo sapiens 2.F.41

<400> SEQUENCE: 29
gcggccgcgt acggacagcc agtgcattag gcagggctcc cctacgcgcc cggagagcgc     60
ggaccgctgc ctcgggccgg cgccgcctcc tgccgcctgc cgccgctcgc ggagcccgag    120
ccccagcccg agccgccgcc taccccaggc cggggcgtcg agcagccggc ggcctgtcca    180 tgtgggcta gccctcgcgc ctggcctgca tcaggaccag caacatggag gcggccgttt    240
gcgaccccga cacgcgagga ccagggcggt gcggagcccc gcgaggacgc gacgcccatg    300
gacgcctgtc tgcggaaact gggcttgtat tggaaactgg tcgacaagga cgggtcgtgc    360
ctgtttctgg cccgggcgga gcaggtattg cactctcagt ttcgccatgt ggaagtcaga    420
atggcctgta ttcactcgct tcgagagaac agagagaaac ttgaagcgat tatagaacga    480
ccatttgaag gaattttaaa gcgcttcgga aattcacagg aatgggtatg acaaatggaa    540
aaaagagccc tttctcttat gtacaggaaa gatttattc ctaaactgga gccaaaggtt    600
ctttctcaca gtaactgaa aatattttcc tgaaaggggt tactggtgtt tttaaat       657

<210> SEQ ID NO 30
<211> LENGTH: 318
<212> TYPE: DNA
<213> ORGANISM: Homo sapiens 2.F.50
<220> FEATURE:
<221> NAME/KEY: n
<222> LOCATION: (39)..(39)
<223> OTHER INFORMATION: a or g or c or t
<221> NAME/KEY: n
<222> LOCATION: (84)..(84)
<223> OTHER INFORMATION: a or g or c or t
<221> NAME/KEY: n
<222> LOCATION: (189)..(189)
<223> OTHER INFORMATION: a or g or c or t
<221> NAME/KEY: n
<222> LOCATION: (223)..(256)
<223> OTHER INFORMATION: a or g or c or t
```

<221> NAME/KEY: n
<222> LOCATION: (256)..(256)
<223> OTHER INFORMATION: a or g or c or t
<221> NAME/KEY: n
<222> LOCATION: (260)..(260)
<223> OTHER INFORMATION: a or g or c or t
<221> NAME/KEY: n
<222> LOCATION: (261)..(261)
<223> OTHER INFORMATION: a or g or c or t
<221> NAME/KEY: n
<222> LOCATION: (279)..(279)
<223> OTHER INFORMATION: a or g or c or t
<221> NAME/KEY: n
<222> LOCATION: (296)..(296)
<223> OTHER INFORMATION: a or g or c or t
<221> NAME/KEY: n
<222> LOCATION: (297)..(297)
<223> OTHER INFORMATION: a or g or c or t
<221> NAME/KEY: n
<222> LOCATION: (305)..(305)
<223> OTHER INFORMATION: a or g or c or t
<221> NAME/KEY: n
<222> LOCATION: (317)..(317)
<223> OTHER INFORMATION: a or g or c or t

<400> SEQUENCE: 30

| | | | | |
|---|---|---|---|---|
| gcggccgcgg agcgattgca tgcaggggcc gcgtaccgng aagtgcagaa gctgatgcac | | | | 60 |
| cacgagtggc tgggcgcggg cgcnggccac cccgtgggcc tagcgcaccc ccagtggcta | | | | 120 |
| cccacgggag gaggcggcgg cggcgattgg gccggcggcc cgcacctaga acacggcaag | | | | 180 |
| gcaggcgggng gcggcaccgg ccgagccgac gacggcggcg gcngcggagg tttccacgcg | | | | 240 |
| cgcctggtgc accagngggn ntgcccacgc ggtcgcagna tgggcgcagg gcaatnncaa | | | | 300 |
| aacancactt gggcccng | | | | 318 |

<210> SEQ ID NO 31
<211> LENGTH: 525
<212> TYPE: DNA
<213> ORGANISM: Homo Sapiens 2.F.59

<400> SEQUENCE: 31

| | | | | |
|---|---|---|---|---|
| gcggccgcct cccgccagga agggtggcgg gcccggaagg ccagagatgc cccagtgctt | | | | 60 |
| cccgcgccgc tacgcaccta gctgcccgcg ggtcccacat ggctgcggcc ggagggtccg | | | | 120 |
| caccaggacc gccgccgcct ggggaagcgc ttccctgtgg gcaggcgcg gcgggcagtg | | | | 180 |
| cggaagcccg aaagctaccg gagcccgggg caggggcggc gcgatgcaga ggcggcgttc | | | | 240 |
| gggggccccc agctgcctgc ggctcggcta cccagccgcg atcagagggg gcgggggacg | | | | 300 |
| caggaacccc ggcgtccggg cggtgtgcag ccgcagacct attccaagtt tccacgtagt | | | | 360 |
| tgcgagagcc caaaaactgt cacgtgcacg tcgctgctga gtgggaggag gtgtttgtca | | | | 420 |
| tcgcgttcaa aagggggcgtt tcggtgtctc ccgtcatgca agcaaatggt atggctctcg | | | | 480 |
| gccgcctttg aataaacgag tgcttcgaac cctttaccag gaggg | | | | 525 |

<210> SEQ ID NO 32
<211> LENGTH: 1032
<212> TYPE: DNA
<213> ORGANISM: Homo sapiens 2.F.70
<220> FEATURE:
<221> NAME/KEY: n
<222> LOCATION: (687)..(687)
<223> OTHER INFORMATION: a or g or c or t
<221> NAME/KEY: n
<222> LOCATION: (689)..(689)
<223> OTHER INFORMATION: a or g or c or t
<221> NAME/KEY: n
<222> LOCATION: (885)..(885)

<223> OTHER INFORMATION: a or g or c or t

<400> SEQUENCE: 32

| | | | | | |
|---|---|---|---|---|---|
| gcggccgcgg | ccgggggggct | gagaagggcc | tgggtgcctg | tcgcccggga | gccgaggttt | 60 |
| cccggcctcc | cccgacccccg | ggcgccaaga | gcagtcggtc | ccccggcct | ccgccggca | 120 |
| aaggggccct | ggggcccagg | cgcgcggcc | ctgcgtggcg | gcaggcggcc | caggccagcg | 180 |
| ccggcggcta | gagaaggcct | ccagtccagg | cctcatggaa | gggcctgcct | cgagcggccc | 240 |
| ctcaacgccc | cgcagtgtgg | cactggaagg | gacctaaaaa | cccacctggc | tttctccttt | 300 |
| ccccttcccc | acgcttccca | gggcccaatg | cccgcatctc | agtttcgctt | tccggcaggg | 360 |
| tcagggtga | gagggaggaa | ttctcaggtg | tcacctcctc | acccgcctgg | aggcggaggc | 420 |
| tagaaagacg | tcgggcact | ctggagggga | ggaagaggtg | tgcctagaat | tctctctctt | 480 |
| aaacgctcgc | gttatcacgg | aggagacttt | ataaacactt | taaacacaac | accaaccatt | 540 |
| ttatcagcaa | aagcgagggg | agggggcgt | acagtaaatg | ctgagagatg | ttcgagaagc | 600 |
| cccaagacgt | tccctgcgga | aggagaacgg | aagaaagaaa | ttacgggcgg | aaaaagagta | 660 |
| aatattagct | ccacacctaa | ccacttncnc | agccccaaac | taggagagaa | tctgctaaga | 720 |
| ttcgctttat | atttatatag | tctatgtgat | gttaacaata | ggggttgcaa | atattgcatg | 780 |
| ggggcattct | tagagtaaaa | aattggtatc | tacctgaaat | tcaaaaattt | aactgggcat | 840 |
| cctgtatttt | tattggctaa | tcctgcaatt | ctaactaaaa | aacancttgt | gaagaaatca | 900 |
| tatagaagga | agctaattgc | tgatgaatac | agtattggga | actgttatgg | aactggctgg | 960 |
| aaagaaatga | ttctctacga | tactttgagc | catgtaggtg | agagagatga | tgagcactgg | 1020 |
| atgtctacta | tt | | | | | 1032 |

<210> SEQ ID NO 33
<211> LENGTH: 708
<212> TYPE: DNA
<213> ORGANISM: Homo sapiens 2.G.10

<400> SEQUENCE: 33

| | | | | | |
|---|---|---|---|---|---|
| gcggccgcgc | ccaggcgccc | cttccctgt | ggggcaaccc | aagccgggga | cgcgtgaacc | 60 |
| acctccgtag | ccgccccgcc | agcaccccca | gccgtgcgcc | cctgcaccac | gcagctgccc | 120 |
| tgcgcatgga | gcccagaggg | acagcaggcc | cggccccag | caccaccggc | ctgccgggag | 180 |
| gttcgggaaa | ctggcgtcgc | agcggagagg | gcatcaggcc | aacgcctccc | ccgaggctca | 240 |
| gctgcgggct | cccaggcgta | ggcacccacg | gcccttacgc | tgaccgtagc | ttggacgccg | 300 |
| ctgccgccgg | ggtccaatgc | cggtcatgcc | catcccgcgg | gggttgtgct | ccttccatgg | 360 |
| tccacacacc | acctgcctgc | atgcggtctg | tgggcccgtg | ggcgcctccc | acctggcccg | 420 |
| caccaagtac | aacagcttcg | aggtgtgcat | caagacgcgc | tggctgtagg | gcttcatcca | 480 |
| cttcctgctc | tacttcagct | gcagcctgtc | actggggcac | gctggccgcc | ttcttctgcc | 540 |
| tgcagtactt | gggcgttagc | gtcctcctgt | gcttccaaca | caagctgtgg | gtgctgctgc | 600 |
| tgctgcttgg | cccgctggcg | cgttgaaatt | tcgctgttga | acgagctgct | catctacagc | 660 |
| atccacgtca | acatgcttgt | tgtatggggg | cctgggctgg | atgcctaa | | 708 |

<210> SEQ ID NO 34
<211> LENGTH: 569
<212> TYPE: DNA
<213> ORGANISM: Homo sapiens 2.G.108

<400> SEQUENCE: 34

```
gcggccgcac acgtgtccag gcgtcacgtc cgcgcgcgcc cccggggctt gcgtcagcgg      60
ctgttccaga agcgggtggg ccagggctct gcgcaccgct ggggttcggg gcccgggacg     120
ccgccgggag gagggcaccg cgcggggtcc gacgcggagg cgtgctcgga acgccggggg     180
ctgcggagtg catcagcgcg gtccagccct ccgcctgccg ggcgccgagc gtctccgccg     240
cccggacctg ggctgggcgc cgtggcgttg cctcggagct cgctgcccgc ggggcgcgca     300
ccgccttgac ccgggcggcc ccgcggcagg caggcgcccg cagttccatg gttggttcgg     360
agcgcgatga gccgcccgtc ctccaccggc cccagcgcta ataaaccctg cagcaagcag     420
ccgccgccgc agccccagca cactccgtcc ccggctgcgc cccggccgc cgccaccatc      480 tcggctgcgg ccccggctc gtccgcggtg cccgccgcgg cggcggtgat ctcgggcccc      540
ggcggcggcg gcgggccggc ccggtgtcc                                       569

<210> SEQ ID NO 35
<211> LENGTH: 916
<212> TYPE: DNA
<213> ORGANISM: Homo sapiens 3.B.30

<400> SEQUENCE: 35
gcggccgcgc tgagctcact ccgggccctg cggaaagaat tcgtaccgtt cctgttgaac      60
ttcctgaggg agcagagcag ccgcgtcctc ccgcaggggc ccccgacccc cgccaagacc     120
ccgggcgcct cggcagcctt gccagggagg ccgggaggcc ccgccgcggg tagccgcggg     180
gcgcgcagcc agcttttccc tccgaccgag gccctgagca ccgctgccga ggcccctctg     240
gcccgccgcg ggggcaggag gcggggcccg gggccggccc gcgagcgtgg aggccgcggc     300
ctggaggagg gggtcagcgg ggagagcctg cccggagccg ggggccggag gcttaggggc     360
tctggcagcc ctagccgccc cagcctcacg ctgtctgatc cgccaaacct cagcaacctg     420
gaggagttcc ctcccgtagg ctcggttccc cccggcccta caggggtgaga ctcagctctc     480 atgcaggaga tgggtaccac gaaggctctg gggagtcagt cattcgagct cggcgctccg     540
cagtggagcg ccaggatggg tagaaggctg ggggtgatgg tgagggtttt tgtgggttt      600 cttcgcagcg gccatgctct gccccgtggg ccgtcatttt gtcgtttcgt tttctctata     660
atgtaataac taactaggca aaagtgtta aaattaataa ctactaaata tccgatgtca      720
ttacaacatt tataatatat aacaatatta aaacatataa ttaataataa aaaaaacctt     780 atttttaatct ttttcttttt gttaatttat atcaccttat ataccatttt tctcaatacc    840
attcgataca atcataaatt tatttattgt atattgtcaa aataaaatat tcctctatat     900
aaaaataact ctccta                                                     916

<210> SEQ ID NO 36
<211> LENGTH: 998
<212> TYPE: DNA
<213> ORGANISM: Homo sapiens 3.B.36

<400> SEQUENCE: 36
gcggccgcag catggctttc ggccactact cggagcactg gaaggtgcag cggcgcgcag      60
cccacagcat gatgcgcaac ttcttcacgc gccagccgcg cagccgccaa gtcctcgagg     120
gccacgtgct gagcgaggcg cgcgagctgg tggcgctgct ggtgcgcggc agcgcggacg     180
gcgccttcct cgaccgagg ccgctgaccg tcgtggccgt ggccaacgtc atgagtgccg      240
tgtgtttcgg ctgccgctac agccacgacg acccgagtt ccgtgagctg ctcagccaca     300
```

```
acgaagagtt cgggcgcacg gtgggcgcgg gcagcctggt ggacgtgatg ccctggctgc    360
agtacttccc caacccggtg cgcaccgttt tccgcgaatt cgagcagctc aaccgcaact    420
tcagcaactt catcctggac aagttcttga ggcactgcga aagccttcgg cccgggccg     480 ccccccgcga catgatggac gcctttatcc tctctgcgga aaagaaggcg gccggggact    540
cgcacggtgg tggcgcgcgg ctggatttgg agaacgtacc ggccactatc actgacatct    600
tcggcgccag ccaggacacc ctgtccaccg cgctgcagtg gctgctccct ctctttcacc    660
aggtaaagcg ctctgggagg cgtgggccag gtcttttctc ctctgaaaar ggcggagtag    720
agacagaata tgctgagttt gcaagcaggg ccccsggttt ggggtttcgc tccaggtccc    780 caccccctcaa aaccaagaat cgcgtcggta arggractca cagtgagggc tgcgacacgc    840
gcacgcgccc cacccagcgg tgccccgaac ccctccggtc yyctatctkg yytctatcgt    900
cccctcmcyt gcttkcgagt gagaacacat ttgcaaagac ccctccaccc ccggaaaaa    960 caagagtttt taaatgcttg gagatgagcc ctgatatc                            998

<210> SEQ ID NO 37
<211> LENGTH: 514
<212> TYPE: DNA
<213> ORGANISM: Homo sapiens 3.B.55

<400> SEQUENCE: 37
gcggccgcgg cgctgttggg ccagcagggc agcaccgagc ccgacttggt gccgcagtac    60
tgcgggggac tgcgggcgcc ccagcccgac gggtcggcgt agtagccgag cgggcggcca    120
gtgcagcctg cagcctgcag cggcagcgcc ttcacgcccg ccgccgcgta agagagcagc    180
gtggccgcgt tgcccgcgaa gtccgtggcc gtgtcatagg ccgaggccgc gaagtccagc    240
cggttgttgg ccggcgtcac aaaccagcgt tgcggcgagg gcgcgcccgg gtcctcggcc    300
tgctgcggcg acagcagccc gttggtgtgc ggcacgctgc ggtccgtacc ggcccggggg    360
cccgcgcccg cgcccgggtg gaagcgggcc ttggcgtagt tgctcacgaa ctggtcctgc    420
aggaaagagc cggccatggc gtagcgggcc ccgggcacga tctgcgagcg cggcgagtcg    480
ttgggcgagg gggtcaggcg gtccatgtca cagc                                 514

<210> SEQ ID NO 38
<211> LENGTH: 608
<212> TYPE: DNA
<213> ORGANISM: Homo sapiens 3.C.01

<400> SEQUENCE: 38
gcggccgcgg cgcagcggag gggctgcggg cccggaaccc aggccggtca gcgtgtaagc    60
gccccagccg gccgggctcc gtgggggtc agctccctga cccctacagc gcggtagcgc    120
ctctccgaga gctccgggac cagcggcccg gccgccccca aagccagcct ccctctccct    180
tccccgcacc gggatcccag accagggagg gggcgcacgt ccgacggctg aggaatagca    240
gggcgcgagc cggccggca ggtgcccatc gtcgccctct gggaccccgg tggcgcgctc    300
tgtcctccgc gccacgctca gccaccaccc cggctgtttg ggaccggca ccagccgag      360 cgcgccgccc cctcggggac ccgctggggcg gggctgagcg aggcttggag tgcgggcgaa    420
gggacgtggg gcgaacccgg ggcgctgcgc cacctcggct gtctccagcg gagaccggcg    480
ccctcgcccc ccgtctccgt tcattgtgct gtattcatcc agcagatttt gaaacaattc    540
tcgtgtaaaa aggcatttta ctccgcgcgt cttccttaca gccatttagt tgggagtttg    600
cggtgggc                                                              608
```

<210> SEQ ID NO 39
<211> LENGTH: 1025
<212> TYPE: DNA
<213> ORGANISM: Homo sapiens 3.C.16

<400> SEQUENCE: 39

```
gatatcctcg ctgggcgccg ggggctgcag ctcgctctgc tgctgctgct ggtagaagtt      60
ctcctcctcg tcgcagtaga aatmcgsctg caccgagtcg tagtcgaggt catagttcct     120
gttggtgaag ctaacgttga ggggcatcgt cgcgggaggc tgctggagcg ggcacacaa      180
agcgggaggc agtcttgagt taaagggtc ttggtgcgra aacctggcgc agcgcgcagt      240
gcgcgccaca gtcccgaacc tctcccttg cagagctatc ccctaaagcg ctgggtggt       300
cttggtgggg gaataaaggg agcacccttt cacccctttt ggacagtccc ctgctatctc     360
ggagacgcac ttagtgaacc agcggcttgg tgcccgccga gccccgctc ccccgggagc      420
ccggagcgca agcccggga gtcggccccg cagcggcaga ggaatcgaaa tcggccctgg      480
cgcccttaag aagccgcggg aggtggcggt gaggaaaaca atttgccaaa atccaaggca     540
caaagttttg cgccacctga aggagaaggc gagaggcgcc tgggcgctag cggctgcgtg     600
aaccccgctc cgcgccgggg cccctccgct gcggctgttc ccactcgcgc cctagccgct     660
ctcctacccc cgccggcacc gcagcccctc ccaaccttcc ytytccaccg scccgtccc      720
caccccagt accgccccg tccaacactc cttttgccag cttttcttct ttctctcgcc      780
ggctggagtg gcgagctcag ccgcgggctt taacacccct ccataaatac argggggtg     840
tcaaataata ataggggcac ctcccttcgc actcaatacg gagatgcaac tgcgccagag     900
accccgctgc gatacctccc ccggagccac cccaccaagg gtagcagctg ttctggaacc     960
gcccagagcc ccgctcctcg cagttcctyc gcatctcggg cgcgaggaca cccgagggcg    1020
gccgc                                                                1025
```

<210> SEQ ID NO 40
<211> LENGTH: 1010
<212> TYPE: DNA
<213> ORGANISM: Homo sapiens 3.C.17
<220> FEATURE:
<221> NAME/KEY: n
<222> LOCATION: (829)..(829)
<223> OTHER INFORMATION: a or g or c or t
<221> NAME/KEY: n
<222> LOCATION: (875)..(875)
<223> OTHER INFORMATION: a or g or c or t
<221> NAME/KEY: n
<222> LOCATION: (906)..(906)
<223> OTHER INFORMATION: a or g or c or t

<400> SEQUENCE: 40

```
gcggccgcgg accgacttcc ttcgccggcc accggaggga gggggcgccc ctaccccggg      60
aggggggctgg gcgagccggg agacggtcaa gttgggtcg ggggagcgcg ggcgctccgc     120
actctggggc acgcggggac gagcccggcc gcattgtctg cgcggcctcg gaacaagcac     180
ggccggcggt ggcaccggcg ggcgcgggga ggagttgccg tccccttcg ccgccgccgc     240
ccaccgcgtt cttttgtgtgt ctctcgccgc cctccagccg cttcgccgct cgcctgacag     300
ctgatgggct caccgcgccg ggtcccgcgt cctctcggcc gcagcggcg gagcccggcc      360
cggcaggagg aggaggggag aagaggagcg ttgacagatg ctgtcttgga gcgggcaccg     420
ccgggggaaa agtctggact gcctcggcga gaagcggccg gtaggcaacc ggccccagcc     480
```

| | |
|---|---|
| tcgcattcgc ctcaaagacc ccaattggct aggagccctt ccctccgcag cggctcgcgc | 540 |
| agctccgctc ttgcgccccg cgcccggctc agcggacgga ctagcgcgcc cggtcaagaa | 600 |
| tcctggggaa cccgctccgc ccctggctc cagcgccctc caatggatgt cggcgtacag | 660 |
| aggggctgtt ccgcccaatc aggtgtcggg aagcccagcc agtccccggg gagtgtagcc | 720 |
| aatagaaggc gacttcggca cacccgcc ctgatccact aggacaaacc gctcgagccg | 780 |
| gggtggtgga ccgatcctga ggcagatcag ccagtccgcc aaactgtgng caagtagatc | 840 |
| tgagacggtc cgtgttaatg actatatcta agagntggat gggaacgggg cgcccaattt | 900 |
| tccctngtat acgcttttgg caagttgggt tgaaaactga caacctgagc tgttaatgag | 960 |
| gcttctttaa ctgtttatgc tatacgccta gtggctcaga caacgttttt | 1010 |

<210> SEQ ID NO 41
<211> LENGTH: 413
<212> TYPE: DNA
<213> ORGANISM: Homo sapiens 3.C.30

<400> SEQUENCE: 41

| | |
|---|---|
| gcggccgccg taaagcgcgg atgcgcggcg tggccacgcc ccttcagtgc ttgtgacgca | 60 |
| ggcgccctgg gcttttgggg cgcgaaaaag aagcagtcct gggttgtacc cggcgcagct | 120 |
| gggagcggct gcttcctccg gggtcgtatc tccgcccggc atgggctgc tggacctttg | 180 |
| cgaggaagtg ttcggcaccg ccgacctta ccgggtgctg ggcgtgcgac gcgaggcctc | 240 |
| cgacggcgag gtccgacgag gctaccacaa ggtgtccctg caggtacacc cggaccgggt | 300 |
| gggtgagggc gacaaggagg acgccacccg ccgcttccag gtatgcaggg acccgccccg | 360 |
| aagacgaccg gctgcgcggg cctcccccta gacttttggc taccgggccc cgc | 413 |

<210> SEQ ID NO 42
<211> LENGTH: 927
<212> TYPE: DNA
<213> ORGANISM: Homo sapiens 3.C.35
<220> FEATURE:
<221> NAME/KEY: n
<222> LOCATION: (595)..(595)
<223> OTHER INFORMATION: a or g or c or t

<400> SEQUENCE: 42

| | |
|---|---|
| gcggccgccg ctccttgcct gaccgcttgc tccccgcccg cccgcccgcc gggttgtcgg | 60 |
| cgcggggcca ctggcgggtc gtgatgagca ctcgctcgcg ccccgcacg cacacgcgaa | 120 |
| acccggcccg gcccgccgcg ccgccccgcc tctcgcactc ccggagctcg cccaccggcc | 180 |
| gcgctggctc acactctccc tcacagcacg ccggccgagg gaggaagggg gcggtccggg | 240 |
| ctcccgaggc gtggggaggg ctgtttattt tgggggagg aggggcgcga ggcaggaacg | 300 |
| agctgactgg ccgggatcct ccgacccgcc actgtggcag caccgggaag gcggggagag | 360 |
| agaaagaggg agggagggag ggaccgggat gtagaactcc agcccgcgcg ggaggctacg | 420 |
| gcgaggggg cggtggcggc ccgcgggggg ggcggtgcca ggccccctcg gcaatctccg | 480 |
| tagtctcctc gctggctgcc cgagggaggc cggaagcga tcgggaagc tcggaatct | 540 |
| ccggcacggg cctgggattg tcctggaggc acagcgcggc tggagtgcgg ggcancgcgg | 600 |
| gggggcggg gtctgtctcc tttctgggcg gggccgtatc ctgaagcagg cggggcttga | 660 |
| gagacccgaa agccacggag tggctcctgc ttgcggtact agttggacag agtaaagtcc | 720 |
| tggagttacc tcgcctgagc accctggttt cccgagaggg aatgggcact ctgtgagagg | 780 |
| caagctattt gcctgctttc cctccgcaga agaaaaaagg ctcaattgga aggtggagga | 840 |

| | |
|---|---|
| tgaagccacc ctctatggtc accccaatct gagagcttta ctttatataa ctacattcta | 900 |
| aggagtagta aaatacccga ggtggaa | 927 |

<210> SEQ ID NO 43
<211> LENGTH: 1365
<212> TYPE: DNA
<213> ORGANISM: Homo sapiens 3.C.64

<400> SEQUENCE: 43

| | |
|---|---|
| gcggccgcaa ggaccggctg agarmtgkgg gscsctgtgc tgggggcgsg arggagrcgg | 60 |
| ccytraggac tgcscsccccc ccacaccggg gcccggcgg gacacacgcc caacgggacc | 120 |
| cctgagcccc caggctgggg accgcaggg gctccgggga ggctggtgag gccaggacgg | 180 |
| agccgccycc acgcgtagcc gtgaagcggg aggtacgcgg ccccctggag ctgccccgac | 240 |
| tgcagccgag ggcgcgacct gtggtgccaa ccgcctgacc ctgcttggcc gccgccgcct | 300 |
| gcgggtctcc agcaggtccc acccccacgcg cccgcggggc ccgctccaga ggctcctcca | 360 |
| aggccgctgc agaggcgcgg ccaggctccc atttctgcgc atccctggcg ctcagacacg | 420 |
| gcctgagccg ggtacccggc gactcccttc ggcctccacc gcctcctggg gagggaccgc | 480 |
| gcgctgctcc cacgcgggcc cggggggtctc cgcagcccctg gcctgggtgc gtccgtcggg | 540 |
| ctgctcggct cggagcaccc cccgccccgc cgccccacca gcgcctytyc ggagcgctca | 600 |
| ccccgccccc gactcgtgtt gttgttgcgt gggttttttc tctaattctc cggagttact | 660 |
| cttttgttgc caattgtttc tatgcccgga ggccacgctg taaatgagat gttacatctg | 720 |
| caccgagcta agtaaacact ttataaatga ataaataagt gaataaataa cgaaatcgtc | 780 |
| atctcggggc ggcccggctg ccagggctcc ggccgccggc ctgcggggt ctgtgtggtc | 840 |
| ccgggccctg ccctgggggtc ggggaggcgc cgggaggggc cgtttcccag ccgtgtccct | 900 |
| accctgaccc catcttcctt cctctcccaa atcatcctcc agactctggg cgtttggtcc | 960 |
| ccagatgtcg tgtgggattc gtggcttcca cccaccgctt ctcaaacaaa aacgggttgt | 1020 |
| caccgcggct cttaaccctg ggcgagccac ggagcgtttc ttcccgggat cgggatcggg | 1080 |
| ccgcggctcg aaccggcatc tgcagaagga agacccggcc ctgtaggccg ccgccgcccc | 1140 |
| aggaccggac tggtggcctc tccacgtcgt gtccggaccc gacwcatcgc ctccaacgcs | 1200 |
| aacaaacgga agcagcggag cctccgcctc cmasscykgc cyctgyscgs yswgmcmggc | 1260 |
| gcattsragt gcwcsakkym sgcycaatym mgagagckct gracktckca aytatcwcgg | 1320 |
| actarsrrsr rcawwtkmww argsactcay tgagtaactg atatc | 1365 |

<210> SEQ ID NO 44
<211> LENGTH: 608
<212> TYPE: DNA
<213> ORGANISM: Homo sapiens 3.D.21

<400> SEQUENCE: 44

| | |
|---|---|
| gcggccgcac tgccctggcc gccacgctcc gcgcctgcgc cgcgcacctc aggggcccgc | 60 |
| cgagagggcg gggaggtgac gaggtgaggt gggggcaggg agcgggctgc gcgaacgcac | 120 |
| cgcacacgcg gcctgggagg gaccaccggc ccgcagcccc gggggaggcc cagcggcccg | 180 |
| cgcccccctgc cggaggcctt gcgccgccgc agtctccctc tgggccggga agagcccctc | 240 |
| ccgagcccg agggcgatcc cacccctctag gattactcca cgccaggcgg ccagcgaatt | 300 |
| tatcccgccc gcctccaccg cccccttcaag ccctggggaa ctgggagaaa cgtggcgcgc | 360 |

-continued

| | |
|---|---|
| agcggcacct tccccacgct gctcctcaag ggaaaggacg cgagtggtct tgcccaggtt | 420 |
| aggcaaggca gatggcatct cagaccccga agtgtgccag ccgcctgttg gggacagaga | 480 |
| ggccgaggac ctcgtcacgg ttttactgag gccacaccag agaaccacct agggctagga | 540 |
| tgctgccctc agggcaagag ggtgaaacct gaagactgcg agtcgttgtt gagtttcacc | 600 |
| cgattcct | 608 |

<210> SEQ ID NO 45
<211> LENGTH: 1947
<212> TYPE: DNA
<213> ORGANISM: Homo sapiens 3.D.24
<220> FEATURE:
<221> NAME/KEY: n
<222> LOCATION: (748)..(748)
<223> OTHER INFORMATION: a or g or c or t

<400> SEQUENCE: 45

| | |
|---|---|
| gatatcatct attttaaaag acatatgtaa aacccaaccc ttaagaaagg attcctatca | 60 |
| ctgttcccca caggcatcct cctcagtctt acacctttcc acccccaaa acaaatcatt | 120 |
| cagcatattt atttcatact gtaatatagg aaatagctat tttttagact ttttatatta | 180 |
| ttagcactga tcatacaaac atggaataga aattccttat gttttatctg gatttaaggt | 240 |
| gatacataat ggaatatatt tctatcaagc cgtacacatt agagataatg aaatcacttg | 300 |
| tgttctagtt taaacattat gggaatttca gaactgcaac ataacaaata atcctcggat | 360 |
| gaaaactaaa tctctcctct ggtcaggcat ctatgtgcat cagwgatgag aagacaggga | 420 |
| ctgtggaagg gaaaacagcg agtcaggaag gactgtggcc acgtccattc cctggtccct | 480 |
| caagtaatta aatcctgacc tcctctaccc cagtctgtcc tggggaatgg ccaacactgg | 540 |
| cctttcacaa ctgtgtgtta ctagaaatgc aacagaaacc cagctgaatc ccctcctctg | 600 |
| cccttctcaa aggaaagatc tgtcccagga ccatttgttc caacattttc aattatgaga | 660 |
| actgggaaga taaagttatt tttacattta taaagaaaca catatttatt cacmctcatt | 720 |
| wcaagraagg tcaagaatct atmcaaanac caagaggaat ttttaaaatc ccataatwcc | 780 |
| accatcaaaa gagccacact tagcatgttg gtccacaggc ttctttagca ccctcttyyg | 840 |
| ttggtgtatg cacaaaatgc acaatcacat tctgtctaca ttttataatt tgcctgtttg | 900 |
| ttgattamca ctatatattg aacaattttt aagacctgca acatatgttg acaacattac | 960 |
| ttccaaacaa tgtatttaca aataaatgca cacacacact atctgtctta tatacaacgt | 1020 |
| gtcttacttt ctaattctcc actcttgaag atttaggttt ttccaacttt ttcttaatat | 1080 |
| attcaccagg agtcagcaac ttttttccat aaaaggccaa agagtaggcc gggcgcagtg | 1140 |
| gctcacgcct gtaatcccag cattttggga ggccaaggcg ggcagatcac gaggtcagga | 1200 |
| gatccagacc atgctggcta acacggtgaa accctgtctc tactaaaaac acaaaaaatt | 1260 |
| agctgggtgt ggtgagtgtg gcggcggaca cctgtagtcc cagctactcg ggaggctgag | 1320 |
| gcaggagaat ggcgtgaacc cgggaggcag aggttgcagt gagccaagat cgcaccactg | 1380 |
| cactccagcc tgggcgacag agcaagactc tgtcacaaaa gmaaagaaaa aaaaaaggcc | 1440 |
| aaagagtaga tattttaaac tctgcaggcc ataggtttct gttgcaacac tcaactctgc | 1500 |
| tgttgcaggg aaagaagcca tacacaattt gtaaatgaat gggcatgact gtgttcttcc | 1560 |
| cgacatggtt tgccagcccc tgatgtataa cactacagag gatgctgtta gaatgaaawt | 1620 |
| tctttacata tctctgatga tctccttagg actaattact agacatgaca tcatggtagc | 1680 |
| tgtgggtcaa agggcatgca tgctctggga tgtacattcc cagattgctc atcatgagcc | 1740 |

```
tttctcatgt caaaatgttt tgtgaccacc agaaaggctg gttctgcttt tawtacccat    1800
ggawtgagga atagaaatga catggcatgg cccttcccca cagcaccacg gcttctcttc    1860
ctcagcacgg cgacagggc ttccccttg ccgccgccgc ccgccaagct ccgccgccgc    1920
cggccaagct ccgccgcgcc cgcggcc                                        1947
```

<210> SEQ ID NO 46
<211> LENGTH: 1637
<212> TYPE: DNA
<213> ORGANISM: Homo sapiens 3.D.35
<220> FEATURE:
<221> NAME/KEY: n
<222> LOCATION: (612)..(612)
<223> OTHER INFORMATION: a or g or c or t
<221> NAME/KEY: n
<222> LOCATION: (715)..(715)
<223> OTHER INFORMATION: a or g or c or t
<221> NAME/KEY: n
<222> LOCATION: (1014)..(1014)
<223> OTHER INFORMATION: a or g or c or t
<221> NAME/KEY: n
<222> LOCATION: (1265)..(1265)
<223> OTHER INFORMATION: a or g or c or t

<400> SEQUENCE: 46

```
gatatcttct gataaagaac caatctgcct gggagtttca aatctgaaaa agcaaatcat      60
agtttactgg agtaaactgc tgtttaaaaa taaagagaa aggaaaaaaa aagaatgtt     120 tcctagttcc agaactgaca actagagcct aaataaatac ctggacaagg gtaaatatga    180
cctcaaattt ataaccgccc tgaacgcaga acatcaaccg cgacagctgt ggcatcagcg    240
gcgacagtaa ttttctccct ggcattcaac cagagggcag ttggactgtg caccgactgc    300
actagtggtg ggtagccaaa gctagcctcc aaagtgaacc acggtctggg gcctggtccc    360
gtttgaccga aaatgctatc cagaacmccc wycgagactg caggcccttc ttcctgattg    420
agctagaggt gagtgaagac agggtctggg gtagggaggg gcgtccacgc cagcttgccc    480
attacctgcc ggccttggtg atgatcatct cagtgcctat ctcatgaaag cgcttccaga    540
gctcggctcc ctgcagatcc acccgcgggg cctgcgcga gggcagaggg gtcccgggcc    600
gggccaggga gncgcgccgg agaccccttg ggggaagcct cccggtgacg ccagagggga    660
agctccytgc tggaagccgt cctcacagcc gcctggacag caaaggacag agaanaggra    720
actggtgagg gaaaacagag gggaagcmag ccgcggagac ggsccccacct ggtggctgag    780 aagargaaaa tgaccgggag aaaaggggaa gctttggtgc catcaggtcc tcctaaagaa    840
caagccagtc gatagacacc cacattctgc ctgtcgaagg ggcgcattca gagctccagt    900
gtggcctgct tggtccccaa gtcccaagcc cggrakaggc gygcggsmag cgtccacmcc    960
accccgctgk gcctccgcag gkcsarggcm cmasmaraaa aggcttcacg ccgnccgccg   1020
gggtctggga cgcttgcccg acggagtcag agragctccc sggtcmagag tccacagtgc   1080
aaactycgac gcaacctgcg ccttgaarcg caagcagcaa aagcgcccsg cactctgktc   1140
ccaagagcyt gggcctcctt aagccataag cgtytgcggc gcctcgcttt kggccttctt   1200
ttgggccggg ccggaggmat cttctagaar gctcttyaga acmccgcttt ygycaaactm   1260
ycggncgccc tgcgcttcca rcccarcaga agaaagtgt gaaaagcaag cccgcggtcg   1320
ccgtcggcct tggcagagaa atcaagagga gaagggaagg gaaccgctca actacccttc   1380
gggaaaccaa gtttccaaat atgccgccct cttcctggtt tgcacaaacg gtttagggca   1440
ttcgttccgg tttcagggtg gggtatgccg tcgctcccct cctccccgcc ctgtgctttt   1500
```

-continued

```
aaaagttagg aaacaaaaaa gagcacccat tggctggaac cccaagggag gcagatgcag   1560
gaagcacaga gctgcaccgc taggcgcagc aaacagccgc ggccgaaggc gcgggtcgcc   1620
gagtgggcgg cggccgc                                                 1637
```

<210> SEQ ID NO 47
<211> LENGTH: 900
<212> TYPE: DNA
<213> ORGANISM: Homo sapiens 3.D.40
<220> FEATURE:
<221> NAME/KEY: n
<222> LOCATION: (671)..(671)
<223> OTHER INFORMATION: a or g or c or t
<221> NAME/KEY: n
<222> LOCATION: (702)..(702)
<223> OTHER INFORMATION: a or g or c or t
<221> NAME/KEY: n
<222> LOCATION: (739)..(739)
<223> OTHER INFORMATION: a or g or c or t
<221> NAME/KEY: n
<222> LOCATION: (746)..(746)
<223> OTHER INFORMATION: a or g or c or t
<221> NAME/KEY: n
<222> LOCATION: (752)..(752)
<223> OTHER INFORMATION: a or g or c or t
<221> NAME/KEY: n
<222> LOCATION: (762)..(762)
<223> OTHER INFORMATION: a or g or c or t
<221> NAME/KEY: n
<222> LOCATION: (782)..(782)
<223> OTHER INFORMATION: a or g or c or t
<221> NAME/KEY: n
<222> LOCATION: (816)..(816)
<223> OTHER INFORMATION: a or g or c or t
<221> NAME/KEY: n
<222> LOCATION: (837)..(837)
<223> OTHER INFORMATION: a or g or c or t
<221> NAME/KEY: n
<222> LOCATION: (867)..(867)
<223> OTHER INFORMATION: a or g or c or t
<221> NAME/KEY: n
<222> LOCATION: (874)..(874)
<223> OTHER INFORMATION: a or g or c or t
<221> NAME/KEY: n
<222> LOCATION: (879)..(879)
<223> OTHER INFORMATION: a or g or c or t

<400> SEQUENCE: 47

```
gcggccgcgg cccggaccag ccgctcccac ccgccccagc tactacggcg cggcgcgacc     60
gcgggctccg gccccagccc aggcacgtgc gcccaggccg cggggaggcg ccggcgcctc    120
ccggaacgcg ctcctggcct gcgagtgctg cccgctcagt ctccgggtgg gaagtgcgct    180
cgccccggac cgaggggaaa gcccaacatc cccgggatgg aacagagagg cggccacccg    240
tgagtgggcg tgacccattg gttcccttgc gcagcatctg tggagaatta ggctttcccc    300
tcctctcttg ccagccgttg ttcctaatct tgtctttttt aagggaggaa agcaggagaa    360
ctcatgacac tttgtatcac aggaaatcaa gttggtggag agagggtttg ctgacctctc    420
ccgtcccttc tcagggtccc taggagaatt tttgaagaag taatcggcag caggagatg     480 ggggcaatag agagtctcag actcgcaggg acccatgttc gtccccagcg ccactacttt    540
caaaccgtta tccctcagag ctgtttcctc acctccacaa caactctccc gggttcgatg    600
acactatata tccccaccagt tcatcttggt acaggcaaaa aggtaattca aaaagcgaaa   660
cgaatctcat nttctgacct gtgccctcgg taaagtcccc angtttccac cccaagtaca    720
cttggaagcc aggcccctnc acacangctg ancaccacct tncacaaact gaaacaaag    780 anaatcccctt ggtttcaaag ttagaatagg gatacngcgt gagtggggtg aattgcnatt   840
```

```
gggtcaagga aaaaaaaaaa gtaaatnaat taanttttnt tgacctcctg cgctgcccac    900
```

<210> SEQ ID NO 48
<211> LENGTH: 1511
<212> TYPE: DNA
<213> ORGANISM: Homo sapiens 3.D.44

<400> SEQUENCE: 48

```
cgggcgcggc gagccccact ttctcccggc aggaaggggg gaggccgaga gcatttcctg     60
ttgtgcagct gagccctgcg gagacgtcat tgcattcatg ctccctcggg tgtcagcgga    120
cggggggcca aagttcaagc cgcgtccagg gcaggcagcg cgcggcggcg cggcggcgcg    180
gggcgggcgg ccagggctcc cctctcccgc tggcgctccc ggcgcctccg tccccggccg    240
gcccagcgct gctaccggag gccagccctg gggctccgcg gggaagagct gctcttcctc    300
ccggaggaaa ccgagctcgc aagcccagcg ctcccagccg cagactgcag agctccagta    360
aggtgaaagt aggcaagaag gcccctgag acgtttctaa aagcatattc tatatgtttt    420
cattatgaaa acacccactg cactccttt attattagg accttaagtt atcctatctc    480
aactaatact tttaacaatc agaatctctt aagaatcttt caatcttata cttatccact    540
ttaatagcca acaaaacctt tagccagagt gttttaaaat ggaaattacc tgttcatgtt    600
tcttaaagat ttttaaagtc tccttctaaa tttccagcct tccatttagt ttcaagccat    660
aaaccagatt ataacaatgt gtaattgtag agaagctgtg gcttacggtt aataacgatt    720
aaaaataagg ccataaggta ttttatgatc attttgaaat aaaaaattga aatagtttaa    780
tttcagcttg tgcagtttga gacagatcgt caactacaaa acaaattgta gattctgttc    840
tcatggtgaa caaacattac agatgtttta ctgtgtcaac atctctaaca tttgaactaa    900
gcaatgtttc acatcagaac atgaattaaa acaatgtaaa ctatggaccct ggggtgacca    960
tgatgtgtcg atgtaggttc ttggattata acaaatgtac cactctagcg caagacttcg   1020
atagtggagg aggctgtgtg tatgtgggga caggaagtac atgggaaatc tctgtacctt   1080
ccgctggatt ttgctgagaa gctaaaacta ccctaaaaat ataaactcta ttttaaaca   1140
tatgtttagg gttttatgag tatcctgata cttaaaatgt gcattgcatt gtaacctatg   1200
aattgacaag aaattaatct taagaattgg cacagaaatc atctcgatgt tttcatgaag   1260
ttcatcctcg gttctactgc ttcttgataa acaagtttca tgtttagaag gttactgaaa   1320
tttttttata tggtaaaggc acatcaaaga ctttaccatt taatatatat tagttgtcct   1380
atccagtcat gtactatttta aggcaatatt aaaggtaact tagatttccc cacttacagt   1440
gatgcaaagc ccttcaataa tattctgttg tcttatttcc taaacatctg aataatacaa   1500
ctttatcaca t                                                        1511
```

<210> SEQ ID NO 49
<211> LENGTH: 835
<212> TYPE: DNA
<213> ORGANISM: Homo sapiens 3.D.60
<220> FEATURE:
<221> NAME/KEY: n
<222> LOCATION: (607)..(607)
<223> OTHER INFORMATION: a or g or c or t
<221> NAME/KEY: n
<222> LOCATION: (675)..(675)
<223> OTHER INFORMATION: a or g or c or t
<221> NAME/KEY: n
<222> LOCATION: (716)..(716)
<223> OTHER INFORMATION: a or g or c or t
<221> NAME/KEY: n

```
<222> LOCATION: (731)..(731)
<223> OTHER INFORMATION: a or g or c or t
<221> NAME/KEY: n
<222> LOCATION: (732)..(732)
<223> OTHER INFORMATION: a or g or c or t
<221> NAME/KEY: n
<222> LOCATION: (741)..(741)
<223> OTHER INFORMATION: a or g or c or t
<221> NAME/KEY: n
<222> LOCATION: (778)..(778)
<223> OTHER INFORMATION: a or g or c or t
<221> NAME/KEY: n
<222> LOCATION: (805)..(805)
<223> OTHER INFORMATION: a or g or c or t
<221> NAME/KEY: n
<222> LOCATION: (806)..(806)
<223> OTHER INFORMATION: a or g or c or t

<400> SEQUENCE: 49
gcggccgccg cggagccggc gtccgcagcg gctgcgcatc tcgggcctgc agcggggcgc      60
ttggcgggcg gggccggggg gagagcctgt ttgcgcagta cccccggagg gcggaaggcc     120
gccgaggtaa gagccgggac tcggccaggt gggagtgggc accttgggcc gggcctgcag     180
ggcggtcccc gagcgtcccg gggtagggtg ggctccctgg ggacgatgcc cagggccccg     240
gccgcgctcc ggtcgcgccc caccccggct gcagcgcggc cttggggcgc tgctggcctc     300
gccgcggggg tgggagcggt cgcggcctgg agcagctccg ggcgggcccc aggctctggg     360
gccagggcca gctgcgcgca ggggtgagtg agcagccccc gggccctcaa gtgagcccct     420
gtccgctccc caccttgcat ttctcctctc cgcagtgggc gtggcgcccc tttgctgtat     480
aggggcgcc ccaaattgaa gaaggctggg ggggagaacg cataaacagg tgtttagggg     540
gcccaggcct gtgcgccaag ggttgaagaa taaagagtaa ttcttttttc cccttttta      600
aggggggnccg gagtccccct ccccccggc cgtggtaagg gcccccccttt gctccgtaag    660
gggccctcct ttggnaaaac aactccttt tctttttttt attttgtccc ccccncccca     720
ataatttaaa nncctccctg ntcgccccg cccccgctt tttttttttt tttctnaa       780
accccccacc ccccccccccc ccttnnttt gtttccgctt ttattccaag aaaat         835

<210> SEQ ID NO 50
<211> LENGTH: 645
<212> TYPE: DNA
<213> ORGANISM: Homo sapiens 3.E.04

<400> SEQUENCE: 50
gcggccgccg gcttgacgtg tacggcgctg atcacctacg cttgctgggg gcagctgccg      60
ccgctgccct gggcgtcgcc aaccccgtcg cgaccggtgg gcgtgctgct gtggtgggag     120
cccttcgggg ggcgcgatag cgccccgagg ccgcccctg actgccggct gcgcttcaac     180
atcagcggct gccgcctgct caccgaccgc gcgtcctacg gagaggctca ggccgtgctt     240
ttccaccacc gcgacctcgt gaaggggccc cccgactggc ccccgccctg ggcatccag     300
gcgcacactg ccgaggaggt ggatctgcgc gtgttggact acgaggaggc agcggcggcg     360
gcagaagccc tggcgacctc cagccccagg ccccgggcc agcgctgggt ttggatgaac     420
ttcgagtcgc cctcgcactc cccggggctg cgaagcctgc aagtaacctc ttcaactgga     480
cgctctccta ccggcggac tcggacgtct ttgtgcctta tggctacctc taccccagaa     540
gccacccccgg cgaccgcct cagcctggcc ccgcactgtc caggaaacaa gggctggtgg     600
catgggtggt gagccacttg ggacgagcgc caggcccggg tccgt                    645
```

<210> SEQ ID NO 51
<211> LENGTH: 1021
<212> TYPE: DNA
<213> ORGANISM: Homo sapiens 3.E.50
<220> FEATURE:
<221> NAME/KEY: n
<222> LOCATION: (744)..(744)
<223> OTHER INFORMATION: a or g or c or t

<400> SEQUENCE: 51

| | | | | | |
|---|---|---|---|---|---|
| gcggccgcgg | gacggggaga | tgcggccccg | gtattgatgt | cgaaaatgat | ggataacgcg | 60 |
| ggaatggcaa | atatactatt | tgtctaatgg | ctcggcaatt | aaattcccct | gtaaatgacc | 120 |
| catgcctcat | ttcatcctaa | tctatggaat | tttgattgaa | ttcgtcagct | ctaattgaaa | 180 |
| aatactgcac | tttaatgtct | gcattgcagt | ttcaggacga | gagtggtttt | aatgagacag | 240 |
| tgcccccatg | acccgggaat | atttgagact | tttattcgga | atttaaagcc | aggagattgc | 300 |
| tcgactgagc | cctgagattt | cctctcctgt | atccacgtcc | atccatctcc | agacgcgatt | 360 |
| taataaacgc | acttaaggat | aaatgcgccc | ccgaccctcg | cgccaacgtg | ttaccccacg | 420 |
| ggcgcccctc | ctcggaataa | gggacggcgg | aggccgggga | ggcgggggag | ttgggggggct | 480 |
| cagaaggtcc | tggtccctcc | ccggcccaag | tttccctgcc | ctccctgcca | ccctggtccc | 540 |
| caggcactgt | cgcggacccc | agactccgcc | ttccctaggc | caaacctagg | cgacctccct | 600 |
| ggactaggag | gcctggctgc | ctgccacccg | cgcaccggaa | gaagggactc | gcgcactcgg | 660 |
| agaaggggcc | gggccccgac | gcgctttata | tgcaaatggc | gaggcgaagc | catccctgag | 720 |
| aaatagctac | ttgctgaagc | tatntactag | attgaaatga | gttaagagaa | acatttaagt | 780 |
| cgtgcaacga | gataattggg | ccgattaact | ggggatgttt | gctctttcaa | aaaaaaaaaa | 840 |
| aaaaaaaccg | ccgaggagga | gagagcagta | agccgcgttg | attgagccca | ctgtcaagac | 900 |
| cgaattccga | tgcgggacgg | tcctcgggac | tcgaagagac | ccacggagga | ctgagaggct | 960 |
| ttcgccggcc | gcgcatttct | tttcaggcat | ccaccggcca | gggcctagaa | gtccgaaagg | 1020 |
| c | | | | | | 1021 |

<210> SEQ ID NO 52
<211> LENGTH: 518
<212> TYPE: DNA
<213> ORGANISM: Homo sapiens 3.E.55

<400> SEQUENCE: 52

| | | | | | |
|---|---|---|---|---|---|
| gcggccgcag | gaaccacgat | gagaggcagg | agctgctcct | ggctgagggg | cttcaaccac | 60 |
| tcgccgagga | ggagcagagg | gcctaggagg | accccgggcg | tggaccaccc | gccctggcag | 120 |
| ttgaatgggg | cggcaattgc | ggggcccacc | ttagaccgaa | ggggaaaacc | cgctctctca | 180 |
| ggcgcatgtg | ccagttgggg | ccccgcgggt | agatgccggc | aggccttccg | gaagaaaaag | 240 |
| agccattggt | ttttgtagta | ttggggccct | cttttagtga | tactggattg | gcgttgtttg | 300 |
| tggctgttgc | gcacatccct | gccctcctac | agcactccac | cttgggacct | gtttagagaa | 360 |
| gccggctctt | caaagacaat | ggaaactgta | ccatacacat | tggaaggctc | cctaacacac | 420 |
| acagcgggga | agctgggccg | agtaccttaa | tctgccataa | agccattctt | actcgggcga | 480 |
| cccctttaag | tttagaaata | attgaaagga | aatgttg | | | 518 |

<210> SEQ ID NO 53
<211> LENGTH: 498
<212> TYPE: DNA
<213> ORGANISM: Homo sapiens 3.E.57

```
<400> SEQUENCE: 53
gcggccgccc ccacggctcc accctctcgg cggggccgca gccatctggg gcccctgcca      60
gtagcggccg ccttccgctc agcctctggt cccaggcgag cctggcgagc cggcgaagca     120
ccggcgggga ggaggactag aacaggagga ggggcacggc ggattgaagc gagctgggct     180
gtgagcaagg gacacccaca gcctggagaa acagccccgc tctcttgcgc gctgtctgct     240
ccagccgcta ctggggctc taagcagcgc gatgctgctt cgcttcttct aggcggcggc      300
cggcggaggc tttccgcagc cgcttggccg gcgccggccc ctattccgtt ggcaagtccc     360
ttgtctatcc cggagggcgc acccggacgc tcgagccgga gcgagcgcga agtccgaagt     420
ccgcccccag agccgccaac ttccctgtga gcccctctcc ccgccgcagc ctgcgccaga     480
cctgggagcg atgcgccc                                                   498

<210> SEQ ID NO 54
<211> LENGTH: 471
<212> TYPE: DNA
<213> ORGANISM: Homo sapiens 3.E.59

<400> SEQUENCE: 54
gcggccgccc gggcccgcgg gcgggggggat cggcggggggg gacccgcggg gtgaccggcg    60
gcaggagccg ccaccatgga gttccgccag gaggagtttc ggaagctagc gggtcgtgct    120
ctcgggaagc tgcaccggtg agcctggcgg gggtcccggg agaagagtgg gaggatctga    180
ggaggatgct aattcccacc tgggcgcaga ctgacagatg aacgggcgat accccggcat    240 ggggggtccac ccatctgtcc agttttctgc cgtgggctcc gacggcgctg ttctccctgg    300
tcgagccttg tccattatcc tgttcctttt tctgcacccc accccacccg gctccactct    360
ctctggtgct gtaaatgcct ctctcccggg tctctggctc ctcccccacc acttctgggt    420
ctctgtcccc gtctctttct ggatgtctct gccccttttc tctctgggtc t              471

<210> SEQ ID NO 55
<211> LENGTH: 971
<212> TYPE: DNA
<213> ORGANISM: Homo sapiens 3.F.16
<220> FEATURE:
<221> NAME/KEY: n
<222> LOCATION: (905)..(905)
<223> OTHER INFORMATION: a or g or c or t

<400> SEQUENCE: 55
gcggccgccg tgggcctgca aaacttccaa agtagcagcc tgtttctcct cgtctccctt     60
ctcctgggta cccagcgccc cgccttcccc agaaagggcg aggggtgggg gcagggctcc    120
ctcgggaggt ggccaagcgc cgggacgcgc tcccagcgtt actcaggaca cttgggattt    180
ggcctgcagc ccccttcccc atccctggcc tggctgcggt gtcccttgct cccctctgct    240
gctgctcctg ccccatcaag tcgaaaatct gagggtggga tggggtgggg gaccaggggg    300
taccctccca ggccgctccg cagcaggccg aggtggagac cctgcccggt aggcgagtcc    360
ttgtgcccac agctcggagc cagcagcgga gtgacaaaaa agataaagtt ggtgaatgat    420
aaagaccgta ttttccacgc tttgggtgcg ggaccagatg atctagaaaa tgagctgaaa    480
tggattcagc ctccgagcct gttgtgagag cagctgattc ccccatttcg ggccagatgg    540
ctgctgaaca cagatttgca ttcatttttcg cttaatatcg tccaaaatag tggggcagct    600
gcatttgttg tcaaaaaggt ttaaaacccc ttttctttct ggggcaggat cgttacctta    660
tgtgatgggc ttatagaact tttttttcct ctttagtcaa cagtatcaga tttagaagga    720
```

-continued

```
tttgttttta aaccttctaa tttggtaatc agatttaaat cgccttggcg cgtgtaatct        780
gaattaaaga tactgtaaat gattntaagc atgatacttt cgttagcgca aggaaggggc        840
acctctagca caggctggac attttaggaa gtgtgctata aaggagcatt gttcctattt        900
caacttaatc ttccgaaaag gctttggtat tctgcataac gctgctggcg ttgcctggtg        960
agcccgagag t                                                             971

<210> SEQ ID NO 56
<211> LENGTH: 550
<212> TYPE: DNA
<213> ORGANISM: Homo sapiens 3.F.2

<400> SEQUENCE: 56
gcggccgcac gcgggtgcta atttgcacac atcaagactg aagtgtagtg aggaaacgtt         60
gagtttctgt tttcaaacct taacttcgt aattagagat ttaacaactt gaagggggc          120 ggggagaggc gggggaggag gtgggcagaa ggaataaaac tccatctaaa attcctaata       180
gcaattcctt agaattataa actgcgagat gatcagaagt gacatctttg ccttctttga       240
aggctctctt ctctaagtta ctaataatga taatgcacgt tcgggtacag aaatatgagc      300
caagaactca agtctgcaat gaaggagtgg acatgacagc gtaagaggga gcatcattgt      360
ttgatctatt ttaaccttttt ccgtctcaaa gatacgatgg tgcttcctcc aggaagaaaa    420
gcctgtaagc tcaaacaaga gctcccctgg aacagaagac actggagacc gtaagaggtg      480
ggaggttgga aggggaaaa ggatagaaaa actgcctgtt gggtattatg ctcaccacat        540
gggtgacggg                                                               550

<210> SEQ ID NO 57
<211> LENGTH: 870
<212> TYPE: DNA
<213> ORGANISM: Homo sapiens 3.F.50
<220> FEATURE:
<221> NAME/KEY: n
<222> LOCATION: (667)..(667)
<223> OTHER INFORMATION: a or g or c or t
<221> NAME/KEY: n
<222> LOCATION: (684)..(684)
<223> OTHER INFORMATION: a or g or c or t
<221> NAME/KEY: n
<222> LOCATION: (725)..(725)
<223> OTHER INFORMATION: a or g or c or t
<221> NAME/KEY: n
<222> LOCATION: (758)..(758)
<223> OTHER INFORMATION: a or g or c or t
<221> NAME/KEY: n
<222> LOCATION: (776)..(776)
<223> OTHER INFORMATION: a or g or c or t
<221> NAME/KEY: n
<222> LOCATION: (777)..(777)
<223> OTHER INFORMATION: a or g or c or t
<221> NAME/KEY: n
<222> LOCATION: (789)..(789)
<223> OTHER INFORMATION: a or g or c or t
<221> NAME/KEY: n
<222> LOCATION: (845)..(845)
<223> OTHER INFORMATION: a or g or c or t
<221> NAME/KEY: n
<222> LOCATION: (870)..(870)
<223> OTHER INFORMATION: a or g or c or t

<400> SEQUENCE: 57
ttagactctc actgggcagg tctgctgtcc cctctgctcc cgcaggactg gagccaccga         60
gctcgcgcct tcttctcggg gtgcgatttc tctcctcttt tggactcaag atcaatgctt       120
```

```
cccggccggc gcagatcaca cagcaggacc ccaggggaga ctgtggcctt cttcccgcct      180
cccaattccc caagaccgcc tctagaggct gctgtgtccg agaactccg agcattttct       240 ggacacagat tgcctaacag aggaacaggg gttaggtggg gagcggctgg ccggcccaaa      300
cacagcagcc ccaagctggc tcccaagcct gggctctcca ccccgctcc catcctctct      360 tgagcacagt taggcccaac acccctgtcc ccaaaacac ctcctaccct ccctccccc       420 cagccccat cttcaggaac atcacaggc tcacactcac taaccgcgga gagcacatgc      480
aggccggagc cctcagcccg gcagctctcg gaccctgccc agctcgacgc ggactcatgc      540
agaagaggac attccgcagg taggtacaat cccagcgctg gggcctgggg cgtccggggg      600
gcggcctttg agcttccccg ataccgctcg cctgctcccg gagctgttcg gccgacggct      660
gcccggntcg tgcactttca gtanggcccc gctgactcta ctgcccttgg gctaggccta     720
ccggngatgc ccagactcct tgggacgctg gacccgcngc gcgggcggac acgcanngac     780
tccgctctnc gcccggaatc gttgagacgg aatctcagcg gatcccgcgt cgccgagcgc      840
cgggncaggg agaaaggccg tgtggcgctn                                      870

<210> SEQ ID NO 58
<211> LENGTH: 848
<212> TYPE: DNA
<213> ORGANISM: Homo sapiens 3.F.72

<400> SEQUENCE: 58
gcggccgccg cgtcgccgac gcccggcagg actgagcgca cggagcggcg gaactcctcg       60
ttcctccacg tgtagagcag cggattgagc gcggacaggg cgcagcacag gagccagctg      120
gccgcctgca ctccccaggg caccggcagc gagaagccgc tggccaggct cacccacacc      180
agtggctgcg tggccagcag gaagacgcag cagagcagca gcaccgacag gccgctgaga      240
cgccgctgtg cccgccgcgg gtgcagcgcg ggcggcaggg gctgggcctg cgccgggtgc      300
gcggcgccac cggggcccgg cgcgtgctgg gcgcccggga aggcggcggc ggcggcggcg      360
caaccgggca actggtgcaa catgtggaag ttgatcacgc tgacccactt gacacttaca      420
cacacgcagc gcacgatgcc caaatagcat tgcaacaaca tatctgtctg ctccaacaac      480
accacagaag ccatcaacac cagataatgg attctcagtg gcacagcacc cagccccagt      540
gcccaaagcg agaacaacat cactaggccc aaggccagct cccaaaacca caccaacatc      600
cccccctagt gcacctttta tacaacaccc tgtaaataga caaccccca ataataacca      660 attaccattt aaagcccccc aacaatttga aaagaagga caaccgtaat tcccaacccc      720
acacaccacc ccctaaaaaa aaaataattt tcgccaatac cgtcccaatt tttaaaaaat      780
ttcccaaaaa cctctaatcc aaaaacccca acccgccctt cttctatatt tcaaaaaata      840
cccaaact                                                              848

<210> SEQ ID NO 59
<211> LENGTH: 2770
<212> TYPE: DNA
<213> ORGANISM: Homo sapiens 3.F.82
<220> FEATURE:
<221> NAME/KEY: n
<222> LOCATION: (6)..(6)
<223> OTHER INFORMATION: a or g or c or t
<221> NAME/KEY: n
<222> LOCATION: (14)..(14)
<223> OTHER INFORMATION: a or g or c or t
<221> NAME/KEY: n
<222> LOCATION: (15)..(15)
<223> OTHER INFORMATION: a or g or c or t
```

```
<221> NAME/KEY: n
<222> LOCATION: (37)..(37)
<223> OTHER INFORMATION: a or g or c or t
<221> NAME/KEY: n
<222> LOCATION: (38)..(38)
<223> OTHER INFORMATION: a or g or c or t
<221> NAME/KEY: n
<222> LOCATION: (44)..(44)
<223> OTHER INFORMATION: a or g or c or t
<221> NAME/KEY: n
<222> LOCATION: (56)..(56)
<223> OTHER INFORMATION: a or g or c or t
<221> NAME/KEY: n
<222> LOCATION: (76)..(76)
<223> OTHER INFORMATION: a or g or c or t
<221> NAME/KEY: n
<222> LOCATION: (119)..(119)
<223> OTHER INFORMATION: a or g or c or t
<221> NAME/KEY: n
<222> LOCATION: (151)..(151)
<223> OTHER INFORMATION: a or g or c or t
<221> NAME/KEY: n
<222> LOCATION: (170)..(170)
<223> OTHER INFORMATION: a or g or c or t
<221> NAME/KEY: n
<222> LOCATION: (197)..(197)
<223> OTHER INFORMATION: a or g or c or t
<221> NAME/KEY: n
<222> LOCATION: (198)..(198)
<223> OTHER INFORMATION: a or g or c or t
<221> NAME/KEY: n
<222> LOCATION: (236)..(236)
<223> OTHER INFORMATION: a or g or c or t
<221> NAME/KEY: n
<222> LOCATION: (237)..(237)
<223> OTHER INFORMATION: a or g or c or t

<400> SEQUENCE: 59
```

| | | | | | |
|---|---|---|---|---|---|
| atccanatat | tttnnaacct | ctaacaatga | agagtannac | acanactcaa | ttttanaagg | 60 |
| cacaggacct | atgaanacat | tttatggtaa | agaaataca | aatggccatt | tcccacgtna | 120 |
| agatgcatct | aacctcaatg | gtggtcacag | naaaataaat | tacaaaaaan | aaagttttgt | 180 |
| gtgaccatca | gttaggnnaa | ttaaatgctt | cctactaatc | ttttcatgat | aagtannaac | 240 |
| atactagcca | ggcatggtgg | ctcatgcctg | tattctcagc | atgttgggaa | gctgaggcag | 300 |
| aaggatacct | taagctcagg | agtttgaggc | tacaatgagc | tatgatcatg | cactccagcc | 360 |
| tgggtaacag | agagtgagac | cctgtttcta | aataaataaa | taaatgagtg | catgagtgaa | 420 |
| catacataca | tacatataca | cacacggttt | tttacatgtt | tatagagagt | ataaatggcc | 480 |
| aatgaccttt | taaggcacaa | ttagcaaata | tgtattgagt | ggaaagatgc | atgttcttgc | 540 |
| atgcaggatt | ctacctcctg | aaatgcatct | gataacactg | cttgaaaatg | tgtgtagaaa | 600 |
| tgcccacact | agcatgtttg | tggtgggcat | ataaataata | gcaaacaaa | acaaggaaa | 660 |
| aagaaaagta | catatatgtg | aggaaccctt | ttggttatcc | tgggttttg | agataatgtt | 720 |
| catagaagga | aagcaaatca | aatgaagagc | aattgagcag | gaaacggggg | gaaatacccct | 780 |
| cagagtaata | agattatctc | attacactta | agttttgctg | atgcttcaag | tttcctgagt | 840 |
| aagttatgcg | aagcatcttt | ctctgaaaat | cttcttgctg | cagaacaaac | catgtttagt | 900 |
| gtctgtatat | gtctcaactt | cctgtcccca | cctggcggat | gggaaaaagg | acacggtcct | 960 |
| tgcttgtgtt | ttggagtgaa | agaagcatta | aaggtcttgc | agactttacc | aaggattctc | 1020 |
| ctggtctcat | ttcagatcca | acttccaact | ccaggcagcc | tctgtgtttt | tctttaatgt | 1080 |
| ataatcagga | tgtacttcaa | tttggactct | attgctgttt | ggcctgtata | tgcagtttca | 1140 |
| agatagcccc | atacacctgc | ctgcaatgat | ccttcaggaa | tagaatgggc | ttctgagttg | 1200 |

```
aggaatttgg gagtatactg agcccttttgt gtattttttat taagtttctc tattcatgcc    1260
aggagaaggc tgtggacaaa agtaaagga ggagacactg gaattgtgat gtccaaagat    1320
tccaatgttc aaggattatt tgaacccttc acgcctcttt agccaccgcc gccgacagcg    1380
aagacgcgga gaaaaaagtt ctcgccacca agtccttgg cactgtcaaa tgggtcaacg    1440
tcagaaatgg atatggattt ataaatcgaa atgacaccaa agaagatcta tttatacatc    1500
agactgccat caagaagaat aacccacaga atatctgcg cagtgtagga gatggagaaa    1560
ctgtagagtt tgatgtggtt taaggagaga agggtgcaga agcagccagt gtgactggcc    1620
ggggtggagt tcctgtggag ggcagtcgtt acgcgctgat tggcgccgtt acagacgtgg    1680
ctactatgga aagcgccatg gccctccccg ggattacgct gggaggagga ggaagaaggg    1740
agcggcagca gtgaaggatt tgaccccccct accactgata ggcagttctc tggggcccgg    1800
aatcggctgc gccgccccca gtatcgcccc cagtacaggc agcagcggtt cccgccttac    1860
cacgtgggac agacgtttga ccgtcgctca ccggtcttac cccatcccaa cagaatacag    1920
gctgttgaga ttggagagct gaaggatgga gtcccagaag gagcacaact tcagggacca    1980
tttcatcgaa atccaactta ccgcccaagg taccatagca ggggacctcc tcgcccacga    2040
cctgccccag cagttggaga ggctgaagat aaagaaaatc agcaagcctc cagtggtcca    2100
aaccagccgc ctgttcgccg tggataccgg cgtccctaca attaccggcg tcgcccacgt    2160
tctcctaacg ctccttcaca agatggcaaa gaggccacgg caggtgaagc accaactgag    2220
aaccctgctc catccaccga gcagagcagt gctgagtaac accaggctcc ccaggcacct    2280
tcaccatcgg cagggtgacc taaagaatta atgaccgttc agaaacaaag caaaaagcag    2340
gccacagcct taccaacacc aaagaaacat ccaagcaata aagtggaaga cgaaccaaga    2400
tttggacatt ggaatgtttg ctgttattct ttaagaaaca actacaaaaa gaaaatgtca    2460
acaaattttt ccagcaaact gagaacctgg gaattcctgc acagaagaca agagagcagc    2520
ctccccagtt tcagcaagcg ctaggtttat attttttttcc tggttttttac tgtttgggta    2580 atagatattg aaacaagtaa tattaatacc gcatggggag aaccccaacc aaagaaatct    2640
gaaatataaa ataaatgctt ttttttccgt ttttgttcat tttggatgct ggcgctaagc    2700
ctccaagtgt catgattaaa aaaaaaatta tgtccttatt tatttctagg atgaggggag    2760
gataacattt                                                            2770
```

<210> SEQ ID NO 60
<211> LENGTH: 563
<212> TYPE: DNA
<213> ORGANISM: Homo sapiens 3.G.46

<400> SEQUENCE: 60

```
gcggccgccg ccttccgcag taatggttgt tcagcgaaca agatccgggc ggaaacagta     60
gataggcggg tgcagcgggg cagaacatag gttgccttag agaggttccc cggtgtcccg    120
acggcggctc aagtcagagt tgctgggttt tgctcagatt ggtgtgggaa gagcctgcct    180
gtggggagcg gccactccat actgctgagg cctcaggact gctgctcagc ttgcccgtta    240
cctgaagagg cggcggagcc gggcccctga ccggtcacca tgtgggcctt ctcggaattg    300
cccatgccgc tgctgatcaa tttgatcgtc tcgctgctgg gatttgtggc cacagtcacc    360
ctcatcccgg ccttccgggg ccacttcatt gctgcgcgcc tctgtggtca ggacctcaac    420
aaaaccagcc gacagcagat gtgagcagcg gcacacgggt ccgggcaggg ggcaagggct    480
aaggaaggag tggctagggc aggggcggga accggggtgc ttgaccacac gtgaagactc    540
```
agaactaacc caggcagcct gga                                              563

<210> SEQ ID NO 61
<211> LENGTH: 4104
<212> TYPE: DNA
<213> ORGANISM: Homo sapiens 3.G.78

<400> SEQUENCE: 61
gatatctctc tccaagcccc cttcccaact ccatttctgt aggaaagtac agcccctgga       60
attgggttct ggtttcgctt tgggctggag gtgggtggat gggggtcaga gagagaatga      120
ggtgggggg acttcaaggt tctgtcccac cgaccagagt ctgaagacta ttcgcctttc      180
ccaacacgga cctccgccca tccaggcccg ggactatccc ttcgcggtgt agcggcagcc      240
ggagacctgg ctgaggaggc aaccgcgtag acacctccct gcttagaaaa caaacactga      300
accagaccga tcccagttgg agggttcgaa aatgttccag acagcctgtc gggagggtt      360
gttgttgctg ttggactaaa tagctattcc tgattggtca tgtatagggt tttttaaggc      420
gggtgggggg aggaggggt agaggaaagg ctccaaacac ctgcaggttg ggggcggaaa      480
gctgtttgcg attccctgga ctggttggtc ggggacagga ggtaattccc agccattgac      540
ccccatttct ctctctccct ccctcttgcc ctgcctcttt ctctccaccc ctatctttcc      600
tggaaactcg ctttgggcgc ggcagatcgc ccaggaccac accgcagcgt aactgcaggc      660
ctctcagcga aaaggggga aagcaaagac ccgggtgtgc atcctcttcc tcggcttccg      720
ccccttccg gcggagtgga gatcctattc agaggggccg gtctctctaa atatgcccca      780
ggtgagtttt caggggaatg gtgccggtgg aaacggtgtc taggaaggcc ttgtgttccg      840
gcctggggtg aggaaggctc aggacagagg agagcccatt ctcagattgg gggtgggggg      900
aggggaggac cagccagagc ttggaatcgg gatctgactg ctgtagctgc ctctgtggca      960
ttcagcggct ttttcccttt tccacccagg gtaaaaccag ctagttggac ttagtcgtcc     1020
aggccttttcc cattggtccc ggttctgtgg acgtttccca aggccggtaa ctttggggcg     1080
gctgtatccg ggtggtacag actgtgcctg gagctcccgc aggaggaagg cggcagcctt     1140
cctggctagt gcagtcccag ctcgagtggg ccctgatccc aggcctgagg cctagggtgg     1200
ggaggcagga acacccctct tctccggtag aggcgaggat ggtggtgctg ttccctggtg     1260
ggtttggtac ttgtgcaggc ttggggcttc tccagggtgt tgtgctggtg tgggcccaga     1320
agagagacca gaggctgggt ctaagggcct gaggctgttt tcatctaaga aattctctgt     1380
atggggatt gggtctgctt gagacctgtc cccaggaaga atctcctggg gtcttctgtc     1440
ttgttctggc acaggtggaa atattctggc tgtctggcaa ctgcagatga ggatttcctg     1500
ttggggcta taagcagggt ctccgtagta caaagagaga ggagctgtag tcgtcaaata     1560
ctctagaacg attcagtcta aaatctccct cctccttcat tctccccaaa taaaaacaaa     1620
caaaatctct cgggcgttcc tttctgtaat ccaaatcaag tgatgcagct tagtcgccaa     1680
caaccatcag tgtttgtgag tggcttcttt ggggcatgga cctctggctg gtaatcctaa     1740
accggcagga ttttcctaaa atgtggggag gagccgggag aggtcctcca cagatcctgg     1800
gatccaatca tatattcttt acaaggaacc ttggcgatgg gatatttata ggtgtctgga     1860
gaggacattt gtggccaggg tcaattcatc tggaatatgt actcccattg cctctcagga     1920
atccaccgct agagcaggag cctaagaatt aattggaggg taaaaatgtg tcataacaga     1980
gcttgagctc agtctgcaac tgcagtgcac actgtcactc ggttagaagc tgggggcttaa     2040

-continued

| | |
|---|---|
| gcatggatca ctgggctcac accggtgtgt caggacggag agcagtgagg tagggaacca | 2100 |
| atacttgaa gcttgtatgt ttcccagggg ttggtatatt tctggcacat ttcgctgctg | 2160 |
| ctggagcaa gaggacctgg ctgatatact tctggtgcat ttccagtggc cttggtgtct | 2220 |
| tggtggttgc attctatgga tagagaccta ttgtctccac caaaatcata aactcacttc | 2280 |
| caatgaagtg tcagggacct actgccttta cagcttgtat acaccaggac ttagggaatt | 2340 |
| ttgtggtttc tgtgccagac ctgggggggct ggcattccca agaaggtgt acagcagtct | 2400 |
| gaatcttgac tctctgtcat cctgggtgtc tagtggcaat tgagccaagc tccagaggag | 2460 |
| gctgcagatg atccattctc ccttctgggg tgggagggat ggttcctagg atgactcctg | 2520 |
| tccagagcat tgcagtggca gtatgggagc tcaatggctg ctatgtatga tttagatgga | 2580 |
| ctctgcatgg gggtaaattg ttttttttgta tttgttttct tcttttaaat acccaattat | 2640 |
| ataattcaga gagcagaaag cttattttaa acaacttatg tggtgttgat catatatgta | 2700 |
| caactcacaa ctcacaaact ctggcccttg agtctcctga tttttctgtt ttggttcttg | 2760 |
| ctggtgccca gctctatctg gatgaagcca ggtgatggaa gagccccagc acacctgtgg | 2820 |
| gaagtagagt ggctgtggtc atctcggagt atgcttgtgg ggtcacaagg tggtttcact | 2880 |
| gctctgggaa tacaggaggg ttgagcaaag tgagattatt gctctggtct ggctctctca | 2940 |
| cagataggct gtgagtgact tgacattcgg ccaggcagtt ttctcactgg cccattctcc | 3000 |
| ttgttaataa tgtttacttg aacgtttgca cagcactttc aaatgcataa aggaggtatt | 3060 |
| cctcccattt cccaaagaac accaaggcag gagatggcgg tgagggggc tggaagagtt | 3120 |
| caagggcctc atgacatcct gtcctgctct tggatgggag tccagacccc actggcctca | 3180 |
| gggaacccctt caaatgccca gctccattct acctcagcca ggcctctctt tgagactcga | 3240 |
| cctcacttca gagtccagct gagcagaacg aggtggactg tgcagggagg ttgggccagc | 3300 |
| accatcttct tcccttggcg acctctcatc tctgtctgag tgggagtaaa gatccgctgg | 3360 |
| gcgggcagag gactcacagt ggatttgctc agtgtagaca gacactccct cactccccag | 3420 |
| cgggggcgaa tgtgtgtgtg tgtgtgtgtg gagggagctg gttcctcggg attattctct | 3480 |
| gccagctctg gcggagtgga tcccagtccc cgtagcctcc actttctaat tccctacttc | 3540 |
| catccgcacc gggtttctgg gtgtgtgcct gtaggtgggc tgggaatatt gctgagaggc | 3600 |
| caagggaggt tcctaaagca acgaacccct gcctgacaga ttccccgcta aaaccaaaga | 3660 |
| gcacgatccg gaatttgttc cctcctcttc cctttaggcc tgagaaaggg gacagagtaa | 3720 |
| tctctttctt gcctccttgt acatttcctt cctcctgatt tcccttctg tgtttctgtc | 3780 |
| gctggctgta ttccttttct tccggtgtct ctgtcgtctt cctccatctc tgtccttttg | 3840 |
| gccctcagtc tctgtgtctc ccaggcaccc ctccccttctc ccaatccaga gaccctcttt | 3900 |
| ccctcccacc ctagccccaa ccggcctccc gccctagccc cacgtggcgc taactttgtc | 3960 |
| tgcctcttct cacgtctcgg tgcgtgagtt cctctctctg cccttctccc ctttaccca | 4020 |
| gcccacgtcg gtgggtcagg ggcggtcgtc agagcgggca tccgcttgtc tgtctgtctg | 4080 |
| cccacaggat gaccgagcgg ccgc | 4104 |

<210> SEQ ID NO 62
<211> LENGTH: 570
<212> TYPE: DNA
<213> ORGANISM: Homo sapiens 4.B.44

<400> SEQUENCE: 62

| | |
|---|---|
| gcggccgcct gtctgggcgc cgcgctcctg ctcctatgcg ccgcgccccg ctccctgcgc | 60 |

```
ccgggtgagt gcccgccggc cgagccgcgc accccccaacc aaacctggct cctcgcgctt     120
tccaccgcgg cctgacccct cgacagcgcg ggggacacct gttgtctcct tcctggctgg     180
ggctaggggt ggcgggcagg ggcgctggtg cggcacagaa aggctctaga cgccccgcg      240 agcaaaggct cttgctcctc ctccggagtt acctcccccac tcccagagcg gtgactgttt    300
tgagtcccac agccggtgcc tggagaccgg ggtcagttgt gggggtaga ggacaattgg      360 ccaatccggg aaggccatct cccttacctt caccccccttc ccctgcgcac cccacggccc    420
ctggacatga gcgctgctgg gcgcatgcgc ataggagggg aagcttgggc cactcggtcc     480
ggtcccttgg ttgtcctact gtgcagtggg tgccactccc tgctccaccc tgaaatccac     540
actgggtagg gcttgggact cctgtgcacc                                       570

<210> SEQ ID NO 63
<211> LENGTH: 535
<212> TYPE: DNA
<213> ORGANISM: Homo sapiens 4.B.56

<400> SEQUENCE: 63
gcggccgcgc tttctccatg gccccggcct cggcgcgctc ggctccggct cgggggtccg     60
gcacggcagt ctcagtgcgc ggtcgccagg cgcgccgtcc cacccccggct cggcttgggg    120 gtggccccgc gcctccgccg ccgacgcagc tagctggttt ttaaattgct aatctcatta    180
acggcgcgcc cgtccgagag gcgaggctgg taaatggatg acggcgagcc ccaccccgcc     240
cgatcgtcgc ggccgggaag gcacccgaga ttgcagagga cagggcggag tccccctggg    300
tcctccggct cggcggggcc tttcttcagg ctgcggaact cctcgaagtg ggcgccttcc     360
ctcggccact cacctgtcat ttatcgagcg cctactgtgt gccaggcatt gtctggggac    420
acggctgtga accacttccc agctccgtct tggagctgac attctggtag agggaaacac    480
ttgaattgga ctgcatgaaa tgccccattt tcaaccattt tttaatttat agaaa         535

<210> SEQ ID NO 64
<211> LENGTH: 737
<212> TYPE: DNA
<213> ORGANISM: Homo sapiens 4.C.05

<400> SEQUENCE: 64
gcggccgccc ggcggggtta aggcctctca gccaaggccg cggccagctc actgccaggt    60
cgggtcagcg cctgcgcgcc aggtccggcc ttggataccc tctgccgcca cgcgtcggtc    120
cggcctctac gcccgcctgg ccctctgcgc gcgccgccga cgccgcaggt ccgggcctcg    180
gtgactgccg gaggggcgcg gcgccccgcc tcctgtcacc atggccaccg caacccctcc   240
caccgcctca cggccggccg gcatccaatc acaggcgagc gttaccgatg ccggggcggg   300
gcaagacagg gagaggaagt cccggaaggg agtgcggagg gatgcggcgc ttcggcgagc    360
acccgttgtg tgggaactcc gtctcaagtc gcccccattg tacggatgaa ggaatcgaag    420
ccacgagcca gaatttcctc actcgcaact cgagaataaa ttgcgcctcc ctgagtgtgg    480
aggattaaat aagtagttta aggcgtgttt aaagagcgct tgtaagttgc caagtcgctg    540
gagagccagt cccttatccc ttgaaccagg tgatgctgac gtctgatttc aagacagttc    600
ctacccctcg tggaaggaaa gccccatcgc aagaagtcga tgtcctgtaa tttacgttat    660
aatcttcgca tcataaagat tactcggcag taattggttt cttgactaat tataccagat    720
gagaattgaa gactatt                                                    737
```

<210> SEQ ID NO 65
<211> LENGTH: 684
<212> TYPE: DNA
<213> ORGANISM: Homo sapiens 4.C.25

<400> SEQUENCE: 65

| | | | | | |
|---|---|---|---|---|---|
| gcggccgcca | taggaaacac | ctggcagtta | gttcctcaaa | aggttaagcc | cagaactccc | 60 |
| gtaagaaccc | gcaattccac | tccttagtat | agacccgaga | gaaaacatgc | gtccgtccac | 120 |
| gcaaaaatct | gcacacgaat | gttcacagaa | gcatcaggca | taacagtcga | aatgtagaga | 180 |
| caacccaaat | gtccatatgg | atgaactaac | tgtggtccat | ccatgaccgt | aatggaacac | 240 |
| gaccataacc | aggtgtgaag | ttcagctgtg | acagggatga | ccctcgaaca | cggcacgctt | 300 |
| ggtaaaacaa | gcccgatgca | gaacagcacg | attctattta | tgcgcctgcc | acaagaggc | 360 |
| acaccccggg | aaagaaagca | gatcagcact | cccaggaac | cgggacgcag | ggacgcaggg | 420 |
| agggagggac | tgctgaagat | gcacggcgtt | tcttttggga | tgaagaacag | gttctaaaat | 480 |
| cgactgtggt | gatggctgcg | taaatcagtg | aatacactaa | aaaccttact | gaactgtata | 540 |
| ttatttattt | atttattgaa | acagagtctc | gctttctcgc | ccaggctgga | gggcaatcgc | 600 |
| accatctcgg | ctcactgcaa | ccttcgcctc | ccgggttcaa | gggattctcc | tgcctctgcc | 660 |
| tcccgagtag | ctgggactac | aagc | | | | 684 |

<210> SEQ ID NO 66
<211> LENGTH: 1012
<212> TYPE: DNA
<213> ORGANISM: Homo sapiens 4.C.42
<220> FEATURE:
<221> NAME/KEY: n
<222> LOCATION: (793)..(793)
<223> OTHER INFORMATION: a or g or c or t
<221> NAME/KEY: n
<222> LOCATION: (849)..(849)
<223> OTHER INFORMATION: a or g or c or t
<221> NAME/KEY: n
<222> LOCATION: (903)..(903)
<223> OTHER INFORMATION: a or g or c or t
<221> NAME/KEY: n
<222> LOCATION: (921)..(921)
<223> OTHER INFORMATION: a or g or c or t
<221> NAME/KEY: n
<222> LOCATION: (926)..(926)
<223> OTHER INFORMATION: a or g or c or t
<221> NAME/KEY: n
<222> LOCATION: (956)..(956)
<223> OTHER INFORMATION: a or g or c or t
<221> NAME/KEY: n
<222> LOCATION: (1005)..(1005)
<223> OTHER INFORMATION: a or g or c or t

<400> SEQUENCE: 66

| | | | | | |
|---|---|---|---|---|---|
| gcggccgcgg | cggcagcggc | tgcggggagc | tccagcagcg | gcggcggcgg | cggcggcggc | 60 |
| agcggcagcg | gcagcagcag | cagcgacacg | tccagcaccg | gcgaggagga | aaggatgcgg | 120 |
| cgcctcttcc | agacgtgcga | cggcgacggg | gacggataca | tcagcaggta | cgcggggagg | 180 |
| tacgaggaaa | ccgacaggag | cgagatcagt | ccctccgcgc | gcccttgacc | cctgctctgc | 240 |
| cccctcgccc | caacttgcgg | caagttgctc | agaagctcgc | gggaaaagtt | ggccgcgact | 300 |
| ccgagagcgc | gtagccggct | cggccacgaa | ggccgagggg | actgctctgt | tcgccttgcg | 360 |
| ggggtgccag | ttggtccaac | ttttcccagc | gctgtctttg | tctaggcgtt | gggagacatc | 420 |
| tccttaggat | gcgcactctt | ccgggggctc | ggagtgttct | tccctgtggg | aaaaggagtt | 480 |
| ctggccgctt | gtcccaggta | ggaggggctg | ccccacagcc | tcgggtcct | gggcatcaag | 540 |

```
atgccgcagc acggggcagc gatctgcccg gcggcttggt ggacacccca gggccgcacc      600
gggaggagat gagctaagcg acagcctcgg acagggaaat aacctgtgaa gaaactttct      660
tgtgccgcag aacccatgaa ttccaaactt cagagcccaa gaatgggtat cgtttgccac      720
ccagtattga tttaaacgca gtagcctgag aggaacgaag cgctcaggag caaactaggg      780
ctagacccga ctnctacccg gctctgtgcg ctgaccaggt gagcttcggc gtggttccgg      840
gcgcctcgng cctcactaca caacttttg ggtgttgctt cgatccccga cttctacaga       900
gcngattaag cttctgctcc ngctgncaat atactctgcc aattggacta acttgngtga      960
gaagatccac ttctgatgct tgatgtgca cgctgaatgg ttccngatga tg              1012
```

<210> SEQ ID NO 67
<211> LENGTH: 595
<212> TYPE: DNA
<213> ORGANISM: Homo sapiens 4.C.9

<400> SEQUENCE: 67

```
gcggccgcct tgaaggcgct ggacgggatg gtgctgaagt cggtgaagga gccccggcag       60
gtgagctcgc ggcccgccag cccgctgccc acgcagtagt ggaagaggcc gaagtagcca      120
ggcttggggg tgctcacgct gtcgcccacc cagtagggct ggatgaagac caccacgttg      180
atgatggcga agcagatggt gaagatggcc cacagcacgc cgatggcccg cgagttccgc      240
atgtagtgct cgtggtagag cttggaggcc tcctgcgagg gcagcatggt gcccggaggc      300
ggggccggcg gcggcggcgg ctggcggggg ccgccggccc gggacggagc gccgggctgc      360
cgggcgggag ctgggacgc acgcgagaag cggccctgag tcaaggaacc cgcgagggcg      420
gggcctgggg cagagctggg ggcgtctggg agctgctaag ggagagagga aggggtcatg      480
agagtgttga ggccgtgtct aggggggactg gcaaaggtct cctactgggg ggcctaggaa      540
ggggccatga gaaagttggg gggcgcctag gatggggata tgagacctga agtgc           595
```

<210> SEQ ID NO 68
<211> LENGTH: 1955
<212> TYPE: DNA
<213> ORGANISM: Homo sapiens 4.D.07
<220> FEATURE:
<221> NAME/KEY: n
<222> LOCATION: (615)..(615)
<223> OTHER INFORMATION: a or g or c or t

<400> SEQUENCE: 68

```
atatctatcc atatctatac ctacatctac ctgtatgtgt gtagtgtata tatatacata       60
ttatatgtgt gtatatatgt acatatatac atttaaacaa aaatttctcc ttcgtcctcg      120
aagcaaacaa accagcaccc tcgagtgtcc gccaggaggc gcaggggca gcgtgggacc       180 tgcggtacct ccacggttgt agaggtgtag agggatgccg cagcgacgga accgggcttc      240
ttttttaaag aatcaatgtg agggaagggt gcagagccgc gttatttcag ggagacattg      300
tcgcactccc cctcccacgt gtaggtagca tctggggtgc gtgcgccctg ttcgcagacc      360
ccatggagag acgctggcgg cggcagatgg ggctccttc acggttgcag ccggcagtaa       420
cccgaccccg ccggcgcaga gactgaagaa gcgcakggga cagcggcgag ctgcgaacaa      480
aagcccttgg cgcggggccg aagcccakga cgcggtgtga gtaaaccggc tcgggtaccg      540
ggagctgcgg gaacctgggc ggccaggttc tttgcactcc aggagcccac ccactgggat      600
gctgtggggg aactntcgga gggcacccga rggcgggtat ctgaacccg actggggtgg       660
```

| | |
|---|---:|
| atggtatctt tagcacattc agacttggag gagawycggk gcggtctgag artatccagg | 720 |
| caccttctcc atccccagca aaacamccgg tgggggtggw ggtgggggcg gaggcggcgt | 780 |
| gcagagccct cagtaagccc tgccagagct gctggagcaa gaatccatca cccctcccgg | 840 |
| agaggccttt ggggacttct cccagccctt taatcacccg ggggccttgc gaccgagtct | 900 |
| cctttggcag gggaaatcaa ccataaactt cttyccytag gcaaatgggg tcccttggga | 960 |
| tgaacaggcc tcttgctttt ttgttcctgc aaagctgcat ccccagtagc ccgcctaagc | 1020 |
| tacaaacaaa tacgctaatc ctcccgggaa tcctccagcg cctccctctc tagctcctgc | 1080 |
| ctgcacctgg atcttttcat cttaacttgc agcagaaagg ggatgcatct agcgggctag | 1140 |
| gcgcccagag gagcctcgcc acaggcctcc accccgcatt ccgggggctg agggagaccc | 1200 |
| aggctgctct ctgaacacga gtgtccgccc caccccmatc ccsgtyytgg cgctcagcct | 1260 |
| gggctttccg acatcggttt tatgatttac gtyccaccaa agcctctgag cctaatccga | 1320 |
| aagcggatta agttgggatg gggtgactat ggatgaggag gggggaagag ctctcagacg | 1380 |
| tattcctcga tgtccctcct tgtgatctgc agagattcca acaaaggacg gggctcagcc | 1440 |
| atggtggacc cagtgcctga agaagagaag gcaggagcgg aacccggcga ctctggaggg | 1500 |
| gacgaggccg tggcgtccgt gccccctgat tcccagggcg cacaggagcc cgcagcctcc | 1560 |
| tcggcctcgg cctcggcctc cgcggcggtg ccccgcaagg cagaagtccc atgtgcagcc | 1620 |
| gcagaaggcg ggcggcggga gcagtccccg ctgctgcacc tcgacctctt caacttcgac | 1680 |
| tgcccagagg cggagggcag ccgctacgtg ctgaccagcc ccgctcgct agaggcctgc | 1740 |
| gcccgctgtg cggtcaagcc ggtggagctg ctgccacggg ccctggccga cctggtgcga | 1800 |
| gaggctccgg gccgctccat gcgggtggcc accggcctgt atgaggccta cgaggcggag | 1860 |
| cggcgcgcca agctgcagca atgccgggcc gagcgcgacc gcatcatgcg cgaggagaag | 1920 |
| cggcgtcttt tcacgccttt gagccccgcg gccgc | 1955 |

<210> SEQ ID NO 69
<211> LENGTH: 1888
<212> TYPE: DNA
<213> ORGANISM: Homo sapiens 4.D.08

<400> SEQUENCE: 69

| | |
|---|---:|
| gcggccgcca gctcacaaag gatagggagg gatattgctc ttggcatttg atgggaagca | 60 |
| tctgctgcat cccattgggg tgttgcccag gatggattgg aaaagagttg gcaggaaggc | 120 |
| tgagctctgt gctcacaacc tggcttggtg gtggccgagg agcttggcag gagcagagtg | 180 |
| caggacctgg gaactggggg ttggtgcatg tgtgcacgca cgtgtgtgtg tgtgtgcgtg | 240 |
| cgtgctgggg gggtagggag gaagctgtga aaccacatcc cctcctctct gctgctgtgt | 300 |
| tgctgtgtgt ttcagcagca cgtgggtgtc accacacttc ctagcaggtg tcaacctcca | 360 |
| agactgttct gggctcttct cccagttggc tgagttggag gtgggagtcc caactgtccc | 420 |
| ctgtggcttc cagagtggga ccttgctgtg ggataggctg ccaatggtg ctccctcccc | 480 |
| tgtgacccct ctgttgggtg ggtcacgagg aaggactgtg ggtgttgccc acagacaggt | 540 |
| ggacatgtgg caaggacacc ttgggacctt ctttctgacg ccccttgaag ggggcacttt | 600 |
| ctcagctttg agatgagtct ctgtggatgt gggaagttca ctatctcaag agcagcagcc | 660 |
| ttggaaaatc caacacagaa ccccgagtag gggcgggaag gggtcctgtc ccgctcactg | 720 |
| gctgcctggc agagttctgc acaaggaagc gcctgtgttg ctgtgggcgg aggaatggac | 780 |
| tgagggctac attcgcttcc tgttgccgct gtaactgctt atcacaaact cagtggctta | 840 |

-continued

```
aagcaacaga ggctccttcc tttacagtgc taagggtcag aagccgatca gtctcaccgg      900
actaaagtca aggtgttggc agaatccatt cctgcctctt ccagctttgg gtgggaggct      960
ctgctggagt tccttggctt gcggctgcat ccctccagcc tctgcctcca tcctcctaca     1020
gcctcctcct tctctgcagt cagatctccc tctgccttcc tctttttttt ttttgagacg     1080
gagtcaccca ggctggagtg cagtggcaca atcttggctc actgcagcct ccgcctcctg     1140
ggttcaagcg attctcctgc ctcagcttcc cgagtagctg ggattacagg catgtgctac     1200
tacacctggc taattttttgt attttttagta gagacagggt tttgccatgt tggccaggct     1260
ggtcttgaac tcctgaccte aggtgatctg cctgcctcag cctcccaaag tgctgggatt     1320
gcagccatga gccatcacac ctggcctgcc tccctcttaa aggacgcttg tgatttgggg     1380
cccacctggg taatctcttc atctcaacat cttcagttac atctacagag tccctgttgc     1440
cacatgaggt aacacagttt gggaagggag agttattcag cctacccatag ggcctgtgg     1500 tgtatctcag ggcccttctg attttaagat ataaagcaag aaaacaaact ggctcaaggg     1560 gaaaaagga cacgttgaat tctgttgctt taaatgtata ttttttttatt gtgctaaaat     1620 gcacagaaca taaatttgc cattagtaac actgagtaca ttcacagtgt cgtgcaacca     1680
tcagcactgt ctagcgccag aacttttttca tcaccccaaa gggaaacccc gtatccatga     1740
aggactcact ccccattcgc cctctccagc ccttggcagc caccagaatg ctttctgtct     1800
ccataaattc attttttaata agtgcaattc tgtgtgactt taaataaaat aaacatgagc     1860
acgatgagtt gcttattgga aggatatc                                       1888
```

<210> SEQ ID NO 70
<211> LENGTH: 994
<212> TYPE: DNA
<213> ORGANISM: Homo sapiens 4.D.12
<220> FEATURE:
<221> NAME/KEY: n
<222> LOCATION: (673)..(673)
<223> OTHER INFORMATION: a or g or c or t
<221> NAME/KEY: n
<222> LOCATION: (686)..(686)
<223> OTHER INFORMATION: a or g or c or t
<221> NAME/KEY: n
<222> LOCATION: (701)..(701)
<223> OTHER INFORMATION: a or g or c or t
<221> NAME/KEY: n
<222> LOCATION: (754)..(754)
<223> OTHER INFORMATION: a or g or c or t
<221> NAME/KEY: n
<222> LOCATION: (764)..(764)
<223> OTHER INFORMATION: a or g or c or t
<221> NAME/KEY: n
<222> LOCATION: (774)..(774)
<223> OTHER INFORMATION: a or g or c or t

<400> SEQUENCE: 70

```
gcggccgcta ggaaaaggct cagctccggc cgctccgatt agccgtggcc ttgctctgcg       60
agcagataaa cgtgacctcc gtggcctgtg gccagcctcg gccctctgga ggcggggctg      120
tgtgcggccc tccctccccc agcagggctg agctcagaag cagcaggcag ccggaagggc      180
tgggcagtcc ccgcacctgt ccctgtgcca gtctggtggg tgttgtgtgt gcagggtggg      240
cgtgccggga ccctctggcg tggggctgtc tggcaaaggg cgaggggga ggggctgtg      300 cttcagcata gaagggaagg gcgtgtccag aagagggaac agaagagggt ccagaggccg      360
aaccagaaca cgtcccttca ctgatggaaa cttcccaccg cgctcgaatc aattcccaat      420
tgctcgactc ctcgcacctc ccgggaggtc ctgtagaggc agcgctccct cccagcctca      480
```

```
cccgccggcc tgttcctgcc acagggctct gcccttcctg agctctccgc ccggactctc      540
atcccggact ctcctcccca tctccttcca aagccagttc tttctcatta ctcagggctc      600
tgctccaatg ccacctcctc ggaggggcca cctcatcctc tgaacggcgc ccatccctcc      660
ctcctttctc ggngccagct ccattntccc cttctccttt ntcaccacgc ccacaactta      720
gaggcgcgtg tcccgtccct agaactgctg cggncacagg actnctggcc cttngcatag      780
gctggcacgt ggcacgttcg ccccagcctc gtacgcattt tgatggagag ttggaccaga      840
gagggcgcgg agcatgaatc tctgaagagc tgaggagccc aaatcagaag ctggtgagtg      900
agtttaatct gacttggagc atggagttat acgggagctg cttccagaag cccagctctg      960
cactgctacc atatatggca cggacgcttt agct                                  994

<210> SEQ ID NO 71
<211> LENGTH: 677
<212> TYPE: DNA
<213> ORGANISM: Homo sapiens 4.D.13
<220> FEATURE:
<221> NAME/KEY: n
<222> LOCATION: (352)..(352)
<223> OTHER INFORMATION: a or g or c or t

<400> SEQUENCE: 71
gatatctttg ttgcattgag acaggaaagc tattttaaga tggtgtggtg aaaaaggata       60
aaagctcctt actcaagctc tagcttatct aactctcagt caataggtaa caaaacaccc      120
aagaagctgt taactgcaag ctcctatttc agagggctag ggacttcccc agatccccgc      180
ctgtacagtt agacttaaac tccaacctac atttacccct tcctcacttt aatgctaaaa      240
attactcctg gggtggagat ttaaaatgct aatgctacat atgatgtatg aaaaagcata      300
ttgggccact gtgcaagcac tagaaaaact cctcctatag gtgccctgat gntaaccctc      360
ccctatagaa agaccctata aaactgaccc acacactatc ctcagagcag tccgttcctt      420
tgcctttctt ggtgctgact cccttgcgca caagctgaat acactttcct ttgctgctat      480
gtttggtgat ctctgttaat ctctatcatg ggagatcata agaatccagg gcaacagtaa      540
cagcttctga gtttttaaat taaaaataac agtaatataa tccttaaatt tttaaaatgt      600
aggacactaa acaagtaaaa tctaaatcca gagtacatct gacctcaaag ttcatgggct      660
tctcacttcc ctggcca                                                    677

<210> SEQ ID NO 72
<211> LENGTH: 435
<212> TYPE: DNA
<213> ORGANISM: Homo sapiens 4.D.47
<220> FEATURE:
<221> NAME/KEY: n
<222> LOCATION: (11)..(11)
<223> OTHER INFORMATION: a or g or c or t
<221> NAME/KEY: n
<222> LOCATION: (24)..(24)
<223> OTHER INFORMATION: a or g or c or t
<221> NAME/KEY: n
<222> LOCATION: (58)..(58)
<223> OTHER INFORMATION: a or g or c or t
<221> NAME/KEY: n
<222> LOCATION: (59)..(59)
<223> OTHER INFORMATION: a or g or c or t
<221> NAME/KEY: n
<222> LOCATION: (76)..(76)
<223> OTHER INFORMATION: a or g or c or t
<221> NAME/KEY: n
<222> LOCATION: (82)..(82)
<223> OTHER INFORMATION: a or g or c or t
```

```
<221> NAME/KEY: n
<222> LOCATION: (110)..(110)
<223> OTHER INFORMATION: a or g or c or t
<221> NAME/KEY: n
<222> LOCATION: (111)..(111)
<223> OTHER INFORMATION: a or g or c or t
<221> NAME/KEY: n
<222> LOCATION: (125)..(125)
<223> OTHER INFORMATION: a or g or c or t
<221> NAME/KEY: n
<222> LOCATION: (147)..(147)
<223> OTHER INFORMATION: a or g or c or t
<221> NAME/KEY: n
<222> LOCATION: (151)..(151)
<223> OTHER INFORMATION: a or g or c or t
<221> NAME/KEY: n
<222> LOCATION: (156)..(156)
<223> OTHER INFORMATION: a or g or c or t
<221> NAME/KEY: n
<222> LOCATION: (163)..(163)
<223> OTHER INFORMATION: a or g or c or t
<221> NAME/KEY: n
<222> LOCATION: (165)..(165)
<223> OTHER INFORMATION: a or g or c or t
<221> NAME/KEY: n
<222> LOCATION: (177)..(177)
<223> OTHER INFORMATION: a or g or c or t
<221> NAME/KEY: n
<222> LOCATION: (209)..(209)
<223> OTHER INFORMATION: a or g or c or t
<221> NAME/KEY: n
<222> LOCATION: (223)..(223)
<223> OTHER INFORMATION: a or g or c or t
<221> NAME/KEY: n
<222> LOCATION: (226)..(226)
<223> OTHER INFORMATION: a or g or c or t
<221> NAME/KEY: n
<222> LOCATION: (249)..(249)
<223> OTHER INFORMATION: a or g or c or t
<221> NAME/KEY: n
<222> LOCATION: (320)..(320)
<223> OTHER INFORMATION: a or g or c or t
<221> NAME/KEY: n
<222> LOCATION: (395)..(395)
<223> OTHER INFORMATION: a or g or c or t
<221> NAME/KEY: n
<222> LOCATION: (396)..(396)
<223> OTHER INFORMATION: a or g or c or t
<221> NAME/KEY: n
<222> LOCATION: (404)..(404)
<223> OTHER INFORMATION: a or g or c or t

<400> SEQUENCE: 72
gcggccgcgt nccctctcgc ccgnaaagag gactggagaa ggggctgggg tggaggtnnt    60
ctctgtgtgt gtctanggtt gngggcagga gaggttaatt ctattaagan ntcatcaatc   120
anccngtgtg cacttttcgc tcgacancgg ntcctnctac ttnanagcaa gtctggncca   180
gctgggatcc gaccagaaac cgcaagcgna ggagacgcat gancgnaggc tgagcgctaa   240
ctgaaggcnc gacctgagcc ctgcagcctg ctggggagct gcgcaaccac ggacagcagt   300
tcggcaatac acggcctggn ctgcatggcc cccgtcacca cctcacgtgg gaagccagca   360
ctgctgccgc cagccctgcc gctgccctca gactnncaag gcgnccaggg tcctcccaac   420
gcgcctgccc cacac                                                   435

<210> SEQ ID NO 73
<211> LENGTH: 2343
<212> TYPE: DNA
<213> ORGANISM: Homo sapiens 4.E53

<400> SEQUENCE: 73
tggccaggtg aggtcaggct ctgtttcttc cgagctacca tcctctacct gattcctcac    60
```

-continued

```
accttttttct tgttaggcgc agctaagaga cagagagaga gagagagaga gagagagaga       120
gagagaagcg actgaaacag agagtaaatt ctagtttctc cttttagtc tcttttcttc        180
tgcccttgc tctgctagtt tatctgcgtc ttttctcttc tcgcgctgca agagtggaaa        240
actcgtgctc agttctaggc aaacattaac cccgggcgac gtttccaagc gggagacaaa      300
ctctagagag tgagaagcga gatgcgaggg caccaagggc aagaaggggg ctcgggtac        360
gccacgttgg cgggacgccg ccgccgcctc cctctgctgc gcggcctgcg ccgggagcct      420
ggtgggggcg gcaagacgac agaccccgcg cccgggcctc ccaccagtga ccacctccct      480
cgcagcttgg gctgatcctc cagacagcat gcaacggtgg ggagggaagt cccctgactg      540
ggcgggggac ctagcggctg ctctgaaact ccgaacacct gaagaggagg cgcggaaggt      600
ccagccgccc aagactcgca ctttcccctc ctccgcagcc cgggcaggtt accgtcctgg      660
gcctgggtga gcgcggaggg gatccgggcg ggagctgagc tcggttcccc aggcctgaca      720
agtggccgcg tggcacgacc aaccccgggc acagggctgg ggctgctccc caaggtgggg      780
aattttaattc tcacattttc gcactaccct gacggagctg gacgcgggaa gcggaaaga      840
cccgttcctg tttgcagtgc ccgaggggca ggacacctac cagaagggct ctatcacagt      900
ggtgttaggc cgggcgcagt ggctcacacc tgtaatccca gcactttagg aggccgaggc      960
gggaggatcg cttgaaccca ggaggcagag gttgcagtga gccaagatcg ccccactgca     1020
ctccatcccg ggcgcagag ctgtcttgaa aaaacacaca aaaaacaaaa aacagtggtg      1080
ttagagggat gggattatag gtgacatgac tttcgtttg aactttcctt aaccttgcag       1140
gggcagccgt gccctgaaaa cgcctgtgat ttggagtaga gggtccaggc gcagtgtggt     1200
gagtgaccct aggcaggtca ctagttcttt ttcagccttc actgaatcct ctcttacacg     1260
gggatgttac ccccaggtct ccgtgtcttt cagggagaaa ttagttcatg agttagatgg      1320
tgcactatca atcatccttt tattagacag aaacaataag tttgaggaag aggacgtcta      1380
ccttacaggg ggtttaattt tcagcttctt tgagataaaa ttcattgaac ggtgttttac      1440
gtgcgcgcct tttccaacag accccacgcc tattcccagc gccagaggcg acaaccgct       1500
ttactgagat acagagacag gtacttcctg aggcacttca gtccagttcc actgggttta     1560
ctacaactaa taatgactgt ttctgtttac taggtattag gcgatgtgtt ttaagtaaat     1620
gaattgtctc taatcctcac aactctaaag caagttaggc gtcacccgca ttttacaaat     1680
catagcgccc tgctcaccat atctggaatc ttgcctcgcc ccgagggttc taatttttcac     1740
tttagagagc tgagcaagat gattgcccag cgctaactcc gtgaaatccc tgggactgaa     1800
aatcacaggt aactcgccag agttttcaa ttttaggcct aggagattat gcaaagattt       1860
ccttcaagta aacgctgttc tctggggcct ctgggatcta cagtcggaga agggaataa      1920
gtcccgggcc ggtgggggat gggtgggtgc agtttcctaa atagaggaaa gccacttca      1980
ttcaaagggc tgtggaactc tggctagagg tgggtttctt tgcagttaat catctgcaag     2040
gctctttgga tgcctgattc cagaaaccca gaactcacac ttagggtcac aaaatccagg     2100
gcatttattt gccgagcccc atggatgtta tccctatgga tgcaccccgc cctgtccgt      2160
tctcctttgg agcagaacga aacccattcc agagcttttg caggaagtct tcaggccctt     2220
gcgtccggcc cctttagaca tcaaagcccc ccctgagagc aaaggacttt gaaagatagg     2280
aaaagctcag gatccttatc gcgtctctgc tccctcccga cctagtcgta aattccgagc     2340
ctc                                                                    2343
```

<210> SEQ ID NO 74
<211> LENGTH: 507
<212> TYPE: DNA
<213> ORGANISM: Homo sapiens 4.F.15

<400> SEQUENCE: 74

| | | | | | |
|---|---|---|---|---|---|
| tacgactcac | tatagggcga | attggagctc | cacgcggtgg | cggccgcggg | cagtgcggac | 60 |
| caggcggggg | ccctgtggct | gccggccaca | tcccggagca | acagcagaaa | caacggcagc | 120 |
| agcagcagca | gcagctgggg | cccgggtccc | gggctggtcc | gagcggggac | atgagccatg | 180 |
| gcgtggtgag | ggcggcaaag | ggtcgaagtc | caggaggagg | aaggcgagcg | ctggcgcacc | 240 |
| ggaggctgcg | gactgacctc | gcggcagtag | ggcgcgcggg | gagagcccgg | gcagcagggc | 300 |
| gctggatacc | gaggtccgcg | cggggcgagg | ggcttagcgg | agcaggcacc | cgggcgcgcg | 360 |
| gtccgtgggt | accggtggcc | cgagcccccg | gccagcggtc | acagccgtcc | ggagcagcgc | 420 |
| agagccgagc | cgagcccgag | tcggcgcgct | gccttggcgg | actcgcgctg | cgaaagtttg | 480 |
| tagcccactg | cgcgcccggc | ccggctg | | | | 507 |

<210> SEQ ID NO 75
<211> LENGTH: 446
<212> TYPE: DNA
<213> ORGANISM: Homo sapiens 4.F.17

<400> SEQUENCE: 75

| | | | | | |
|---|---|---|---|---|---|
| gcggccgcac | acacgagggc | ccgtcgcgcc | cccgcccctg | cccgcctcg | ccctccacgt | 60 |
| ccctgcaccc | ccgagtcgca | ctaagaaccc | agtccccgat | cggtttcctc | tacgccgtct | 120 |
| gagcagaaga | gagtgggaac | cggggtgacg | gataaggggg | gggcgcccac | gcgacgtcgg | 180 |
| ggtgcatggg | agcgcgcggg | aggcgctagt | gggtgcacgg | ggcgtgaggg | ggacacagcg | 240 |
| cgggcgtggg | gatggccact | gcgcggggag | ggttctgcct | ggagaaggag | ggatgggagg | 300 |
| aggttggggg | agcagggcgc | gtggaggagg | gaggttggac | gtgtgtacag | cgcctgggga | 360 |
| cctcgctggc | cccttggtgc | ccccaggact | ctgaggcttc | tcctttcggc | ttgaaatgtt | 420 |
| tttcccttcc | tgcttttcaa | atctgt | | | | 446 |

<210> SEQ ID NO 76
<211> LENGTH: 424
<212> TYPE: DNA
<213> ORGANISM: Homo sapiens 4.F.22

<400> SEQUENCE: 76

| | | | | | |
|---|---|---|---|---|---|
| gcggccgcct | tgaaggcgct | ggacgggatg | gtgctgaagt | cggtgaagga | gccccggcag | 60 |
| gtgagctcgc | ggcccgccag | cccgctgccc | acgcagtagt | ggaagaggcc | gaagtagcca | 120 |
| ggcttggggg | tgctcacgct | gtcgcccacc | cagtagggct | ggatgaagac | caccacgttg | 180 |
| atgatggcga | agcagatggt | gaagatggcc | cacagcacgc | cgatgcccg | cgagttccgc | 240 |
| atgtagtgct | cgtggtagag | cttggaggcc | tcctgcgagg | gcagcatggt | gcccggaggc | 300 |
| ggggccggcg | gcggcggcgg | ctggcggggg | ccgccggccc | gggacggagc | gccggctgc | 360 |
| cgggcgggag | ctgggacgc | acgcgagaag | cggccctgag | tcaaggaacc | cgcgagggcg | 420 |
| gggc | | | | | | 424 |

<210> SEQ ID NO 77
<211> LENGTH: 558
<212> TYPE: DNA
<213> ORGANISM: Homo sapiens 4.F.6

```
<220> FEATURE:
<221> NAME/KEY: n
<222> LOCATION: (413)..(413)
<223> OTHER INFORMATION: a or g or c or t

<400> SEQUENCE: 77
gcggccgcag ctcaccactg gcctagagat gcccttttgcg aggcggcagc aactgacaag      60
atggtcgcgg gtcgccgcgt ccggagccgc ccaccaggtt gccaggagga ggcgggagcg     120
gggatcaagc ttatcgatac cgtcgacctc gaggggggc ccggtaccag cttttgttcc      180
ctttagtgag ggttaatttc gagcttggcg taatcatggt catagctgtt tcctgtgtga     240
aattgttatc cgctcacaat tccacacaac atacgagccg gaagcataaa gtgtaaagcc     300
tggggtgcct aatgagtgag ctaactcaca ttaattgcgt tgcgctcact gcccgctttc     360
cagtcgggaa acctgtcgtg ccagctgcat taatgaatcg gccaacgcgc ggngagaggc     420
ggtttgcgta ttgggcgctc ttccgcttcc tcgctcactg actcgctgcg ctcggtcgtt     480
cggctgcggc gagcggtatc agctcactca aaggcggtaa tacggttatc cacagaatca     540
ggggataacg caggaaag                                                   558

<210> SEQ ID NO 78
<211> LENGTH: 865
<212> TYPE: DNA
<213> ORGANISM: Homo sapiens 4.F.69

<400> SEQUENCE: 78
gcggccgcag cgagttttct ggcagcgcta gcgccgcggg gcctgggttc ccggggttccg     60
gtctccgccg gctccgggct cgcccccgcg agttggccgc accgttcccc cgcccgcggg    120
gcagccgctc ctccgggagg ctccggcagg gaccttcgcc ccggccccg agcggcagtg     180
cggctccagc tggaggcctg gcccgggaag caaagtgaaa ggacagaggc ctccttcctc    240
gccagccgcc cgccgcgcct ttcccagctc aggccggcgg cccgcggcgc ggagggagcg    300
aaagagtcgg ggcctgcccc ctccaccgcc cgcatctcgg ccgccgcacc cgggtccgcc    360
ccgggaggcc ccgcgggagg gaaccccgg cccgctgggc gcttccgcac tgacgccttg    420
gggccgcgcg cccccgcccc ttactaccgc tacacccgct gggccccga ccccgctccc    480
gggctgctgc cagcgccgtc ttcccccgta gaaacttcgg agacacccgg gaagctgctc    540
tttggagttg gggaaactta ggaagaatgg gaaaagccga ggaagtcggg gaggaccccg    600
cagttgcctt gccctcggcc gaaattcctg tgcaattgga cgggaagcct gccacgccca    660
gagagccacc cggtggcacc ccgttgggga cctgcggctg ccctaggctt gagctggcga    720
ccaacggcgc ataccccggg caccctagg ggaccgtgcc cggcccggct tgggggctcc    780
taacgccagg cttgtgagct ataggtgga gagtgggccg gctcttaagg ggaaaaattt    840
gcggcctttt accaggcaca gccag                                          865

<210> SEQ ID NO 79
<211> LENGTH: 983
<212> TYPE: DNA
<213> ORGANISM: Homo sapiens 5.D.9

<400> SEQUENCE: 79
gcggccgcag ccagcgccgc ccctcccggc cgggcgggcc ccaaaagccc tttctgtcac      60
cgcaccaggg cgcgaccggg tgatgcattt ccacaccagc ccgcccaaac ctccatggtt    120
ttggagctcc cgggcaggcg gtggaaactt ggcgcaccgt gcccactctc cggcgccgct    180
```

-continued

```
ccgacagccc gacgggtccc gcggccagga agccactcgg cgcccctcgc cgtcactcga    240
ccccccggcc ctttcggact ccgatcctcc cgtccccagg ccacacggcg cggaaagggg    300
atgccgagcg ggacgcgcac gaccagggcg cccaggacga gggcgctgga ggagactccg    360
ggcagggacc ggggtcccag ggcccggggc cggggctcaa cacccacccg atgggtgcg     420 ggcccgacgg ggcccggggg tgggagtagg ggcggcgggg gcccgcggag gaggagtggg    480
gataggccgc gcagggggtg cccgggaccc cgggcgcaag ctgggaaaga ggcacgcggg    540
ggcggcgcgc cggggccggg acaggcgccc gtcctcacct gccgggcagg tgtcccgccg    600
gcgagtcgcg cgcgttgctt tccgaggtgg aactgtcgtg gtccacggcg catgcgcgc    660 tgaaggcagc ggccagcagc ttcataaggt cggcggcggg gcaggtgccg gggccgggtc    720
ggaggccacg ccggggccct gggctggggt cggggcgact agcgggctgc gagcgggttc    780
cacgcgcgcg gttcaacggg ctgcacccgc ccgcaccgt gccaacactt cgggcgggcc     840 ccgctgagge tccggttgcc cgcactagga ggcgagggcc cccgcgtgca agccgccggc    900
ggcgggcccc ggttgccacc ggccccagcc atgggtgggc tccgggttgc tttcccccccc   960 tgccccctag ggaattgagc cga                                            983
```

<210> SEQ ID NO 80
<211> LENGTH: 432
<212> TYPE: DNA
<213> ORGANISM: Homo sapiens 5.E.2

<400> SEQUENCE: 80

```
gcggccgctg gtgacctccg cccgcggtca ctcgacgccc agccttggcg cgtttgcgca     60
actgcttttg tcccgagcct tcattctggg cgcagtcccc tctcccagtc ccctgccgc    120 ggcgcctgga actctcctgg tggctgtaag attttcctac cgttaggtcg tctgtggcga    180
ccgccaggcc tgccccacat cgctagccgc cctgtctacc cctcagcctc ccagccacta    240
aactcgctgg acaaccttac gctagtaaca gttttttgagt ctcagactca tctgtgaaag    300
ggcagtcata tttgaggact ccaaatgggc tgcagtgcgt aaaccaccat gcgatatttg    360
gttgctattg cccacctcag cctgtggcca atgtgtctct gtaggaacag cactagattc    420
tttggggttt tt                                                         432
```

<210> SEQ ID NO 81
<211> LENGTH: 746
<212> TYPE: DNA
<213> ORGANISM: Homo sapiens 5.E.25
<220> FEATURE:
<221> NAME/KEY: n
<222> LOCATION: (695)..(695)
<223> OTHER INFORMATION: a or g or c or t

<400> SEQUENCE: 81

```
gcggccgcgg gggcgtcagg tccttgcgcc tcctcctccg gctcttcccc cagcctctgc     60
ggggcgtcct ctcccacctc cggggcccac tcctcccccg agagccccg gggcgcatcc    120 tcaaaagcat cctcctcacc ctcctcatcc gtgtccccag ccctcgcac gggggctccg     180 gccgcttcct ccccccggcc ggcctcggga atgggaaag ccgtggagga gggcgagtct    240
ttggccgcgg gttgcgctgc cgggagactg ggcgcctcgg agaccgggag gccgccgggg    300
gacggcggtt gctggggctc ccggggctcg gcggccaggc tctcgggcag gtcggagagc    360
gcggacagcg cctgctcggt gtccggactg ccgggggcct cccagccccc gccgctcggc    420
cccagcagga accggtccag gcccaggaag gccccgggct gaggggagac ggcagtgggg    480
```

```
ggcgctgcag gctcctcggc gccctggagc tgctgctgct gctgctgttg ctggagctgg      540
agctggagct gctgctgctg ctgctgctgc aggcggatcg cctgctggat gtctgaaagc      600
aaatcctctt gctccgtagc cgaatggaag ctatagatgt ccgtgtccga gcccgagctg      660
gtcctttgtc catcctgcgc ccctgctgca gtttncacat cctcggcgat cggccggccc      720
ccgaccctag cctcggcagg cccagg                                           746
```

<210> SEQ ID NO 82
<211> LENGTH: 617
<212> TYPE: DNA
<213> ORGANISM: Homo sapiens 5.e.4

<400> SEQUENCE: 82

```
gcggccgcgg gccggtgttt caggcagctc ttgggcgccg gcgggctcgg ggcgggcgcc       60
gtggagggct cggtcccaat tctctcgggc tcggtccccg ctcctctctc gggctccgtc      120
tccgcttctc tctcgggctc aggcgccggc cctgggggcc ccttctcctc atccgggagc      180
acgggcggcg tcggctccgc ttccttcggg acactgcgtt ctggcccgtc gcgagcagag      240
ggcgcctctg aggtggcggc ggggtcagtc tcggggggag tcgtgtcccc ctcagggatg      300
gcggtgggaa acgggctcgc gacgtcttcg ggagcacaga ccacctcctc cgccttgtcc      360
gtggccgggg cacacgggcc tgcggggggc gcctccccat cctgctttcc gccgtcggga      420
ccgggattcg gggggccctc cggcggggac ggggggctcca cgcggagagt gggggccgac      480
tcgggctcgg cgagctccgg ggtggccggg cggcttgagg ggtcctcccc ggggacgccc      540
ccctcctcca cgctggccgt gagcgcggag gagtgctgca ggcgggcgcg tctggcacgg      600 gccccctccgg gtggcgg                                                    617
```

<210> SEQ ID NO 83
<211> LENGTH: 1840
<212> TYPE: DNA
<213> ORGANISM: Homo sapiens A.2.F.45

<400> SEQUENCE: 83

```
ggcgcgccga ggcgcaggcg cggagaggcg cggcgctctt ggggagacgc ggcgcagggc       60
atagacgtac gccggcgcct ccccggaggg gaggggtcgc tgggcgggcg ggagtgaggc      120
gcggcgccgg cgcagagacg cacgtcgctg ggctgagggt ggcggggagt gttgcagtcg      180
tacattcgcg cgccgccggg cggggagcgc ggggggtggcg cggtgcaggc gcagagacac      240
acgtacccgg cggcgcagag acgagtggaa cctgagtaat ctgaaaagcc cgtttcgggc      300
gcccgctgct tgcagccggg cactacagga ccagcttgcc cacggtgctc tgccattgcg      360 cccccctactg gcgactagga caactacagg gccctcttgc ttacagtgct gtccagcgcc      420
ccctgctggc gccggggcac ggcagggctc tcttgctcgc agtatagtgg tggcatgccg      480
cctgctggca gctaggaaca ttgcagggcc ctcttcctca cattgtagtg gcagcacacc      540
cgcctgctgg cagctgggca cactgccggg ccctcttgct cgcattgtcg tggctgcacg      600
ccacatgcag gcacatgggg actacgcagg gccctcttgc tcccggtgtg acggctggcg      660
tcccatattg gccacctcct gcaccactta agtcgagagc gccagttatt aatccccatc      720
agttctgtaa attaaaactg aaaaggagct attactgcgg agagctgatg tcccagttat      780
taacttggaa gacagctttt caccaagagg cagtacaaag atggaagata acttcattga      840
aaagaaatac agtgtaaaga gcttattgta caaaaatagg gaggagtagg ctgatactgc      900
```

-continued

| | |
|---|---|
| atgaaaacag cctaagagtc ctgtgcaggg attttattt tggacttctt cacattccta | 960 |
| cctctgtctc aagtctccgc ctgttttctt tggttttcct gctactgcct taggtccccg | 1020 |
| acttgcccca cttagccttg tgggacctcc tcacttgatt gaggtacatg tgtggtgatc | 1080 |
| aatccgaatc cactctggca ccagcctcct tcccaccata ccaggcaggc tgacagcggt | 1140 |
| cacgtttgta tctactgcag ctgcctcttt tgaatgtctt tctctgcctt aatctgtact | 1200 |
| tatggtgcca ggtttctctt aagaatgtcc cctttgtcct tcttatcagc atgtagctag | 1260 |
| caatattctg acatttttat tgcagaatga atgatgattg gggcttcttt tttttttttt | 1320 |
| tttttgagac ggagtctcac tctgtcaccc aggccagact gcggactgca gtggcgcaat | 1380 |
| ctcggctcac tgcaagctcc gcttcccggg ttcacgccat tctcctgcct cagcctcccg | 1440 |
| agtagctggg actacaggcg cccgccaccg cgccagctaa ttttttgtat tttagtaga | 1500 |
| gacggggttt caccttgtta gccaggatgg tctcgatctc ctgacctcat gatccacccg | 1560 |
| cctcggcctc ccacagtgct gggattacag gcgtgagcca ccgcgcccat ccgattgggg | 1620 |
| catcttaaga gaagttctag ggtgtttctg cgtaggtacc tcttctccct cctaaccaca | 1680 |
| attgacaagt gcccatccac tccagcacta gagatgctac taatatgtgc attttggtg | 1740 |
| gtccctccag gtgagccttc acagactttc ccttttccag gagctccccc tcctgttcat | 1800 |
| gtctagctag ctatctactc taacagagcc cactatcctg | 1840 |

<210> SEQ ID NO 84
<211> LENGTH: 3592
<212> TYPE: DNA
<213> ORGANISM: Homo sapiens A.2F.50

<400> SEQUENCE: 84

| | |
|---|---|
| gccgaggagg cggctccgac ccaggtcgtc gcagcagcac aggaagctgt aacacaggta | 60 |
| agtgcaggag agcgagagcg tgaaggcgaa gagcagcctg cgcgccctcc gcggctgagg | 120 |
| tggccccgcg cggcccagga ccctataggc catggctcca tgggcccgcg ccggggtca | 180 |
| tggtttccga gggggcaccg gcggctgagc tgctgtggcc ctgcggtcgc ctagagggct | 240 |
| cgcgtggcgc tgccacggcc acgcgggtcg ggcgttgggg gcgccgtctt ctccggggc | 300 |
| tgctgaccag ggtgcgcaca gtgccagggg gtcccggggg cagcggctcc tcggggaaca | 360 |
| ggcggttgca tttccagcat ctcccggtcc taggcgatgg ggctccgggc agccgggcgg | 420 |
| ctcgggcgct cccaggctct tacgtgcgcg gggttcggag gcgcgcccagc gcccgaagcc | 480 |
| ccattcctga tcctcggagc gccgctcacg aaacgctcgg cggcggcgcg gctgtgcggg | 540 |
| ctggcgggtg gaccggacgg tggcgctggc gccggccgcg atctggctct tcgggaaatg | 600 |
| ccgagcggag cgcgctgccg gctctattta aggagtggcc tgacgtcagc cgcgcgggtc | 660 |
| ccccgagccc gcgccgcgcc cagggacctg gcccgccccc tgcgccccca ctctcttacc | 720 |
| cctcccagaa acacagcacg cgggccctcc ccatgcaggc cactccctac ggagccccag | 780 |
| gccagctttg gggcggtgaa acgaaggtgt caaggcatag tactcctccg ggaggctgga | 840 |
| caccccacc acgctggcct ctcgacatcc agggacacga atccaggtcg agatcgcgcc | 900 |
| gacatgcaga ccagacagac ccagacgcag acgcaggcac cctgccctga tgcgcggtcc | 960 |
| caccaccctg acccgcacac gcacgcacag gcacagaagc acgcgcccc tagcccggac | 1020 |
| acaccccac acccacgcgg gggtggggag gagaagtccc ctaacctggg cccagataca | 1080 |
| ccgacaagga cactcccccc gctctcgaca tctcgccaaa tggacacaca cagcccggaa | 1140 |
| tcggacaccg agcgcacgca cgccctggac tgggacacgc gctgtagacg ggatgggtgg | 1200 |

-continued

```
aggagccgag cgtgagtgag attccgtgac tattcaccca gcttcttagc ccccagcgcg    1260
ctgactcaca ccccggcggc tcgctctgtc tcgcacctat gaggcacgcg cgcaccccaa    1320
cccattgtca ccccacctct ccccgggcct gccggagagc gagccccgga gcggcagact    1380
ccgcgtcagg agggttcctc tcttagcagc cgccgcctag cggtagactg ctccccgggg    1440
agctgtccag ggtaccagag ggtcgccgag ggctgagtga ggagggcttc ttcacacaga    1500
gacactagga ggaggaaaca gagtacaagg agaacgtatc caggagcaat tccacttcga    1560
atgattccta agtgaatgcc tacaggacag ttctcggtga ccatgtccag aacaggcata    1620
agtgacgatc cccagtactt ccctgaggga ccacactggt accttggatc agaaccctgc    1680
atcagaacag gcctaaatgg ccatggctaa gaacacggct gagttgtcct tcaacagcaa    1740
tgccaatgcc aattcaccat gtccgagtgt tcacaaggtg agtgccctcc accaccaccc    1800
agccatagaa tgtctagatg accaccatga cccccaccct gatcagggta taactgactt    1860
ccttcctcag gctgtaaact gatcattagg ttctgtggat cttagcccaa accagaaaat    1920
attttgtccc caaactagtc ccatccctag aaaccttaaa ccaattctac ggcagataat    1980
aataatagct gccaactttg tatcaagcac ctggcatggg ttaactgatt aaatattcac    2040
aacctatgaa gttgttacca ttaccctggc atcactttgc tgtcttaatt ctaatagtag    2100
ctagcattta ttgagtgctt gttttatggg agttatgcgc taatcacttg acatgcacta    2160
cctcatttat ctttggagat aggtattatt gtaatttcta atctacaggc agtgataaga    2220
agatttaaca aacatataca cagtaactgg cagagctggg attaaacccg ggcagtcttg    2280
actccaagat tcaagctctt agttacagca ctttgcagct tcctaacttc ctttgaccat    2340
tattcatata attccatcct aggctcctct cctggatgta agctaatttg tctatgtctc    2400
ttctaaaatc tcacacctgg gactgcgcga ggaatttcag atatggattg aaaagttcaa    2460
caggactctc acctctcttt tgtaagttct atttctagta atgccaccta agactccatt    2520
atctttttct tgtggctata tcacactgct gacatctcaa acttgcagcc aagtaacatc    2580
tctaaatgtt tcttacaagt gctgctgatt aaggcacagc taccccatac tgtgcttgta    2640
cagtgggcct ttttggaccc aatgtgtagg tccttataga tttgacttga ttgcatttca    2700
tcttgtctca tcagttcgct gccctagttt ttttttaaatg tctatttgaa gtcaaaccac    2760
gaggtagctt tcatttattc aaaaagaaaa agtagaaaga ttgtatccca gctttaccct    2820
ttattccagg tgtactttgg gcaagtggac ccccttaaag cctcaggttc ctcagctgta    2880
aaatgggacg ctatgattca ccttaaaagt ctctcaaagt ttagatgttg catgattcta    2940
tgattccatt acccaaagca tgaaccactc acttggcatc atgtaatttc cacagttgat    3000
cacaatttaa ttaattcctc attctaattg ttaataaaaa tgtcaaaaca aatatactta    3060
aaggagttct tcttcttctt ttgggtgagg ggaagtgtct cactctgttg accatgctgg    3120
catgcagtag tgcaatcata gctcatgctg cagcctccac ttcctgggct caagggatcc    3180
tcctgcctca gcctcctgag tagctaggac tacaggcatg tgccaccaca cctagctagt    3240
tttttaattt tttgtagaga tgaagtctta ctgtgttgcc caagctggtc ttgaactcct    3300
gagctcaagt gatcctcctg cctcagcttc ccaaagtgct agaattacag acatgagcca    3360
caatgcctgg cctggaagga gctcttatat atactttgaa caattattca catcatgaac    3420
ctgctatttt tgtattccat tgttaaaatt acaaggttaa atgtggagtc atctgctgtg    3480
atcagtacta tttcccttag aaaataaaac atgaatataa tgatttctca taattctgtg    3540
```

<210> SEQ ID NO 85
<211> LENGTH: 2722
<212> TYPE: DNA
<213> ORGANISM: Homo sapiens A.2.F.67

<400> SEQUENCE: 85

| | | | | | |
|---|---|---|---|---|---|
| cttggcttaa | ttttttaaata | attttttaacc | tttgaattca | taaactgtga | ta | 3592 |

| | | | | | |
|---|---|---|---|---|---|
| cgccgccgag | gacactcggg | cgcacacccg | ccgcgctggc | gtcccccacc | cccagcccaa | 60 |
| acaaaagaca | agccttgggg | tcgtggcctc | gctgggccgg | ggcgccccga | gccggccagg | 120 |
| gcgccctctg | ggccagagc | tccatggttt | gcctaaggca | tagcttcttg | gcggtaggcc | 180 |
| gcaagcggcg | gggagacgcc | aggcagggct | gggccgccca | gaggtccgaa | gatgcctcca | 240 |
| gtcgccgccc | cggggaaggc | gcgggcgacc | tctgagtgtc | ccggtaacgt | gtgcctttgt | 300 |
| tccccaactc | aggtgaaaat | ctggtttcag | aacaaaagat | ccaagatcaa | gaagatcatg | 360 |
| aaaaacgggg | agatgccccc | ggagcacagt | cccagctcca | gcgacccaat | ggcgtgtaac | 420 |
| tcgccgcagt | ctccagcggt | gtgggagccc | cagggctcgt | cccgctcgct | cagccaccac | 480 |
| cctcatgccc | accctccgac | ctccaaccag | tccccagcgt | ccagctacct | ggagaactct | 540 |
| gcatcctggt | acacaagtgc | agccagctca | atcaattccc | acctgccgcc | gccgggctcc | 600 |
| ttacagcacc | cgctggcgct | ggcctccggg | acactctatt | agatgggctg | ctctctctta | 660 |
| ctctcttttt | tgggactact | gtgttttgct | gttctagaaa | atcataaaga | aaggaattca | 720 |
| tatggggaag | ttcggaaaac | tgaaaaagat | tcatgtgtaa | agcttttttt | tgcatgtaag | 780 |
| ttattgcatt | tcaaaagacc | cccccttttt | ttacagagga | ctttttttgc | gcaactgtgg | 840 |
| acactttcaa | tggtgccttg | aaatctatga | cctcaacttt | tcaaaagact | tttttcaatg | 900 |
| ttattttagc | catgtaaata | agtgtagata | gaggaattaa | actgtatatt | ctggataaat | 960 |
| aaaattattt | cgaccatgaa | aagcggaatg | tttctgaaaa | atacttcatt | ctgcccctct | 1020 |
| gataactggc | tagtgaagtt | ttattgaagg | caactaaaga | aggacaagct | ctgcagagat | 1080 |
| ccaacaaggc | aaaaagaaa | acagaagtcg | gggctctatg | catgcagact | gtatatgtat | 1140 |
| atatgttcaa | tgctatactt | tgtgtgtgtg | tgtgcatata | tatatataat | atatatggca | 1200 |
| tgttatagt | actgccatat | ctcataattg | tttcaggtag | aaagtaatgc | tgaaataaaa | 1260 |
| atacatccct | ctcaccctgt | atgtgagtta | gaaggcaaca | gaaatccctc | aataacccct | 1320 |
| ctgaattcta | agctcaaagc | aatttatctt | gagaagcgcc | cccacccatc | agcctctgtg | 1380 |
| tagtgccaga | gcaattagac | aaaattaccct | tcaaaggag | tttccagaga | tgagaaaatg | 1440 |
| aaaagaaat | ctagcctcac | acctattaca | tttttaaaa | atctaaaatg | tttggagcat | 1500 |
| ggcaaatgat | agaaccttgg | actctttgga | gtatgattat | aaatgtatcg | gctcttttcg | 1560 |
| agagatgaaa | acattgcaga | tattgtgaag | agggaacttc | agggttgggg | aaaggaagga | 1620 |
| atgaaagcat | tgtggcgccg | tgttgatttc | attttgtgtg | agataatact | cttaatattt | 1680 |
| cccttcccgc | cttcctttttt | tcaggaagga | gcttcctctg | ttttgctttt | acataaaaca | 1740 |
| gtggcaaaca | ggttctaaat | gatgcaaaat | agaatctgtt | tactaggatt | tctcctttgg | 1800 |
| gaagccttct | ttgggacaga | gaggaaggac | ttgctgcagc | tgtgcccttgt | gtcccttcct | 1860 |
| tcttcttgca | ctcctgcatg | tagataccaa | cagcatgacc | agagctatgc | actgcaccta | 1920 |
| aagacccagg | cctgaattgt | aggtgtcttt | ctgtctggcc | gtccttcagt | gggccagact | 1980 |
| ctcttttcctt | aggatacgaa | ggaaaatgtt | gggttggaaa | ttacaagatg | catgtgaaat | 2040 |
| attttacagc | taggaagtca | gcagcaataa | atgtgacaaa | agagccttct | taaagtgggg | 2100 |

-continued

```
gtagattaga gcataaaaaa ttatatcctg tcactgagga tttctcagaa ggctcttcca    2160
gggttgggag actagacctg aaaaggcacg ctatgtgcct tgagggaat ttaccttacc    2220 tacatgtttc tctctctgtc tcgtctctct ctcctctctc tctctctttc tctctcattt    2280
tctctgtctc tctgcctgcc tcctcctcct cttctctccc tacctcccctt ccacctcctt    2340 tattttttc gttctcttct cctttacttt ttttctagaa gagttaccag gcccgccagt    2400
gtggaacagc ttgcttcttg gaggaatcag tattttgacc gctctttaga catatcccgc    2460
agcctggctc cgaggcagaa ctacgcccgg cagcctggcc tgtgcacccc tcctccggca    2520
cccccagcgg ccgcgactca atatttccgt ctccccagtc cgctccagcc gtactttctc    2580
ggaaggagca ctgggtgcgg ggaagagggg gcaataggaa ggtttgcggg gggcgggggg    2640 ggggcggga agccaaaggg tgccccattt tgttttctgc gctcacagag aataggggga    2700
ttggggaaga gatgaagata tc                                              2722
```

<210> SEQ ID NO 86
<211> LENGTH: 3366
<212> TYPE: DNA
<213> ORGANISM: Homo sapiens A.3.F.38

<400> SEQUENCE: 86

```
ggcgcgcctc cagttccaag gccgagctca ctttcaacag ctctggaaat atgaatgtat      60
ttttcccccc tttagaagaa gctatacgag gaacaacttt ttgaaatcgg gagtgtgttt     120
gtagagaagg agataaggat tgcatttcgc ttattttct acaggtgata gaagtgtttt     180
gggggtcaga gtatcctctc aaggaaaatg taaaacgtgg gggctcgcat tctctatcta     240
agcctttgta agtttaatta acaggaccct taaagtattc cttatagcta cagataaaaa     300
attacaggca atgtttggat aaggggccaa ctctccgtgt ccaaacattt agagaactgc     360
ctgtgagtgt acaccgttgt aatcttattg ggagcccttt gtcgaattct gtatttact     420 ttgatgcttt ttgagtacca ttcccattgt ttgggtgtcc tttaactccg tttacagcaa     480
tatattaata aagaggatgc atatgtcagc gttatgtatc cacaagaatt tggattcctt     540
taaaatcaaa cggcttggtg agcaggcaag cactcaaaac ccaacagtct caaacagcaa     600
taataatgtc agcaaacggc tgccatgcct ccttttctcc aaatgctgtt tattctaaaa     660
tcaataagtt aggagataca ttgcagagaa acagtcatta gtggttcagg gttggcaggt     720 ttgttttca ggtgtagatg ttcttgagta atacctctcc actgtggact aaatattagt     780
agattgtcgt tgtcattttt ctaatttaat gcggcagcct cagggaagta ctcatccaga     840
caattatggg gtatcgattt ttaacttaa gattaaaaaa ataccatatt tcacttgcct     900
tgggactact tttcttgata aaatatatc tgggaagatg attttagggc catgttagcg     960 tagggagg gaattaaggc acaaatggtg gttggttaag gaaatttat gaagaaaat    1020 aaagaaaaca tgtcagaata aatcaatcag aggcacaagt gagttagagg aatctgagga    1080
caaccagcat cttgggggatt cttctgttcc cgcggttctc agatataggga ataagggtct    1140 gagttatgcc cagaatacat tcgtctggta ctggatgtcc cagtccctta gctgttccac    1200
gtaatgaaga agctctaatt cccgagaact tggggcttta ttttaccat cattgagtct    1260 gcccaggctc agctctctta caaaggtata aatctgaaat tcatgtatta atttgaatcc    1320
ccaagatccg agttatgaga aagggcaagg gcaggctcta ctcctatttt gtttactttc    1380
accgagttac tgtgaagtga ttggaaactt tcttaacggg cagagagaga atacacggaa    1440
```

-continued

```
actcggatgc agtaataaag ttgacatagg agtcggaaca gggggctctt tttggatctc    1500
acctttactg gggcttgagg ttgtggaatg ggtggaagag taattaactg aatgaagaat    1560
tttaacgttg aaaacagagc ccacagtatt tttggttata gtggtgtggt ctctgcctcg    1620
gcaaagaaac aaacaccccc accccatctt cgcagttctc ctctctgctg tagcgacgcc    1680
aggcgctgct ttccgccggg taaattagcg gcgagcctcg ccagacgctt tcctccttgc    1740
cttctttcgc cgaaggggg cgcgctcctc ccaggctgcg ctggtaccta tcctgccttc    1800
aaaaatttct gggttcctgc aggacagaca gtaacaaaac gtgggaaata atagtttgat    1860
gacacttcag ggactatagg aatataaggt gcacacacat gcatcttaat ggaaacatgt    1920
agacacctgg caggagcatt ggctgcctgc ctctcctcct ttcaaatgag ggtggtcggg    1980
gttccagggt ggcaggaggg gagtggggcc agatgaccgt ggatgaatt ggtgggtgct     2040
aggactgacg cctgggttcc atggcggagg agagggtttg tccccatgga gctgtgtgga    2100
cttttctgca tatgtacttg aggtcttcaa agaaagaagg gcagatctga gaaatggaga    2160
agtggctggt attagtgaga tgttgaaaaa ctgccacaga agccctcaca gtgcctggag    2220
tgttaagaca gaagagaaaa cctggcacca tagagtttta ggccctggga tcagggtaac    2280
cttcctcct cacgaaagaa caataactgc cccaaatctt gtgtgagcct gcaacttggg     2340
tacctaaagc catttccaat ctgcaaatct gactcctggc ctccactgat cctccatttt    2400
tgggcaagag tttcaagaga ctcacaggac agatgaggat aaattttaa cccttctgt      2460
aaatttaggg attttcgact tcttaccact ccctgacaat gggggtcaac aaatcaaggc    2520
acggtgagag taacaaactg gaataatata tattttgtct tcatagcata gatgatggtt    2580
aatacatact ttccaagata atctgagctg gagtgttcac tagaaacagg agcacaaggc    2640
cagaactgta aggcaaattg cttcccaca aacgtttgtc tgagaataag aacattcacc      2700
ccattcactt aatttctcat catcagtcat gtcattatat tttcaaggac ctcacagtgc    2760
tggaaagtgg tgtagttata aataagcata aaaacagatg ggtgatccca gtcctctaaa    2820
tataatcggg gatgccaaat cttttcaaag agaattcata tatacaactt aaaggccaag    2880
gagcccaatt caatcaaaat ttgagccagg atatgctaag ttcaatcagc ttgaatatgg    2940
gcaaagtgta agacctagcc agcacttcag atatatacag agaaccacat tttctcaagt    3000
ttccattgtt attttccaca caaatttagt gttagtcttc aaagggattg ttagatttgg    3060
tttgggccgg gagggtggtg agagtcagtg ccccaggctc ctgtccttgt ctactcccct    3120
ttctttggta ctctctctgc ttcagcagtt tgccgaaaat ctgtgttgca gagaaaattg    3180
acacctagag gccacagagg tctcctaaat gctgttttct aggatcctca gaaaacaaga    3240
ggaccgctga gctcaattat atgtaatata cctggtatct ttatgtattt ttcttttctg    3300
ctaattcatt ttataatagc taagttagag acttcttgga gatttaggtt ttggggactg    3360
gatatc                                                               3366
```

<210> SEQ ID NO 87
<211> LENGTH: 638
<212> TYPE: DNA
<213> ORGANISM: Homo sapiens A.4.D.30

<400> SEQUENCE: 87

```
ggcgcgcctc gcccgagatg cccctgcgtc cgcctggcca ggcctggggg ttacccgacc      60
cgggttctcc cttcgctggc tttgcgcccc ttcacacctc tgcggtgggg acggagctgc     120
cgagacaagc agagtgcgaa ctggagaaag cccagagctc agagctccca ggagcccacc     180
```

```
gtgccccacg gctaggcggt ctcctggtgt ggacggctag cggtgtcatt acttcttaca    240
aaagtttatt tttgaaagct tctcccttcc ttccttcttc ccttcctttc ttttcttcct    300
tttttctttg ttttgagtca ggttctcact ctgtcgccca ggcaggagcg cagtggcgct    360
atctcagctc acggagcctc cacctattgg gctcaagcga tcctcccacc tcagcctccc    420
gagtagctgg gaccacagtc gcacgccacc acgtccggct aattattttt tttcgttttt    480
cgtagagagg gagtgtcgtt atgctgccca ggctggtttc aaactcctgg cctcaagcga    540
tcctcccacc tccggcttcc caaagtgctg ggattcgggg tgttagccac tgtcccggac    600
tacttctttt ttatcctgtc agaaaaacta tccatgtt                            638

<210> SEQ ID NO 88
<211> LENGTH: 1860
<212> TYPE: DNA
<213> ORGANISM: Homo sapiens A.4.D.36
<220> FEATURE:
<221> NAME/KEY: n
<222> LOCATION: (33)..(33)
<223> OTHER INFORMATION: a or g or c or t
<221> NAME/KEY: n
<222> LOCATION: (49)..(49)
<223> OTHER INFORMATION: a or g or c or t

<400> SEQUENCE: 88
ggcgcgcctg tccccaccta atgccacgat ccnccccctcc cccaccctnc cgcactgcct     60
cccttgcgcg tgtaggggag atccctgacc ttgtctgccc agctgcaggc cacttgccca    120
ggcggcccct cccttgttgc cacctcccgc ccagctcacc aggagcgtgt gccctgttgc    180
tactggcaac tgcctgtgcc taaagctcag cccccaaact ggcttaatgc tgattgatgg    240
tcagaaatag gatattttct ggaacagagc ggagcgctgg tgcaaggccc tctctgctgc    300
tgagtcctag ggacctcccg ggtggcaggc cttcctcctc ctctccttt ggccccaccc     360 accctacact acccctcaga gaccaacggg ctcttcggac atcctcatct caggttaagt    420
gctgagccag caagccagtg ttcgctttct tgctgagtaa caggcagcca ccccggaatt    480
tctcttctta tccttgaggc ttctgagttt tatgaatgag gcccgtgttg ctggacgcta    540
ccacttccct ttttattttc atccccacta acttgttcac tcgttcactc ctccttatac    600
ataggtacct aaaatagact accccctctag taaccagaac tattcctgca aacgcttaca    660
agagcatttt ccagaaataa atcatttcat atcagtatcc cttcctcagt catttcccgg    720
cttcatgcca cctccctcct aagacacaga attggtcatt tccaccactt taaagacaca    780
gtctagataa aaagcctgca tttataatgt tctttgcagg agtagctttt gcctattttg    840
tggggttttt gtttgttttt tgttttctgt ttgatactcc ctctcaaact gcagcctccc    900
ttcccttttc tgggatggca gcctccttct ctgagccatc ctggactaac attttctgga    960
ctaataaatt tctgcacctg tctctactcc ttctccttcc cagtctgact gtaaaggacc   1020
agatttcatt atcaaatcaa ttctctttag aagaactttg ttctgtagca tttctttcca   1080
ggaccccaat attttggca gagtattttc attatttaaa ttgtcgtact tagcttcttt     1140
ttgcctatgg acattacttt ggaaaaccat gtgatgtttc tgagtcactg atttgttcct   1200
ccaaacaaaa cttccttcag aggctcccat atgttgggca ccattgtagg ccccggggg    1260 tgggaatgga gcaaagacaa gacccaaatg ggtttcagca ttttaaagcc cccattacag   1320
ctggtttatg gttattgcta tgatggttaa tgtgataaca gcacactaca tttgactagg   1380
actttacagt ttacaaaagg ctttcaaaga cattatctcc attaatccca gcagcaggaa   1440
```

| | |
|---|---|
| ttttaaatag caaggattcc accaaaaggc ccagtaatgc tcaccaatcc tgcttaacca | 1500 |
| aaaagaaaaa tattgcaaat catcctaaca gctgatggag ctttaaaaca cagaataaac | 1560 |
| aattcataag aagcttctga agcttagtta ctggaatgta acttggagaa gataagtgaa | 1620 |
| atgcacgtaa catgtatatt accagaaggg tgtcttggag agaaactcca tcctggggct | 1680 |
| tcagtggcct ggtgaactgc tggaggtgga ggctttccag ggctctggac tattgcctta | 1740 |
| tcctaggatc taaaatggga tgaaagtgtt agcacaaagt tgctgggaga ctagcaaatt | 1800 |
| aagcaaaatg agtaggcaat gatgttactt tctttagcta caaagcattc ttgagatatc | 1860 |

<210> SEQ ID NO 89
<211> LENGTH: 2107
<212> TYPE: DNA
<213> ORGANISM: Homo sapiens A.4.E.32

<400> SEQUENCE: 89

| | |
|---|---|
| ggcgcgccac aaggccgtgg tgctgcgctg ccacgctgtg ctgctggcgc gggcgcacaa | 60 |
| ggcgcgcgcc ctggcccgcc tgctccgcca accgcgctg gcggccttca gcgacttcaa | 120 |
| gcgcctgcag cgccagagcg acgcgcgcca cgtgcgccag cagcatctcc gcgctggggg | 180 |
| cgccgccgcc tcggtgcccc gcgcccccact gcgccgcctg ctcaatgcca agtgcgccta | 240 |
| ccggccgccg ccgagcgagc gcagccgcgg ggcgccgcgc ctcagcagca tccatgagga | 300 |
| ggacgaggag gaggaggagg acgacgcgga ggagcaagag ggaggagtcc cccagcgcga | 360 |
| gcggccggag gtgctcagcc tggcccggga gctgaggacg tgcagcctgc ggggcgcccc | 420 |
| ggcgcccccg ccgcccgcgc agcccgcccg ctggaaggcc ggcccagggg agcgggcggg | 480 |
| ccaggcgcgc tgagagccga aggacaggac tcgcagcccc aggcccgacc cgccagactc | 540 |
| acagcctcca accccggccc tgcccgcttc ggctgccccg gccccggcc cgtgtctccc | 600 |
| ccgtggtctc cgtgttgtcc gccccgccgc ctcattttgg ctcaaggtga tgcctgatac | 660 |
| gcccttggtt attgggggt gttcctctct ccccacaccc ggagtttccc gggcctgcca | 720 |
| ttgtggaccc gccccctatg ctttacacct agtctctttg cccacagacc tcctcattcc | 780 |
| ctcccaaaac atcctctcaa gagaagggag gagaagtttc aagaaatcag gagggtggg | 840 |
| tttggacct gggcagggtg gaggcagtga ccttgccctt ggtccctcta gccttcttcc | 900 |
| ctgtgcaaaa aaaatgacc ctggagaggc attcttgtag agaagaatc tagcggccgg | 960 |
| ggagaattgg ggccgggccg gcggtgggca gagtccgctg ctatacacac agggaggaat | 1020 |
| tctcacgccc aagccccgcc tctctacgcc ttggaggact cctgtgactt cactgctctg | 1080 |
| cctctggaga acactgggag agtcctaccg acgttcaaac aacaggttag gccaggtaac | 1140 |
| agccctgcac caggccgctg cccacgcctc tgccctggca cccccagggg attccttgcc | 1200 |
| catcccatct ctctgcagac ggatgtgtgt ggccccctcc taggtgcccc acaaccagga | 1260 |
| ccaagatggg gctcccaaag gaggtaagga gaaccttttgg caggtgctta ggacactgac | 1320 |
| tacctagaaa gtagacgcag cagagttgct cccaagtcga ggctcctcag agcaggtggg | 1380 |
| tcctgacagc agtggattct cccagcagga tgaggaagga gggtgtgtta accaaccaag | 1440 |
| ggagtggggcc ccccacccag gtgtctccgc aagaccacaa aaagcccaaa gatctatgtg | 1500 |
| tcactgatca ttgtaaataa agtggacctg cttttacagc cctgtcacta ctcctgtgtt | 1560 |
| gtgtttaatg ccaggcctgc tgggggtgaa aaaatggatt gaagatcaga taagccacag | 1620 |
| gtgagcctgt atagctcccc ctggttacca tcagaaacct gaaagtagtt cttttgagca | 1680 |

```
-continued gccagagcca acccaggat taggacggga tctggggact gctgccagga agctgttcct     1740
taatgtcaga gaaggaggca gtaacttatg ccttgtctga aaatcacatg tgccaggctc     1800
cctggaggga cgtcggctgt ctgtctcagc ctcccaggat gtctgtacgc ctgggcactc     1860
agatgcaggt gtctgggaca tttggcaggg agggagcact gggctggggg cttctcataa     1920
gcatgtattc atatctctga gaaggttcat gtgtatttca gagcatatgg tatagactgt     1980
gtgtgtgctc tcagggatga gtgcgagcag gttgtaagag aatgtggtga gcagcccagt     2040
tttctttcag aggctctgga aaaacctgtc cagaccctgt ggcagtgtga gtcttcagct     2100
ggatatc                                                              2107

<210> SEQ ID NO 90
<211> LENGTH: 498
<212> TYPE: DNA
<213> ORGANISM: Homo sapiens A.5.E.28

<400> SEQUENCE: 90
ggcgcgccgg agttcgggct gccggctcct tagccgcggg gcgggggaga cgctcgggga      60
aggggagagg cgcgggcggg tgggaacggg cgggagacga gcggggacgg ggagacgcgc     120
cggaggcccg gagcccgcgc atgctcagtg cgcggccgga ggaggcgagc gctggggacg     180
cagcacctgc cccgcgcggc cgagaggcgg cagcccagg tccccagcgc gcgaaattag      240
taaagggcgc ctggcccgat tctcaggcaa gaggagatta tcagccggat tcccgtgcgg     300
ggacgtaggg gttgcgttgt tcagcggcca gggatgcgcc gaggcgatgt ctcctccctt     360
tacaacccga gtatcggggc acgaggaggc gcgaccttcc tgggtaccca aacctctggc     420
ctccgggaga cgcggaattc gggggatcgt taaggcgccc tggccaggga aacagatgct     480
tctgcgtctg ggctgaaa                                                  498
```